(12) United States Patent
Hawkins et al.

(10) Patent No.: US 9,084,605 B2
(45) Date of Patent: Jul. 21, 2015

(54) DIVERTICULUM INVERTING DEVICE

(71) Applicant: Empire Technology Development, LLC, Wilmington, DE (US)

(72) Inventors: Daniel Hawkins, Pleasanton, CA (US); John Adams, Snohomish, WA (US)

(73) Assignee: Empire Technology Development LLC, Wilmington, DE (US)

( * ) Notice: Subject to any disclaimer, the term of this patent is extended or adjusted under 35 U.S.C. 154(b) by 0 days.

(21) Appl. No.: 14/234,990

(22) PCT Filed: May 8, 2013

(86) PCT No.: PCT/US2013/040074
§ 371 (c)(1),
(2) Date: Jan. 24, 2014

(87) PCT Pub. No.: WO2013/169856
PCT Pub. Date: Nov. 14, 2013

(65) Prior Publication Data
US 2014/0200398 A1    Jul. 17, 2014

Related U.S. Application Data

(60) Provisional application No. 61/645,367, filed on May 10, 2012, provisional application No. 61/782,939, filed on Mar. 14, 2013.

(51) Int. Cl.
*A61B 17/10* (2006.01)
*A61B 17/128* (2006.01)
(Continued)

(52) U.S. Cl.
CPC ......... *A61B 17/1285* (2013.01); *A61B 17/0469* (2013.01); *A61B 17/0482* (2013.01); *A61B 17/122* (2013.01); *A61B 17/12013* (2013.01); *A61B 17/1227* (2013.01); *A61B 17/12131* (2013.01); *A61B 17/12145* (2013.01); *A61B 17/3421* (2013.01); *A61B 2017/00818* (2013.01); *A61B 2017/1142* (2013.01); *A61B 2017/12081* (2013.01); *A61B 2017/306* (2013.01); *A61B 2017/3445* (2013.01); *A61B 2017/3488* (2013.01)

(58) Field of Classification Search
CPC .... A61B 17/083; A61B 17/10; A61B 17/122; A61B 17/1285; A61B 2017/00367; A61B 17/08
USPC .................................................. 606/139, 144
See application file for complete search history.

(56) References Cited

U.S. PATENT DOCUMENTS

| 5,100,419 A | 3/1992 | Ehlers |
| 5,423,830 A | 6/1995 | Schneebaum et al. |

(Continued)

FOREIGN PATENT DOCUMENTS

WO    WO 2010/096174    8/2010

OTHER PUBLICATIONS

Raju, G.S., "*Endoscopic Closure of Gastrointestinal Leaks*", Clinical Reviews, vol. 104, pp. 1315-1320, The American College of Gastroenterology (2009).

(Continued)

*Primary Examiner* — Gregory Anderson
(74) *Attorney, Agent, or Firm* — Knobbe Martens Olson & Bear, LLP

(57) ABSTRACT

Minimally invasive endoscopic and laparoscopic devices and methods for inverting and closing a diverticulum. Devices can include a closing component such as a loop, a clip, or a suture that can allow the diverticulum to be removed or to slough off after necrosis.

28 Claims, 60 Drawing Sheets

(51) Int. Cl.
*A61B 17/04* (2006.01)
*A61B 17/12* (2006.01)
*A61B 17/122* (2006.01)
*A61B 17/34* (2006.01)
*A61B 17/00* (2006.01)
*A61B 17/11* (2006.01)
*A61B 17/30* (2006.01)

(56) References Cited

U.S. PATENT DOCUMENTS

| | | |
|---|---|---|
| 6,264,664 B1 | 7/2001 | Avellanet |
| 8,118,816 B2 | 2/2012 | Teague |
| 2006/0155305 A1 | 7/2006 | Freudenthal et al. |
| 2008/0249506 A1 | 10/2008 | Neustaedter et al. |
| 2008/0262514 A1 | 10/2008 | Gasche et al. |
| 2009/0105533 A1 | 4/2009 | Fujita |
| 2009/0105728 A1 | 4/2009 | Noda et al. |
| 2009/0270789 A1 | 10/2009 | Maxymiv et al. |
| 2010/0069925 A1 | 3/2010 | Friedman et al. |
| 2010/0280313 A1 | 11/2010 | Gasche et al. |
| 2011/0054498 A1 | 3/2011 | Monassevitch et al. |
| 2012/0010633 A1 | 1/2012 | Noda et al. |
| 2012/0059394 A1 | 3/2012 | Brenner et al. |

OTHER PUBLICATIONS

International Search Report and Written Opinion issued in PCT Application No. PCT/US2013/040074, dated Sep. 27, 2013.

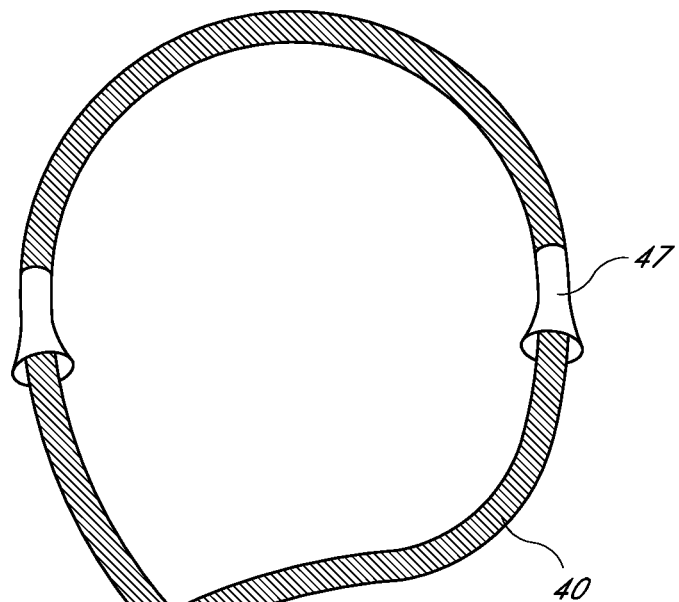
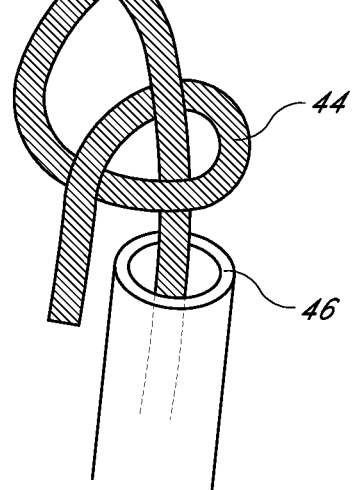
FIG. 13A
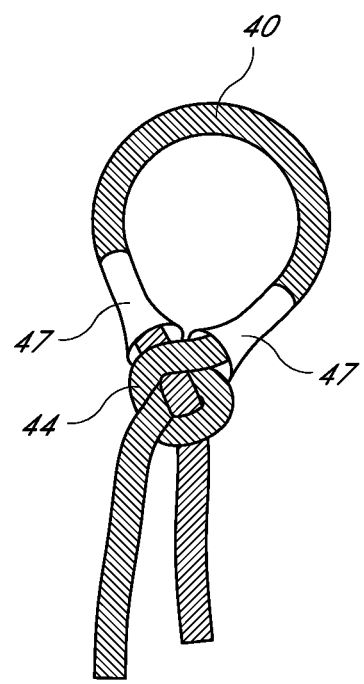
FIG. 13B

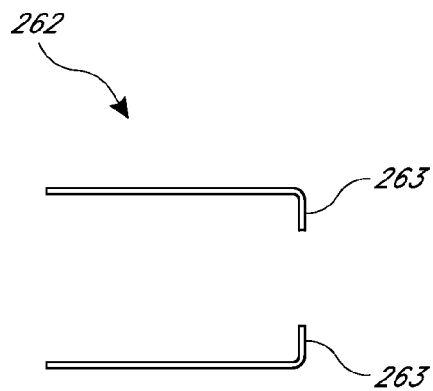
FIG. 19
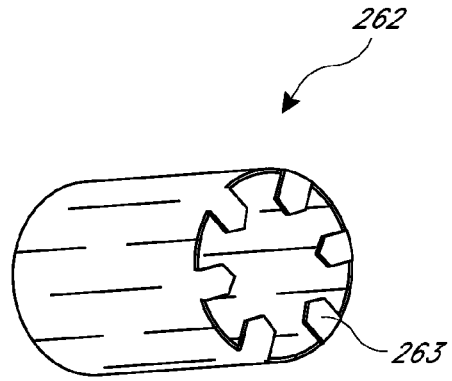
FIG. 20
FIG. 21
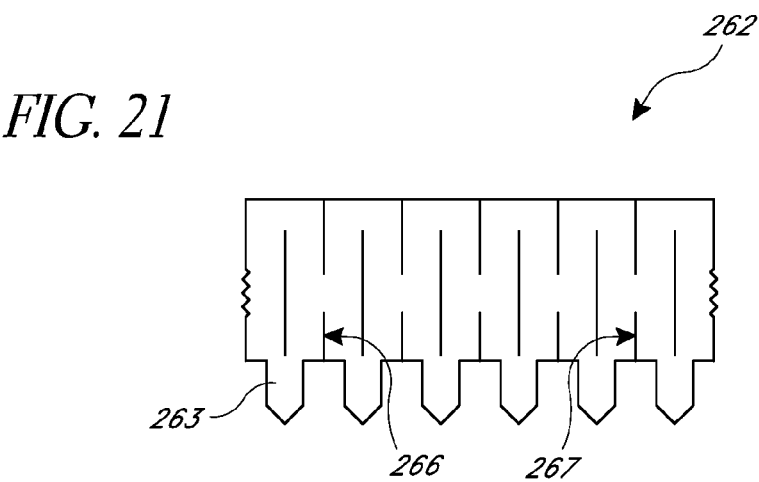
FIG. 22
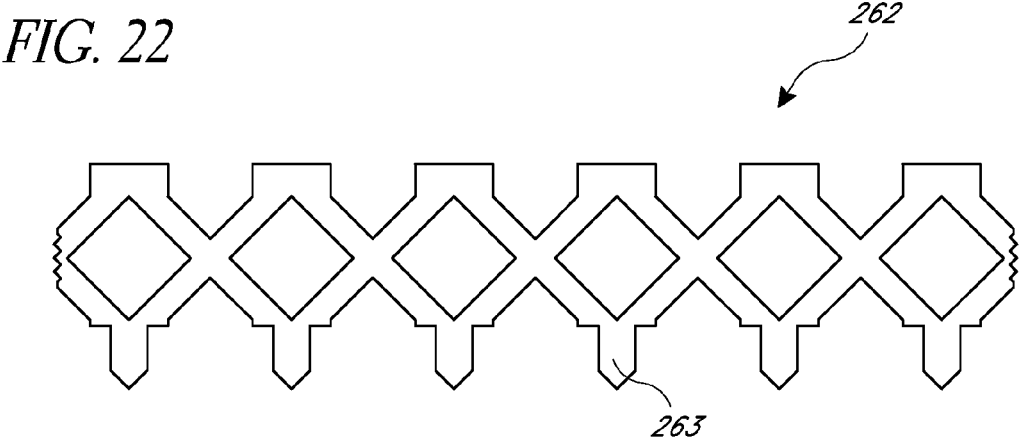

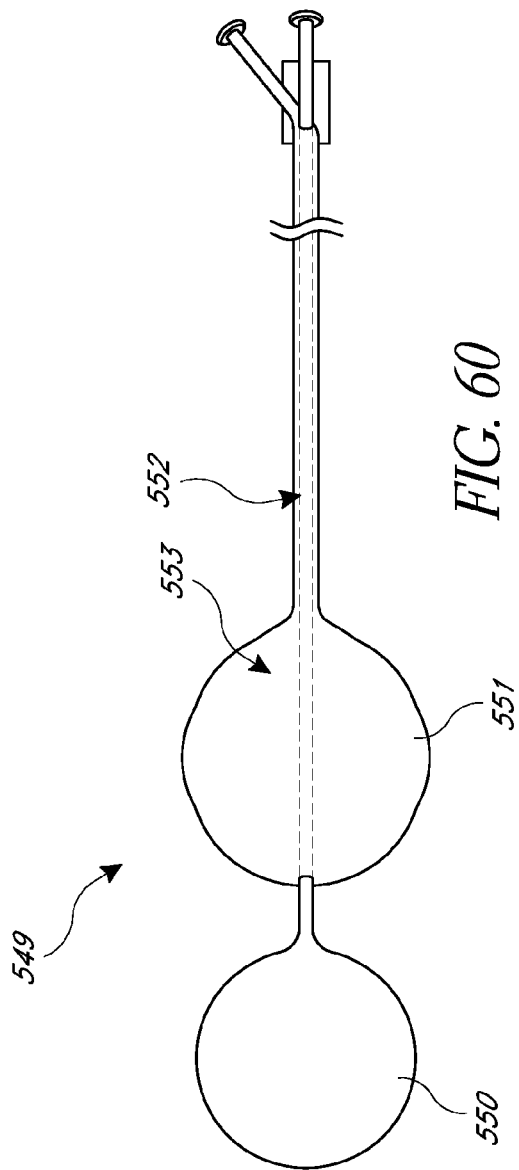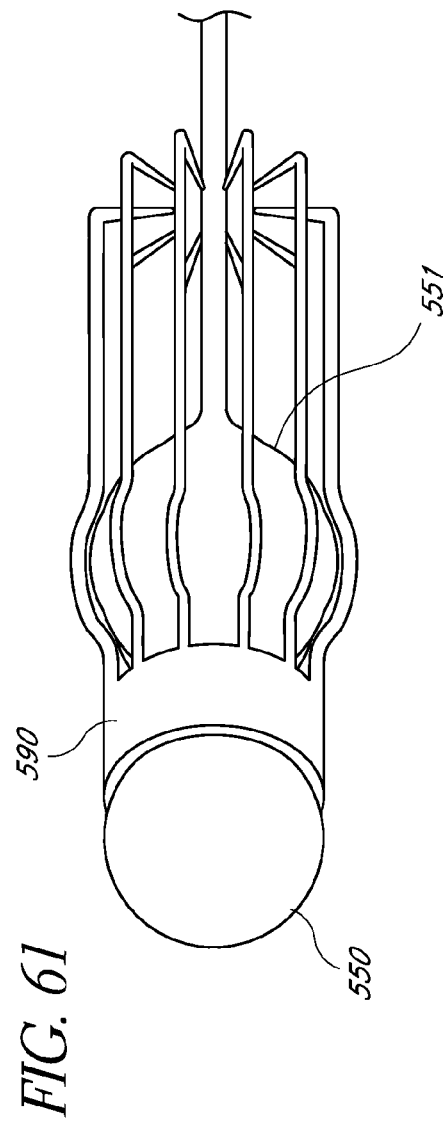

DIVERTICULUM INVERTING DEVICE

CROSS-REFERENCE TO RELATED APPLICATIONS

This application is a United States national stage application under 35 U.S.C. §371 of PCT Application No. PCT/US2013/040074 designating the United States, filed on May 8, 2013, which claims priority benefit of U.S. Provisional Patent App. No. 61/645,367, filed on May 10, 2012, and U.S. Provisional Patent App. No. 61/782,939, filed Mar. 14, 2013, each of which is hereby incorporated by reference in its entirety.

BACKGROUND

An outpouching of the colon or other body lumen, called a diverticulum, can become the site for inflammation known as diverticulitis, microperforation and/or bleeding. Current treatments may involve the surgical removal of segments of the body lumen. For extreme cases of diverticulitis, treatment can involve colon resection and placement of a colostomy. This approach results in significant healthcare costs and substantial pain for patients.

SUMMARY

A device for treating a diverticulum can include a basket having a first shape in which the basket is advanceable through a catheter lumen and a second shape upon expansion within a body lumen. The basket is operable in the first shape, the second shape, or any intermediate shape between the first shape and the second shape. The basket includes a plurality of ribs defining a distal rim of the basket. The plurality of ribs is configured to engage tissue of the body lumen proximate to an opening of a diverticulum. The basket further includes an outer polymeric film. The device further includes a closing component positionable around the basket, and a tubular member connectable to a source of negative pressure. The diverticulum is invertible at least partially into the basket upon application of a negative pressure through the tubular member.

The body lumen can be a colon. The basket in the second shape may be sized to receive an inverted diverticulum. A colonoscope may include the catheter lumen. The closing component operates between a first shape, a second shape, and any intermediate shape between the first shape and the second shape. The plurality of ribs can extend distally from a shared hub. The distal rim of the basket can include a plurality of spikes.

The closing component can be a closable loop. The closable loop may be configured to release from a position around the basket when tightened. A portion of the basket around which the closable loop may be inwardly angled to assist release of the closable loop. The closable loop can include a suture material. The suture material can include a resorbable suture material. The device can further include a knot pusher. The closable loop can include two stops spaced by a distance along the loop. The distance can be between about 6 millimeters and about 12 millimeters. The closable loop can be releasably bonded to the outer polymeric film. The releasable bond can be releasable upon tightening the closable loop to allow the closable loop to release from a position around the basket.

In some configurations, the diverticulum inverting device can include a delivery configured to slide coaxially over the basket. The closing component can include a closure clip coaxially over the delivery sheath.

The closure clip may have a first shape over the delivery sheath and a second shape when moved off of the delivery sheath. The second shape may be sized such that, when the closure clip is positioned around the diverticulum, the closure clip draws serosa at the opening to the diverticulum into contact with the serosa. The closure clip can include a distal end including pointed elements. The pointed elements can be configured to turn radially inward when the closure clip is in the second shape. The closing component can include a plurality of closure clips each including a proximal end including recesses configured to complement the pointed elements when the closure clips are in the first shape.

The delivery sheath may include a radially expandable distal end. The device may further include a pusher device configured to move the closure clip. The pusher device may include a radially expandable distal end. The pusher device can include a plurality of distally extending elements including bent tips engaged with a distal-most closure clip.

The device can include a first pusher and a second pusher coaxially over the first pusher. The closing component can include a spring ring coaxially over the first pusher and distal to the second pusher. The plurality of ribs can include detents proximate to the distal rim and configured to engage the spring ring. The basket may be releasably coupled to the first pusher.

The closing component may include a shape memory material. At least one of the closing component and the basket may include a drug coating. The drug coating may include at least one of a coagulation modifier and an antibiotic. The closing component may include the drug coating. The distal end of the closing component can include a closure clip including a distal end including the drug coating. The distal ends of the plurality of ribs can include the drug coating.

Another device for treating a diverticulum can include a basket having a first shape in which the basket is advanceable through a catheter lumen and a second shape sized to at least partially receive an inverted diverticulum upon deployment at a site within a body lumen. The basket includes a distal rim configured to engage tissue of a body lumen surrounding an opening to a diverticulum. The basket is operable in the first shape, the second shape, or any intermediate shape between the first shape and the second shape. The device also includes a closing component positionable around the basket.

The body lumen may be a colon. A colonoscope may include the catheter lumen. The distal rim of the basket may include a plurality of spikes. The closing component can operate between a first shape, a second shape, and any intermediate shape between the first shape and the second shape.

The closing component can include a closable loop. The closable loop can be configured to release from a position around the basket when tightened. A portion of the basket around which the closable loop is positioned can be inwardly angled to assist release of the closable loop. The closable loop can include a suture material. The suture material can include a resorbable suture material. The device can include a knot pusher. The closable loop can include two stops spaced by a distance along the closable loop. The distance can be between about 6 millimeters and about 12 millimeters. The closable loop can be releasably bonded to the basket. The releasable bond can be releasable upon tightening the closable loop to allow the closable loop to release from a position around the basket.

The diverticulum inverting device can include a delivery sheath configured to slide coaxially over the basket, and the closing component can include a closure clip coaxially over the delivery sheath. The closure clip can have a first shape over the delivery sheath and a second shape when moved off of the delivery sheath. The second shape can be sized such that, when the closure clip is positioned around the diverticulum, the closure clip draws serosa at the opening to the diverticulum into contact with the serosa. The closure clip can include a distal end including pointed elements The pointed elements can be configured to turn radially inward when the closure clip is in the second shape. The closure component can include a plurality of closure clips each including a proximal end including recesses configured to complement the pointed elements when the closure clips are in the first shape.

The delivery sheath can include a radially expandable distal end. The device can also include a pusher device configured to move the closure clip. The pusher device may include a radially expandable distal end. The pusher device may include a plurality of distally extending elements including inwardly-bent tips engaged with a distal-most closure clip.

The device may also include a first pusher and a second pusher coaxially over the first pusher. The closing component can include a spring ring coaxially over the first pusher and distal to the second pusher. The plurality of ribs can include detents proximate to the distal rim and configured to engage the spring ring. The basket may be releasably coupled to the first pusher. The closing component may include a shape memory material. At least one of the closing component and the basket can include a drug coating. The drug coating can include at least one of a coagulation modifier and an antibiotic. The closing component can include the drug coating. A distal end of the closing component can include a closure clip including a distal end including the drug coating. The distal ends of the plurality of ribs may include the drug coating.

A closure clip can include a generally tubular body including a first end, a second end, a plurality of slits between the first end and the second end, and, and a plurality of spikes proximate to the second end. The plurality of slits are expandable upon radial expansion of the closure clip from a first state to a second state. The plurality of spikes are configured to point in a direction substantially parallel to the longitudinal axis of the generally tubular body when the clip is in the first state and configured to point radially inward when the clip is in the second state. The tubular body is slideable over a delivery tube in the first state.

The generally tubular body can include a shape memory material. The plurality of slits can include a first slit extending from the first end of the generally tubular body toward the second end and a second slit extending from the second end of the generally tubular body toward, but not reaching, the first slit. The first slit and the second slit can be substantially straight. The first slit and the second slit can be substantially parallel to the longitudinal axis of the generally tubular body. The plurality of slits can include a third slit between the first end and the second end. The plurality of slits can include sets of the first slit and the second slit alternating with the third slit around the circumference of the generally tubular body.

The generally tubular body can include a plurality of recesses proximate to the first end. The recesses can be configured to complement the plurality of spikes at least when the closure clip is in the first state. The closure clip can include a drug coating over at least a portion of the generally tubular body. The drug coating can be over at least the plurality of spikes. The drug coating can be over at least a portion of the generally tubular body proximate to the second end. The drug coating can include at least one of a coagulation modifier and an antibiotic. The closing component can include the drug coating.

A method of treating a diverticulum includes advancing a device to a site proximate to a diverticulum in a body lumen. The device includes a basket defining a distal rim. The method further includes engaging at least a portion of tissue at the site with the distal rim of the basket, and applying pressure to the diverticulum sufficient to cause at least a portion of the diverticulum to invert into the body lumen.

The body lumen can be a colon. Advancing the device can include advancing the device through the body lumen. Applying the pressure can include applying negative pressure to the body lumen. Applying the pressure can include applying negative pressure within the basket. Applying the pressure can include applying positive pressure to the peritoneal cavity. Engaging the portion of the tissue may include engaging the portion of the tissue with a plurality of teeth along the distal rim of the basket.

The method may further include closing the diverticulum, including positioning a closing component positionable around the basket. The closing component can include a closable loop releasably coupled to the device at the distal rim. Closing the diverticulum can include tightening the closable loop around the inverted diverticulum.

The closing component can include a closure clip coaxially over a delivery sheath configured to slide coaxially over the expandable basket. Closing the diverticulum can include pushing the closure clip off of the delivery sheath. Closing the diverticulum can include positioning the delivery sheath at least partially over the basket and at least partially withdrawing the basket prior to pushing the closure clip. The method may include, after closing the diverticulum and without withdrawing the device from the body lumen, engaging a second closure clip. The method may include decreasing a pressure within the body lumen prior to closing the diverticulum.

A laparoscopic device for inverting a diverticulum may include a tubular member configured to be laparoscopically deployed at a site surrounding a diverticulum on a body lumen. The tubular member includes a working lumen and a distal end configured to engage in a substantially airtight suction fit with tissue at the site surrounding the diverticulum. Upon application of positive pressure to the working lumen, at least a portion of the diverticulum is inverted into the body lumen.

The distal end of the tubular member may include a hollow suction flange configured to be coupled to a negative pressure line. Upon application of negative pressure through the negative pressure line, the distal end of the tubular member engages in the substantially airtight suction fit with the tissue at the site surrounding the diverticulum. The suction flange can include a distal surface including a plurality of holes. The tubular member can include a proximal end including a sealed port configured to allow tools to enter the working channel.

A closure clip assembly for use with a laparoscopic diverticulum inverting device can include a deployment tool, and a closure clip including a distal region and a plurality of closure arms extending proximally from the distal region. The plurality of closure arms include proximal tips biased radially inward.

The distal region of the closure clip can be internally threaded. The deployment tool can includes an externally threaded distal region configured to threadably engage the internally threaded distal region of the closure clip, an expander region proximal to the externally threaded distal region, an elongate shaft proximal to the expander region, and a handle proximal to the shaft. The expander region can be configured to radially expand the plurality of closure arms of the closure clip from an initial substantially parallel position to an expanded radially outward position as the handle is rotated in a first direction. The expander region can be configured to allow the plurality of closure arms of the closure clip to return toward the initial substantially parallel position as the handle is rotated in a second direction opposite the first direction. The proximal tips can be configured to draw toward each other when the plurality of closure arms of the closure clip return toward the initial substantially parallel position. The deployment tool can include a frangible region between the expander region and the shaft. The deployment tool can include a stop distal to the externally threaded distal region. The stop can have a larger diameter than the externally threaded distal region. The closure arms can include curved regions sized to fit around the expander region. The plurality of closure arms can be in the initial substantially parallel position when the expander region is within the curved regions.

The plurality of closure arms can include detents. The deployment tool can include an elongate shaft, a spring ring around the distal region of the closure clip, and a pulling mechanism coupled to the spring ring. The elongate shaft may include an atraumatic distal end. The pulling mechanism can include suture material. The plurality of closure arms of the closure clip may be radially inwardly compressed when the pulling mechanism proximally retracts the spring ring.

The deployment tool can include an expandable member and an inflation lumen in fluid communication with the expandable member. The expandable member may be configured to radially expand the plurality of closure arms of the closure clip from an initial substantially parallel position to an expanded radially outward position as the expandable member is inflated through the inflation lumen. The deployment tool can further include a second expandable member distal to the expandable member, and a second inflation lumen in fluid communication with the second expandable member. The deployment tool may be configured to allow the plurality of closure arms of the closure clip to return toward the initial substantially parallel position as the expandable member is deflated. The proximal tips can be configured to draw toward each other when the plurality of closure arms of the closure clip return toward the initial substantially parallel position. The plurality of closure arms can include curved regions sized to fit around the expandable member.

The closure clip can include a shape memory material. The plurality of closure arms may be shape set in a substantially parallel configuration. The plurality of closure arms may be shape set in a radially expanded configuration.

A laparoscopic assembly can include the laparoscopic device and the closure clip assemblies described above. The laparoscopic assembly may include a colonoscope.

A method of inverting a diverticulum on a colon through a laparoscope can include applying a negative pressure to a distal surface of a hollow suction flange at a distal end of a tubular member that is against tissue surrounding the diverticulum, the negative pressure being sufficient to create a substantially airtight suction fit between the distal surface of the flange and the tissue surrounding the diverticulum, and inverting at least a portion of the diverticulum.

Inverting at least the portion of the diverticulum can include applying a positive pressure to a working tube of the tubular member of the laparoscopic device, the positive pressure is sufficient to cause at least the portion of the diverticulum to invert into the colon. Inverting at least the portion of the diverticulum can include pushing the diverticulum with an atraumatic distal end of a pusher tube, the pushing being sufficient to cause at least the portion of the diverticulum to invert into the colon. Inverting at least the portion of the diverticulum can include pushing the diverticulum with a distal inflatable element, the pushing being sufficient to cause at least the portion of the diverticulum to invert into the colon.

The method can include advancing a closing assembly through a working lumen of the tubular member to the inverted diverticulum, and closing the diverticulum. The closing assembly can include a deployment tool and a closure clip.

The closure clip can include an internally threaded distal region and a plurality of closure arms extending proximally from the internally threaded distal region and including proximal tips. The deployment tool can include an externally threaded distal region configured to threadably engage the internally threaded distal region of the closure clip, an expander region proximal to the externally threaded distal region, an elongate shaft proximal to the expander region, and a handle proximal to the shaft. Closing the diverticulum may include advancing the closure clip into the inverted diverticulum, rotating the handle in a first direction to radially expand the plurality of closure arms from an initial substantially parallel position to an expanded radially outward position, engaging a portion of tissue at a site proximate to the diverticulum with proximal tips of the plurality of closure arms, and rotating the handle in a second direction opposite the first direction to contract the plurality of closure arms from the expanded radially outward position toward the initial substantially parallel position. The deployment tool may include a frangible region between the expander region and shaft, and closing the diverticulum can include, after closing the diverticulum, severing the frangible region, and, after severing the frangible region, removing the shaft and the handle.

The closure clip can include a distal region and a plurality of closure arms extending proximally from the internally threaded distal region and including proximal tips. The deployment tool can include an elongate shaft, a spring ring around the distal region of the closure clip, and a pulling mechanism coupled to the spring ring. Closing the diverticulum can include advancing the closure clip into the inverted diverticulum, engaging a portion of tissue at a site proximate to the diverticulum with proximal tips of the plurality of closure arms, and proximally retracting the spring ring over the plurality of closure arms to contract the plurality of closure arms radially inward. Closing the diverticulum can include decoupling the pulling mechanism from the spring ring.

The closure clip can include a distal region and a plurality of closure arms extending proximally from the internally threaded distal region and including proximal tips. The deployment tool can include an expandable member and an inflation lumen in fluid communication with the expandable member. Closing the diverticulum can include advancing the closure clip into the inverted diverticulum, inflating the expandable member through the inflation lumen, engaging a portion of tissue at a site proximate to the diverticulum with proximal tips of the plurality of closure arms, and deflating the expandable member through the inflation lumen. The deployment tool can include a second expandable member and a second inflation lumen in fluid communication with the second expandable member. The second expandable member may be distal to the expandable member.

The plurality of closure arms may include proximal tips biased radially inward. Engaging the portion of tissue at the site proximate to the diverticulum with the distal plurality of closure arms may include extending the tips through the tissue at the site proximate to the diverticulum.

The closing assembly can include a suturing tool. Closing the diverticulum may include suturing the tissue surrounding the inverted diverticulum. Suturing the tissue surrounding the inverted diverticulum can include tying a purse string suture.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through use of the accompanying drawings.

FIG. 13A is a perspective view of an embodiment of a diverticulum inverting device including a closable loop including stops.

FIG. 13B is a perspective view of the closable loop of FIG. 13A after being tightened.

FIG. 19 is a cross-sectional view of a closure clip showing radially inward orientation of tissue-engaging teeth.

FIG. 20 is a perspective view of the closure clip of FIG. 19 showing radially inward orientation of tissue-engaging teeth.

FIG. 21 is a projected side view of the closure clip of FIG. 19 in a compressed state.

FIG. 22 is a projected side view of the closure clip of FIG. 19 in an expanded state.

FIG. 60 is a cross-sectional view of a deployment tool including a distal expandable member and a proximal expandable member.

FIG. 61 is a perspective view of a closure clip assembly including the deployment tool of FIG. 60 over the closure clip of FIG. 59.

DETAILED DESCRIPTION

Figure 1:
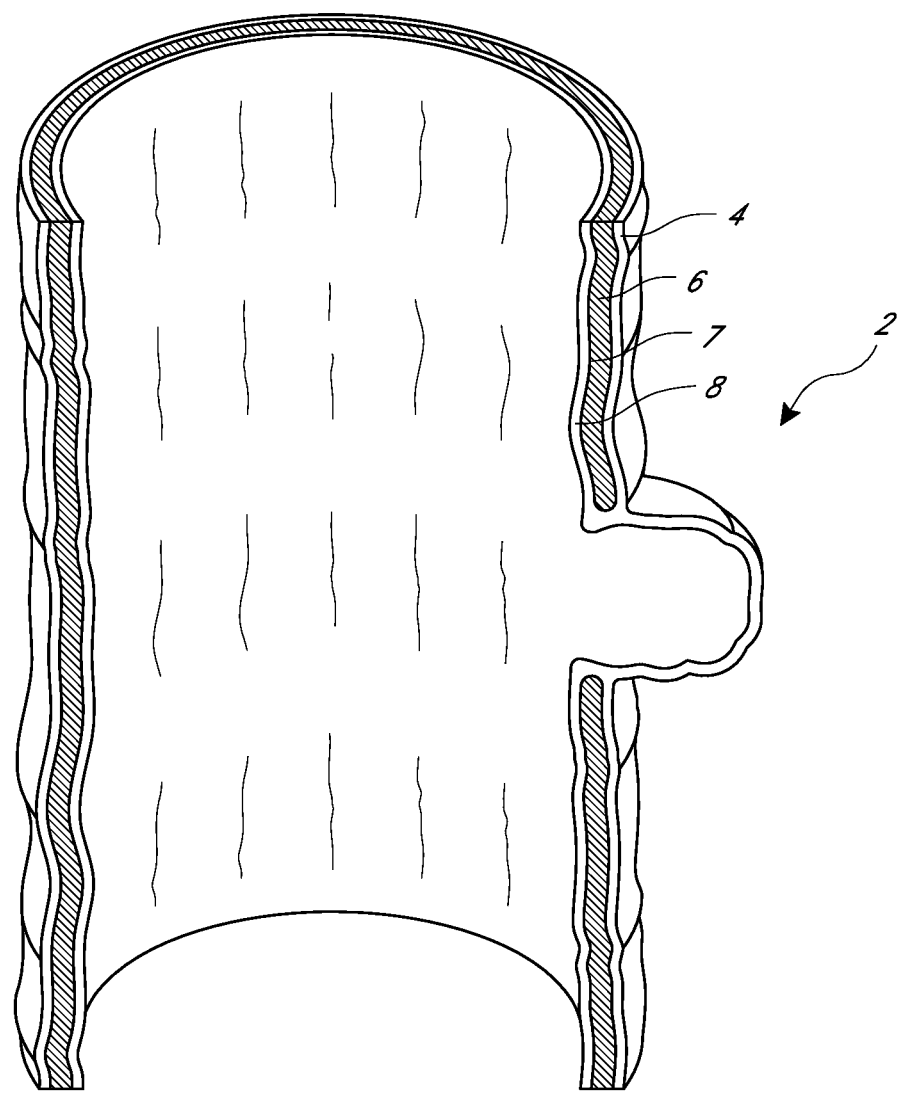
FIG. 1 is a cross-sectional view of a diverticulum of the sigmoid colon showing the structural makeup.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated and made part of this disclosure.

Described herein are various components of the device or apparatus which may be made of a shape memory alloy (SMA). The use of a SMA in medical devices is well known in the art and those skilled in the manufacture and use of medical devices having component(s) made from SMA will appreciate its utility in the descriptions herein. In addition to SMA, any component of any embodiment described herein may be made from any medical grade material, including but not exclusively limited to any metal, alloy, polymer, fiber, ceramic, or any combinations thereof.

Diverticula of the lower colon can become the site for microperforation and inflammation called diverticulitis and/or bleeding. A device disclosed herein can be used to invert, close, and remove diverticula of the colon, sparing the patient of colon resection surgery. Current treatment strategies for treating diverticula may involve the surgical removal of large segments of the colon, and in extreme cases, the placement of a colostomy. An alternative treatment strategy is provided that can be performed during routine colon examinations, where a colonoscope is used to identify a diverticulum, and also deliver the tools to the site for inverting and ligating the diverticulum. The working channel of the colonoscope may be used to deliver a self-expanding basket to invert and capture the diverticulum, and to deploy a ligature, which snares and ties off the inverted diverticulum. The device may be configured to fit within the working channel of the colonoscope, thereby allowing the physician/operator to identify an individual diverticulum, invert it, and tie it off with a ligation at the base of the diverticulum. Means can be provided to verify that the full diverticulum is inverted and that the base is sealed in such a manner as to reduce the opening in the muscular layer of the colon wall, to reduce or minimize circulation of blood into the tissue.

In conventional colonoscopy procedures, a gastroenterologist advances a colonoscope completely to the patient's appendix while inflating the colon with air. Visual examination is preformed while retracting the colonoscope. Diverticula are generally easy to see and diagnose visually. If treatment of the diverticulum is deemed warranted by the physician, the whole colonoscope must be removed (4-5 ft. long) in order to slide an overtube assembly onto the colonoscope. Then the colonoscope is reinserted while looking to find the diverticulum. This is a tedious, time-consuming, and potentially dangerous procedure. In contrast, according to embodiments disclosed herein, once a diverticulum is detected, the physician can keep the colonoscope in the colon and focused on the diverticulum, and advance the disclosed device down the working channel of the colonoscope in order to treat the diverticulum quickly. Once the diverticulum is inverted and tied off, further examination of the colon can continue and other treatments, such as polyp removal, can continue also using the working channel. The substantial burden of removing the colonoscope from the patient, sliding an overtube assembly onto the distal end of the colonoscope, reinserting the colonoscope with overtube assembly, and relocating the diverticulum is completely gone.

Disclosed herein are tools, devices, assemblies, and methods for inverting and closing diverticula in a body lumen. The tools, devices, and assemblies may be configured for endoscopic delivery, e.g., through a working channel of a colonoscope. The tools, devices, and assemblies may alternatively be configured for laparoscopic delivery, e.g., to the outer surface of the colon.

A negative pressure may be applied through a diverticulum inverting device within the body lumen directly to an opening to a diverticulum, thereby causing the diverticulum to invert into the diverticulum inverting device within the body lumen. The negative pressure may alternatively be applied non-specifically within the body lumen itself, thereby causing any or at least some diverticula to invert into the body lumen. Either with or instead of a negative pressure, a positive pressure may be applied from outside the body lumen. For example, a positive pressure may be applied to the body cavity within which the body lumen resides (e.g., to the peritoneal cavity, thereby causing any or some diverticula to invert into the colon). Alternatively, a positive pressure may be applied via a laparoscopic tube directly to the diverticulum, causing it to invert into the colon.

A diverticulum can invert into a diverticulum inverting device defining a distal rim that supports a closable loop or ligature, or a closure clip. The diverticulum inverting device can contact the tissue surrounding the opening to a diverticulum with a substantially air-tight, film-covered basket, which can be operably coupled to a negative pressure line that can apply a negative pressure through the diverticulum inverting device from within the body lumen within the basket to suck the diverticulum at least partially into the basket, and the diverticulum inverting device can then deploy a closable loop or ligature or closure clip around the neck of the inverted diverticulum, the loop or ligature or closure clip being closable to thereby ensnare the diverticulum. Multiple closure clips may be loaded in a single device for serial deployment over multiple diverticula. The device may include a basket that is neither film-covered nor substantially air-tight, such that negative pressure may be applied to the body lumen rather than to the basket, causing the diverticulum to invert at least partially into the basket. A detachable basket may be secured around a closed and inverted diverticulum by a spring ring. Portions of the device contacting the diverticulum can include a drug coating.

A laparoscopic device may be used to apply a positive pressure directly to a diverticulum from outside of the body lumen to which the diverticulum is attached. The laparoscopic device may contact the base of a diverticulum. The laparoscopic device can surround the diverticulum within a working channel of the device. A negative pressure line can apply a negative pressure within a portion of the laparoscopic device to holes in contact with tissue surrounding the diverticulum, creating a substantially airtight fit, and a positive pressure can be applied to the working channel, at least partially inverting the diverticulum into the body lumen. A suturing device may be deployed through the working channel of the laparoscopic device to close an inverted diverticulum. Alternatively, a clip can be deployed through the working channel into the diverticulum, the clip being configured to engage the base of the diverticulum and draw it closed upon threaded interaction with a rotating shaft, pulling of a spring ring, or balloon deflation. Portions of the device contacting the diverticulum can include a drug coating.

FIG. 1 is a cross-sectional view of a diverticulum 2 of a sigmoid colon. The walls of the colon generally include an outer layer of serosa 4, an inner layer of mucosa 8, and a muscular layer 6, or muscularis, between the mucosa 8 and serosa 4. In the region of a typical diverticulum 2, a hole may exist in the muscular layer 6, in which case the walls of the diverticulum 2 may have only the outer layer of serosa 4 and the inner layer of mucosa 8. A submucosal region 7 also exists between the mucosa 8 and serosa 4 layers. A diverticulum 2 typically bulges one to two centimeters through the colon wall.

Figure 2:
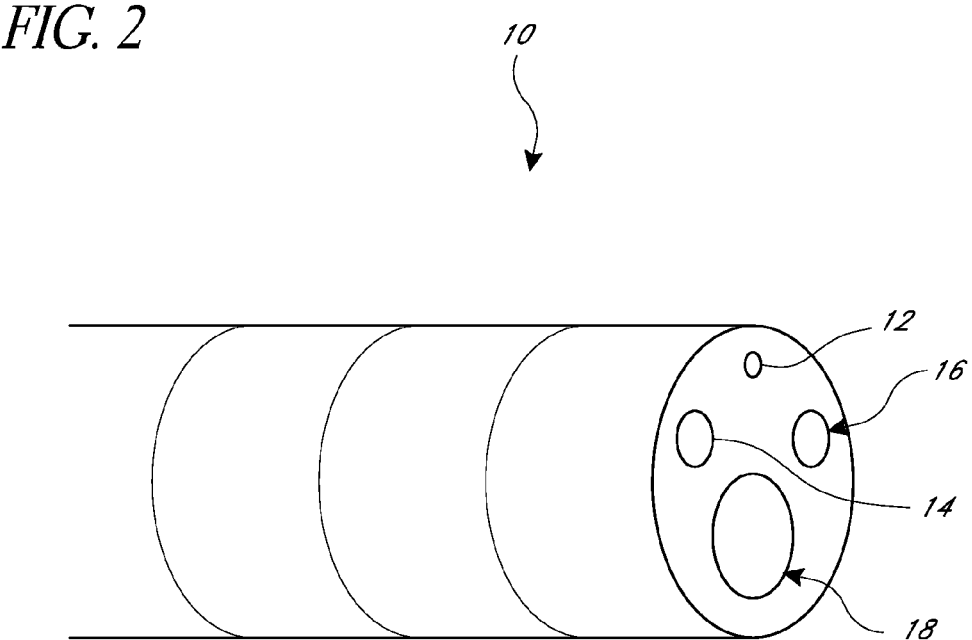
FIG. 2 is a side perspective view of the working end of a colonoscope.
Figure 3:
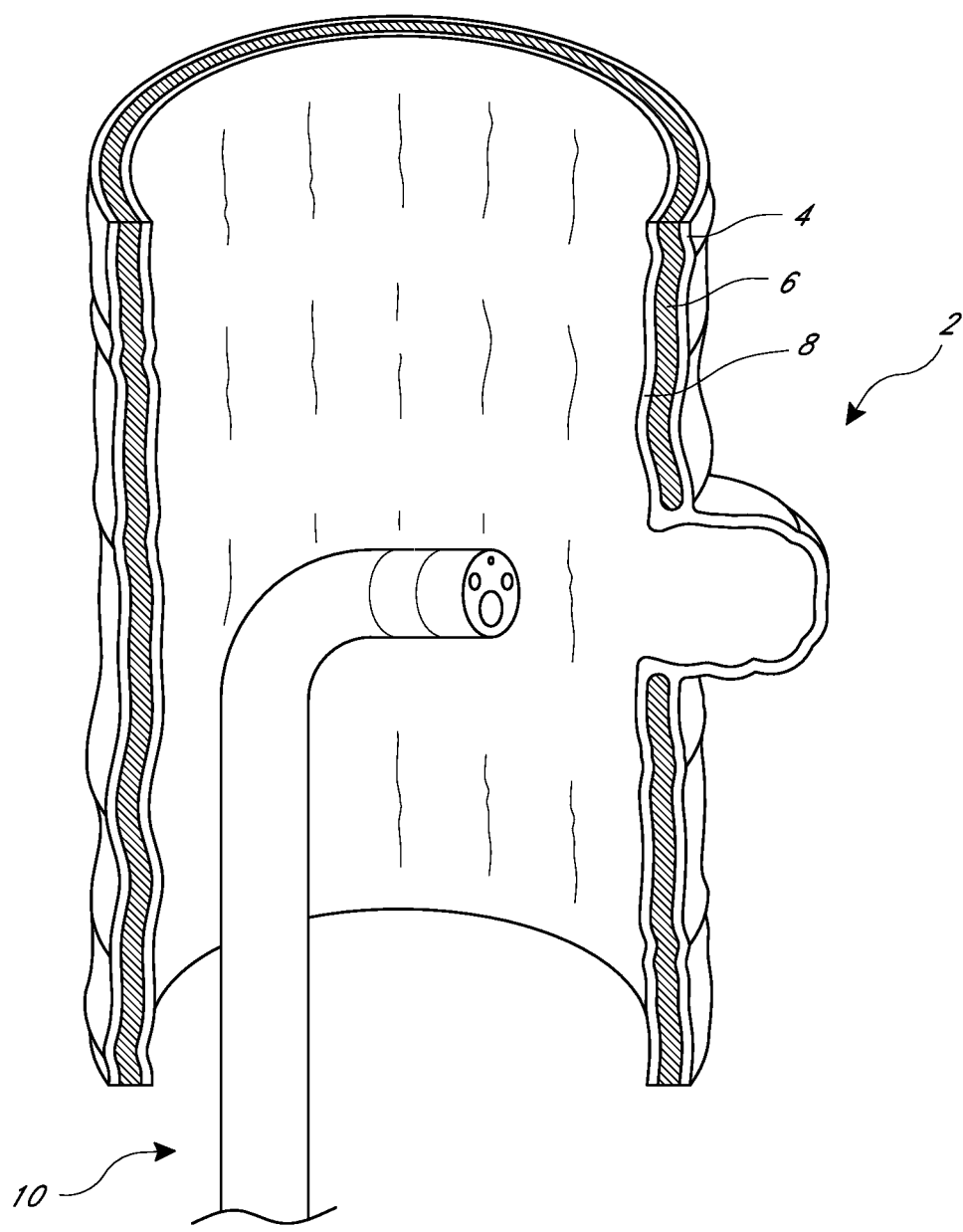
FIG. 3 is a perspective view of a colonoscope bent to view a diverticulum, which is shown in cross-section.

FIG. 2 is a side perspective view of the working end of a colonoscope 10. The colonoscope 10 generally includes one or more of a light source 12 useful to illuminate the area of viewing; a viewing lens 14; a lumen 16, which can include a source of liquid such as water or saline, a source of air, and/or a source of negative pressure; and a working channel 18 through which tools such as biopsy forceps, graspers, or manipulators are typically passed. Colonoscopes 10 are flexible and can be manipulated to bend and articulate along segments up to 180 degrees. For example, as illustrated in FIG. 3, a colonoscope 10 can be easily bend 90 degrees to view a diverticulum 2 (otherwise referred to herein as a "tick"). Once the operator of the colonoscope 10 sees the diverticulum 2, he or she can position the scope 10 proximate to the diverticulum 2 and prepare to deliver a diverticulum inverting device down the working channel 18 to reach a diverticulum 2.

Although described in more detail below, the diverticulum inverting device most basically includes a basket, or inverted umbrella, structure that can be delivered through the working channel 18 of a colonoscope 10 in a first shape, and can assume a second shape or any intermediate shape between the first and second shape once the basket exits the working channel 18. For ease of description, the first shape may be referred to herein as a collapsed or delivery configuration and the second shape may be referred to herein as an expanded configuration. The basket may also be referred to as an expandable basket.

When the basket exits the working channel 18 and is in the expanded configuration, it can be positioned around the base, or opening, of a diverticulum 2, and pressure can be applied to at least partially invert the diverticulum 2 into the basket. The pressure can be positive or negative, and can be applied from within the basket, within the colon generally, or from outside the colon, such as the peritoneal cavity.

A diverticulum closing component, such as a closable loop, ligature or clip, can be positioned around the basket. Once the diverticulum 2 is inverted, the closing component can be released from around the basket onto the diverticulum 2, whereupon the closing component can maintain the diverticulum 2 in a closed state, allowing the diverticulum 2 to heal on the serosa 4 side and necrose on the mucosa 8 side, eventually being absorbed or falling off. This is a simple process that can be repeated for each diverticulum 2, and may save the patient the significant risk of colon removal surgery.

Figure 4:
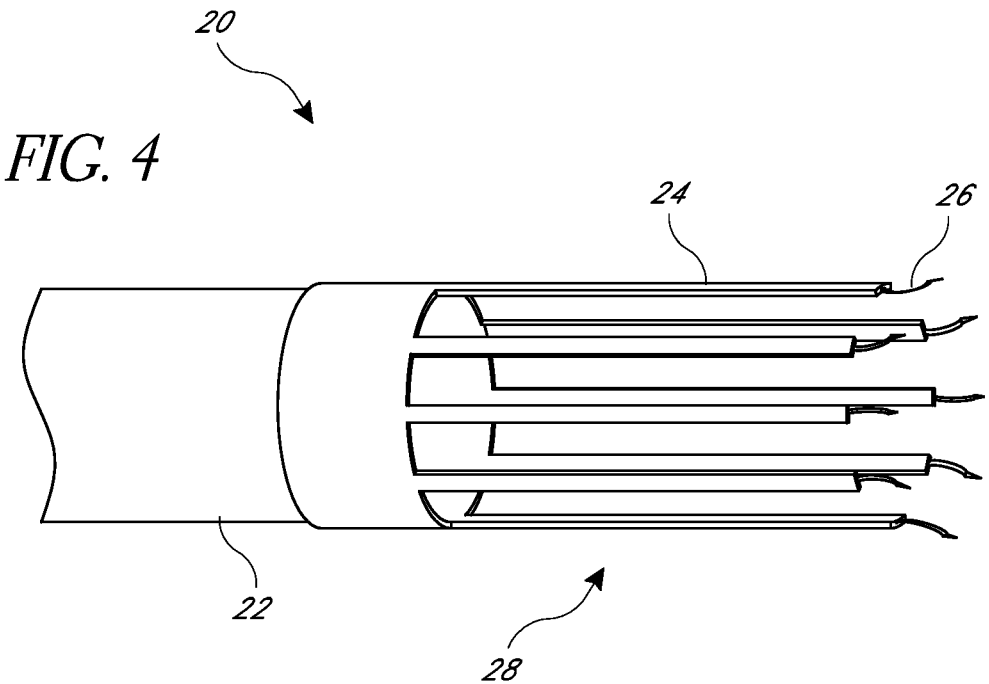
FIG. 4 is a side perspective view of an embodiment of a diverticulum inverting device including a tube cut in the configuration of a basket including arms.

FIG. 4 is a side perspective view of an embodiment of a diverticulum inverting device 20 including a tube cut in the configuration of a basket 28 including arms 24. The device 20 can be sized to fit within the working channel 18 of the colonoscope 10. The working channel 18 is typically between two and three millimeters diameter, although it can be larger or smaller. The diverticulum inverting device generally includes a flexible tube 22 including a basket, or umbrella, 28 at a distal end. The basket 28 can be formed or cut to include arms 24 each including a spike 26 at a distal end. As illustrated in FIG. 4, the basket 28 is in a collapsed configuration.

Figure 5:
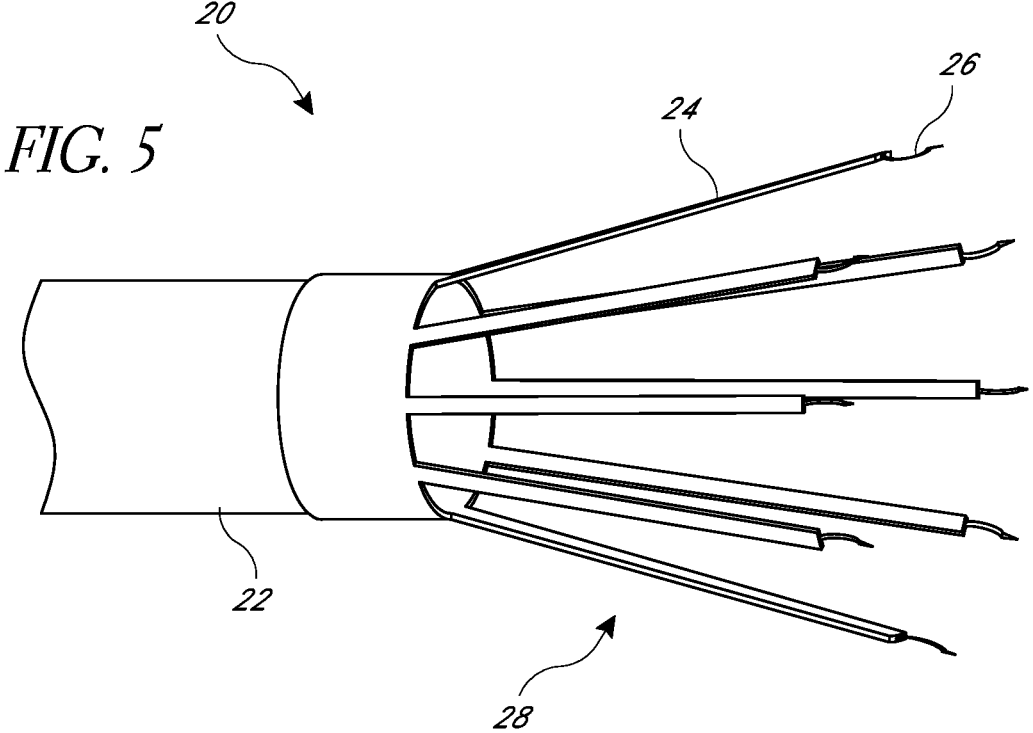
FIG. 5 is a side perspective view of the basket of the device of FIG. 4 in an expanded configuration such that the arms of the basket expand outward after exiting from the working channel of a colonoscope, thereby defining a distal rim.

FIG. 5 is a side perspective view of the basket 28 of the device 20 in an expanded configuration. In the expanded configuration, the arms 24 of the basket 28 extend at least partially radially outward from a shared hub, the distal ends of the arms 24 defining a distal rim that is generally circular in shape. The rim need not be circular, however, and the basket 28 can be configured such that the arms 24 define a distal rim that is oval-shaped, elliptical, egg-shaped, polygonal, or other shapes. The diameter of the distal rim can be greater than one centimeter. More specifically, the diameter can be between about 1 centimeter and about 2 centimeters, between about 2 centimeter and about 4 centimeters, or greater than about 4 centimeters. Alternatively, the diameter can be between about 0.5 centimeters and about 1 centimeters, or less than about 0.5 centimeters.

Because the arms 24 of the basket 28 retain some flexibility in the expanded configuration, they can compress into a collapsed configuration for insertion through the working channel 18 of the colonoscope 10. Once the diverticulum inverting device 20 is out of the working channel 18, however, the basket 28 can return to its expanded configuration, as illustrated in FIG. 5.

Figure 6:
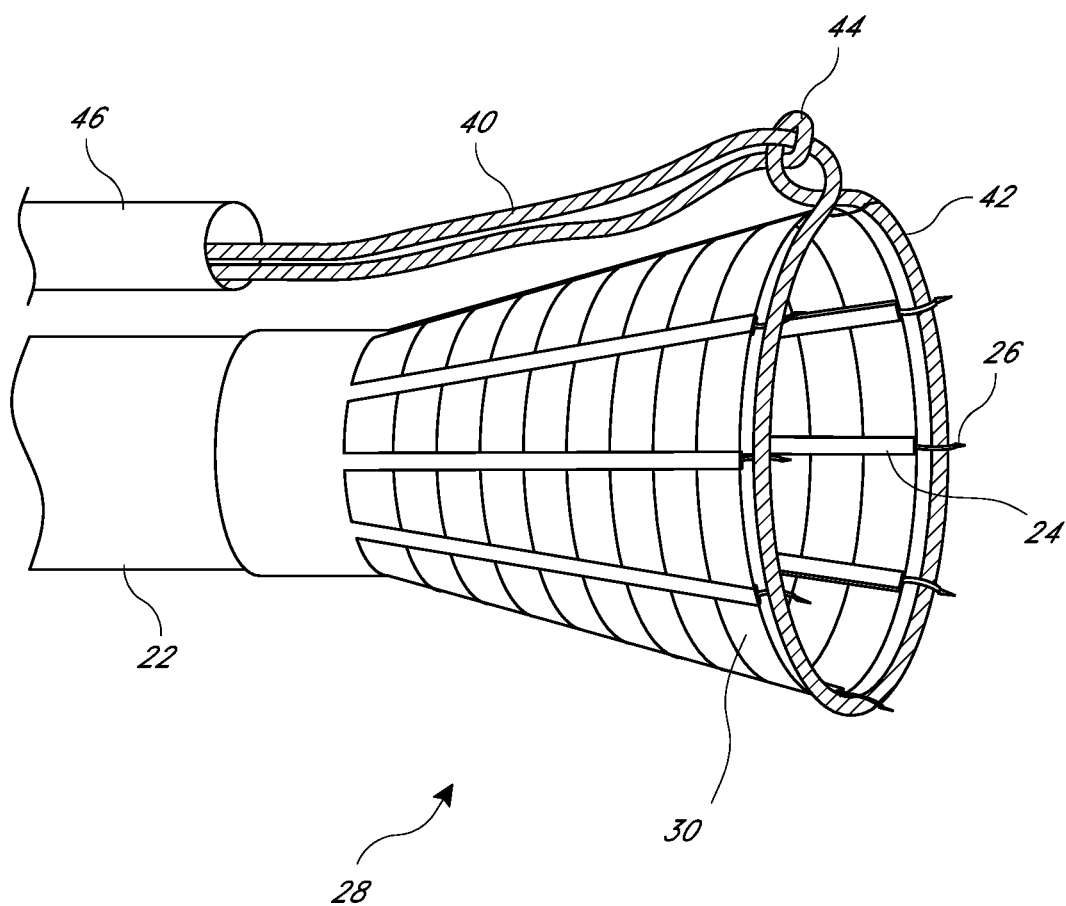
FIG. 6 is a side view of an embodiment of the expanded basket including a film of material secured to the arms of the basket and a closable loop.

FIG. 6 is a side view of an embodiment of the expanded basket 28 including a film 30 of material secured to the arms 24 of the basket 28 and a closable loop 42. The film 30 can include any flexible material, such as polyurethane or similar materials. The film 30 may be bonded to the arms 24 to form a substantially airtight seal. The tube 22 may be connected to a source of negative pressure, although the tube 22 can still be used to manipulate the basket 28. The substantially airtight seal between the film 30 and the arms 24 can be sufficiently airtight that a negative pressure applied within the tube 22 generates a negative pressure within the basket 28, which can at least partially invert a diverticulum 2 into the basket 28, as described in more detail below with regard to FIGS. 10-12.

With continuing reference to FIG. 6, the diverticulum inverting device can also include a suture material 40, such as a polypropylene suture or a dissolvable or resorbable suture material as is known in the art, that forms a closable loop 42 positioned around the distal rim of the basket 28. The closable loop 42 can be used to tie off or close an inverted diverticulum 2, which can cause the serosa 4 side to heal shut and the mucosa 8 side to necrose. A closable loop 42 is just one of many diverticulum closing devices that can be positioned around the basket 28.

The closable loop can include a knot 44 configured to be tightened. The closable loop 42 can also or alternatively include clips or other elements that can tighten the closable loop 42 to a desired size and generally maintain the closable loop 42 at the desired size. Although not necessary, as illustrated in FIG. 6, the diverticulum inverting device includes a knot pusher 46 to help tighten the closable loop 42. The knot pusher 46 can be extended against the knot 44, applying pressure on the knot 44 to tighten the closable loop 42. When a knot pusher 46 is used, at least one of the loose ends of the suture material 40 can run into the knot pusher 46, and the suture material 40 and knot pusher 46 can extend into the working channel 18 of the colonoscope 10. Also as illustrated in FIG. 6, the knot pusher 46 and suture material 40 are outside of tube 22, but they can alternatively be positioned within tube 22.

Figure 7:
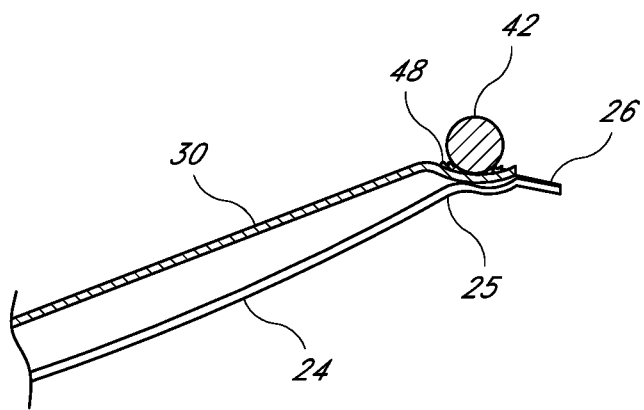
FIG. 7 is a partial cross-sectional view of an embodiment of one of the arms of the basket of FIG. 6 supporting the closable loop along a distal end region of the arm using a releasable adhesive.

The closable loop 42 can be releasably bonded to the basket 28. This allows the closable loop 42 to release from the basket 28 and move onto an inverted diverticulum 2, as described in more detail with reference to FIGS. 10-12. FIG. 7 is a partial cross-sectional view of an embodiment of one of the arms 24 of the basket 28 of FIG. 6 supporting the closable loop 42 along a distal region of the arm 24 using a releasable adhesive 48. Alternatively, the closable loop 42 can be bonded to the film 30 with wax in place of the releasable adhesive 48, or with a thermal bond. The closable loop 42 may alternatively be bonded to the arms 24, whether at the spikes 26 or at a more proximal location.

The arms 24 can be configured to affect the ease with which a closable loop 42 releases from the basket 28. For example, as illustrated in FIG. 7, the arms can have an angle 25. The angle 25 can help ensure that the closable loop 42 will tend to move distally off of the basket 28 as the closable loop 42 is tightened rather than sliding proximally down the basket 28. The angle 25 and the strength of the releasable adhesive 48 can be altered to create a desired tightening strength needed to break the bond between the closable loop 42 and the basket 28. The angle 25 of the arms 24 and the strength of the releasable adhesive 48 can be configured such that the closable loop 42 will not accidentally fall out of position, but will release onto a diverticulum 2 when desired.

Figure 8:
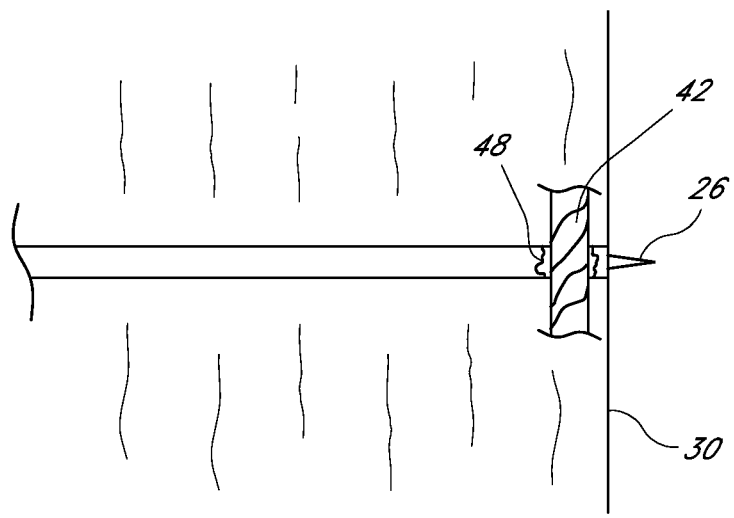
FIG. 8 is a top view of the embodiment of FIG. 7.

FIG. 8 is a top view of the embodiment of FIG. 7. In FIG. 8, it is clear that the film 30 extends completely under the closable loop 42. In this embodiment, the film 30 extends all the way to the base of the spikes 26.

Figure 9:
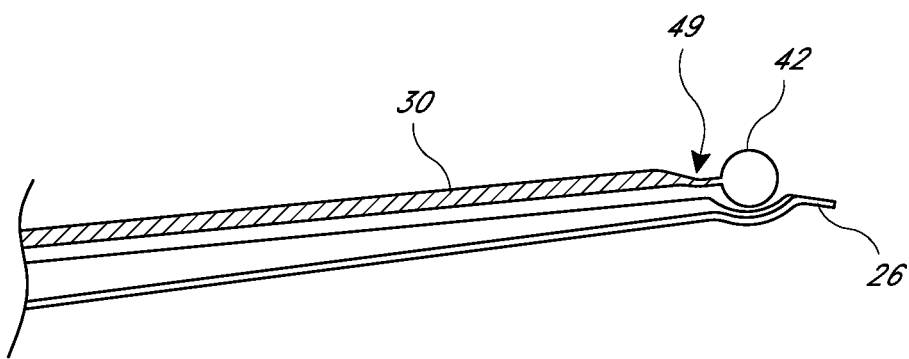
FIG. 9 is a partial cross-sectional view of an embodiment of one of the arms of the basket of FIG. 6 supporting the closable loop along a distal end region of the arm by releasable thermal bond to the film.

Alternatively, as illustrated in FIG. 9, which is a partial cross-sectional view of an embodiment of one of the arms 24 of the basket 28 of FIG. 6 supporting the closable loop 42 along a distal region of the arm 24 by releasable thermal bond 49 to the film 30, the film 30 may extend only as far as the closable loop 42. As discussed above, a releasable adhesive 48 or some form of wax can be used instead of the thermal bond 49. Regardless of the type of bond or positioning of the film 30, the closable loop 42 and the film 30 can be joined such that the bond can break when the closable loop 42 is tightened, allowing the closable loop 42 to release from the basket 28.

Figure 10:
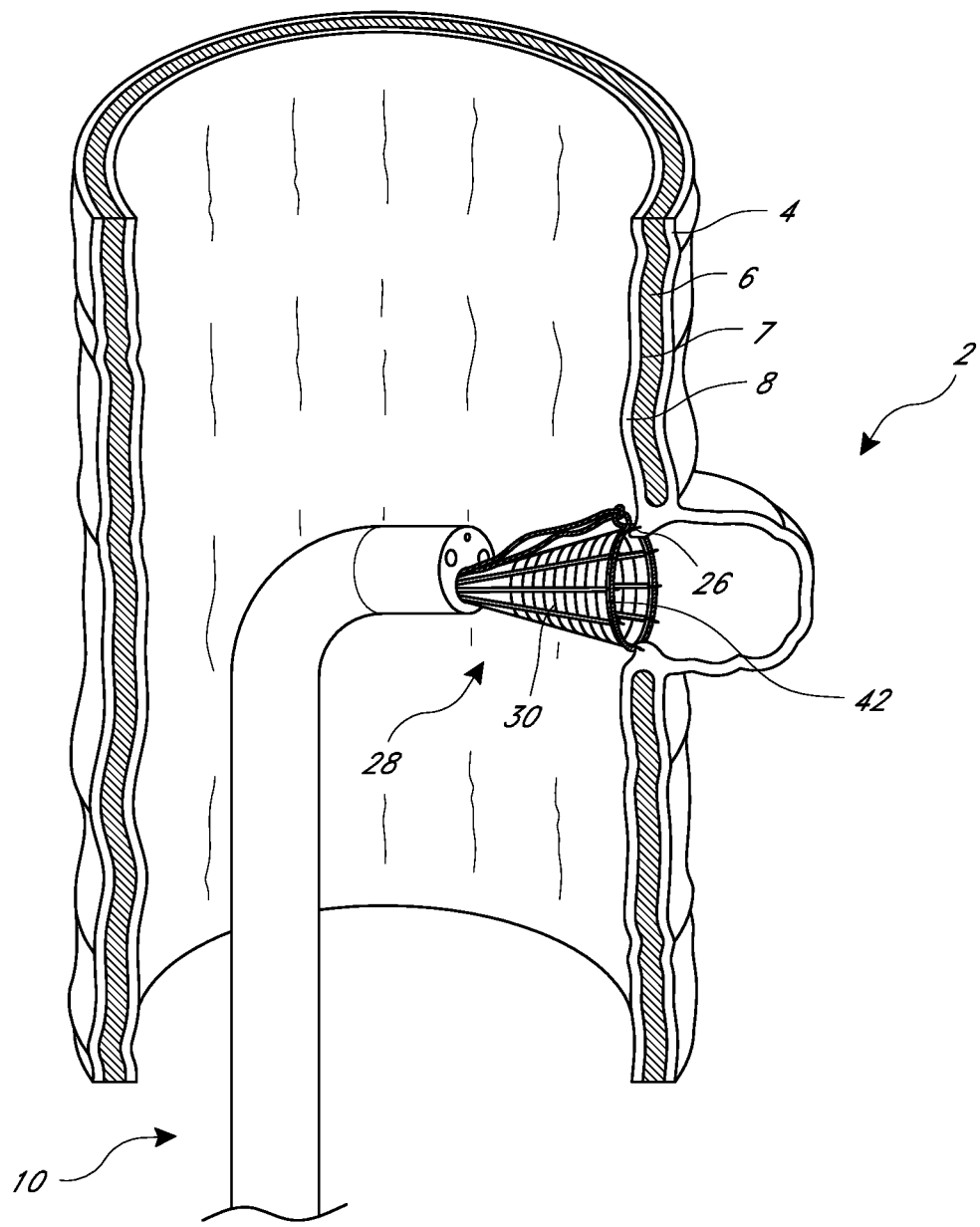
FIG. 10 is a perspective view of an embodiment of the distal rim of the expanded basket of FIG. 6 surrounding the opening to the diverticulum and contacting the lining of the colon, which is shown in cross-section.
Figure 11:
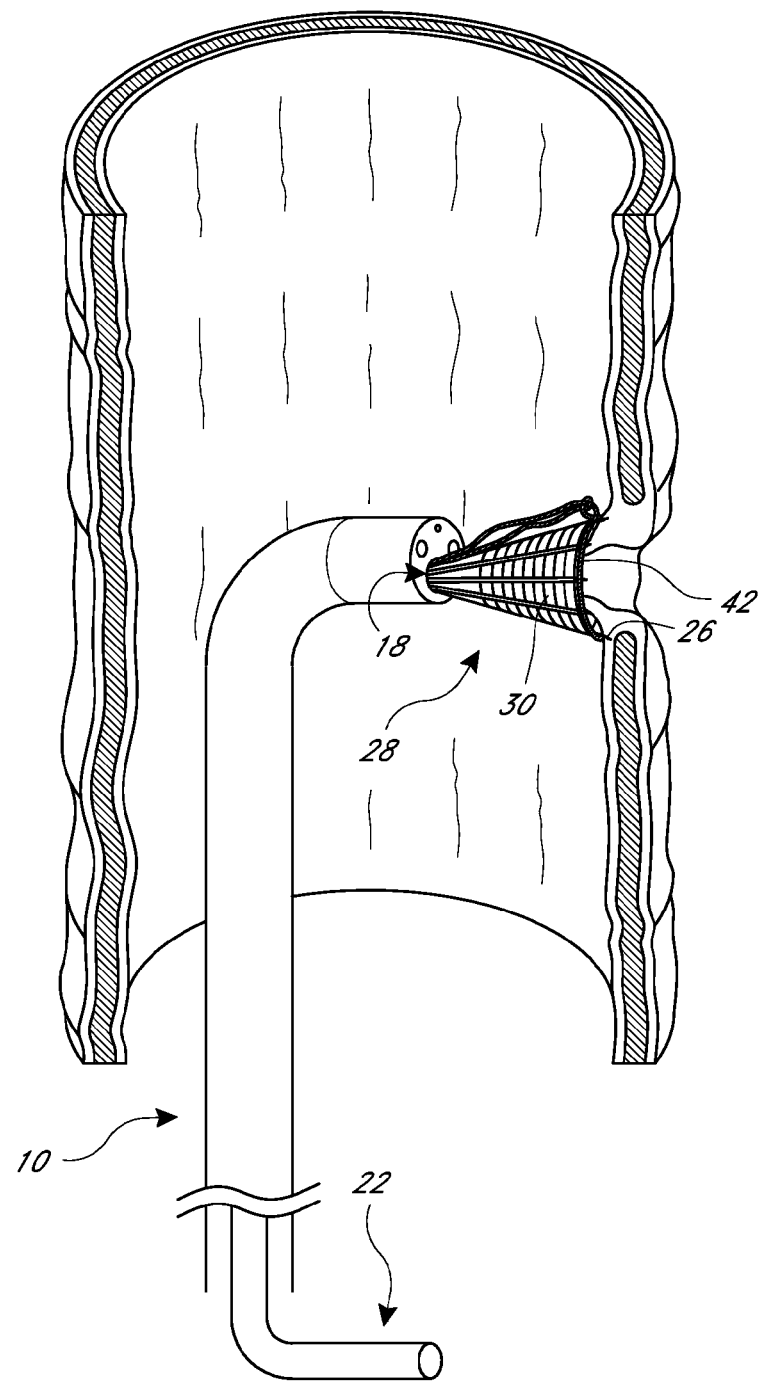
FIG. 11 shows the embodiment of FIG. 10 after a negative pressure has been applied within the basket.
Figure 12:
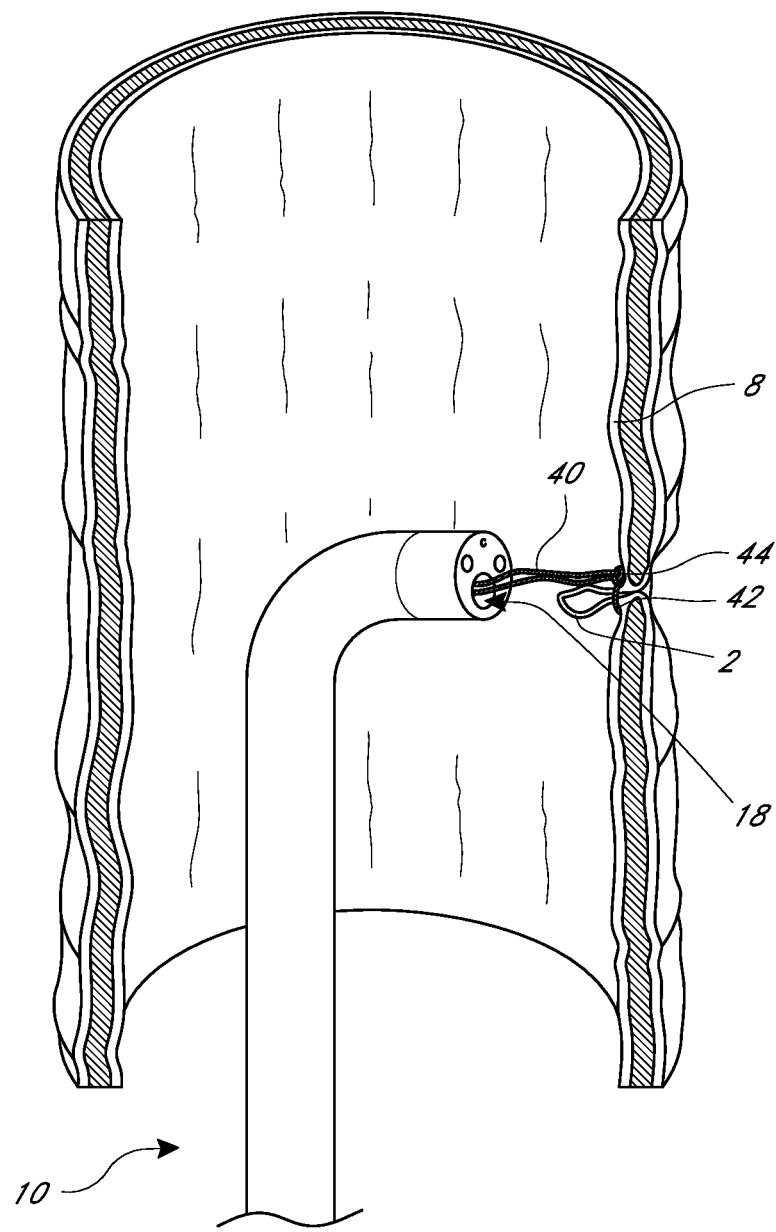
FIG. 12 shows the embodiment of FIG. 11 after the inverted diverticulum has been ensnared by tightening the closable loop.

FIGS. 10-12 illustrate a process for inverting a diverticulum 2 using a diverticulum inverting device. FIG. 10 is a perspective view of an embodiment of the distal rim of the expanded basket 28 of FIG. 6 surrounding the opening to the diverticulum 2 and contacting the lining of the colon, which is shown in cross-section. In FIG. 10, the operator of a colonoscope 10 has identified a diverticulum 2 and pushed the diverticulum inverting device partially outside of the working channel of the colonoscope 10 such that the basket 28 expanded toward its expanded configuration. The colon is generally slightly pressurized at this point in order to make it slightly inflated and easier to examine, although the slight pressurization is not necessary to use the diverticulum inverting device. The distal rim of the basket 28 is then positioned against tissue at the site surrounding an opening to the diverticulum 2, in this case the mucosal layer 8 that lines the inside of the colon. The spikes 26 enter the mucosa 8, and may form a substantially airtight seal between the distal rim of the basket 28 and the tissue, such that minimal fluid communication exists between the interior of the basket 28 and the colon. The spikes 26 can be of a length to engage the tissue of the mucosa 8. The length of the spikes 26 may be long enough to penetrate through the underlying submucosa 7 and into the muscularis 6. The spikes 26 need not be long enough to pass into or through the outer serosal layer 4. Nevertheless, the diverticulum inverting device as described herein is not limited to embodiments where the spikes 26 do not reach the serosa 4.

FIG. 11 shows the embodiment of FIG. 10 after a negative pressure has been applied within the basket 28. In FIG. 11, a negative pressure has been applied to tube 22, which is in fluid communication with the basket 28. Because of the substantially airtight seal created with the tissue along the distal rim of the basket 28, and the substantially airtight seal that exists between the film 30 and the arms 24, the negative pressure draws the diverticulum 2 at least partially into the basket 28. The negative pressure may draw the diverticulum 2 into the basket 28 even if the seals are not perfect, such as if the seal between the film 30 and the arms 24 allows fluid to pass through or if the seal between the distal rim and the tissue allows fluid to pass through. As illustrated in FIG. 11, the diverticulum 2 can be completely inverted into the basket 28.

With the diverticulum 2 inverted, the closable loop 42 can be deployed around the neck, or base, of the diverticulum 2. This can be achieved by tightening the closable loop 42 as the basket 28 is withdrawn back into the working channel 18 of the colonoscope 10 or the colonoscope 10 is advanced over the basket 28, such that the closable loop 42 releases from the basket 28 and ensnares or surrounds the base of the inverted diverticulum 2. The closable loop 42 can begin to be tightened before, after, and/or simultaneously with the basket 28 reentering the working channel 18. Once the closable loop 42 is around the diverticulum 2, the basket 28 can be completely withdrawn into the working channel 18, returning to a collapsed configuration.

Once the closable loop 42 is off of the basket 28, it can be further tightened, as illustrated in FIG. 12. As discussed above, the closable loop 42 can be tightened with a knot pusher 46 or other tightening tool. The closable loop 42 can also be tightened by pulling on one or both ends of suture 40. Once tightened, excess suture 40 beyond the knot 44 can be cut with scissors advanced through the working channel 18, as is known in the art, and then removed through the working channel 18.

The closable loop 42 can be tightened an amount that will create contact between serosa 4 on either side of the diverticulum 2. This will allow the serosa 4 to grow together across the base of the diverticulum 2. Additionally, by joining the serosa 4, the opening in the muscular layer 6 of the colon wall through which a diverticulum 2 is formed will be reduced, which can preclude circulation of blood into the tissue of the diverticulum 2 and cause necrosis of the diverticulum 2. It may be desirable to deflate the colon slightly in order to create contact between the serosa 4. The necrotized diverticulum 2 may slough off while the serosa 4 at the base of diverticulum 2 will begin to adhere to itself and heal. The diverticulum 2 can be removed with a RF snare, cautery wire, blade, or other removal implement, as is known in the art.

FIGS. 13A and 13B are perspective views of an embodiment of a diverticulum inverting device including a closable loop 42 including stops 47 before and after tightening, respectively. As illustrated in FIG. 13A, the stops 47 can be attached to the suture material 40 a pre-determined distance apart along the length of the closable loop 42. As the closable loop 42 is tightened, whether with a knot pusher 46 or by other means, the stops 47 will draw closer to the knot 44. Eventually, the stops 47 will hit the knot 44, as shown in FIG. 13B, preventing the closable loop 42 from tightening further. The closable loop 42 at this point will have a length approximately equal to the pre-determined distance between the two stops 47, for example plus any size added by the knot 44 between the stops 47. For tightening around diverticula 2, the stops 47 can be placed a distance apart such that the tightened loop 42 has a length of about 6 millimeters to about 12 millimeters (e.g., a diameter of about 2 millimeters to about 4 millimeters), although longer and shorter lengths can also be used. For example, the stops 47 can be placed to define a closable loop 42 with a tightened length of about 3 millimeters to about 9 millimeters, less than about 6 millimeters, or less than about 3 millimeters. Alternatively, the closable loop 42 can have a tightened length of about 9 millimeters to about 18 millimeters or of greater than about 18 millimeters.

Figure 14:
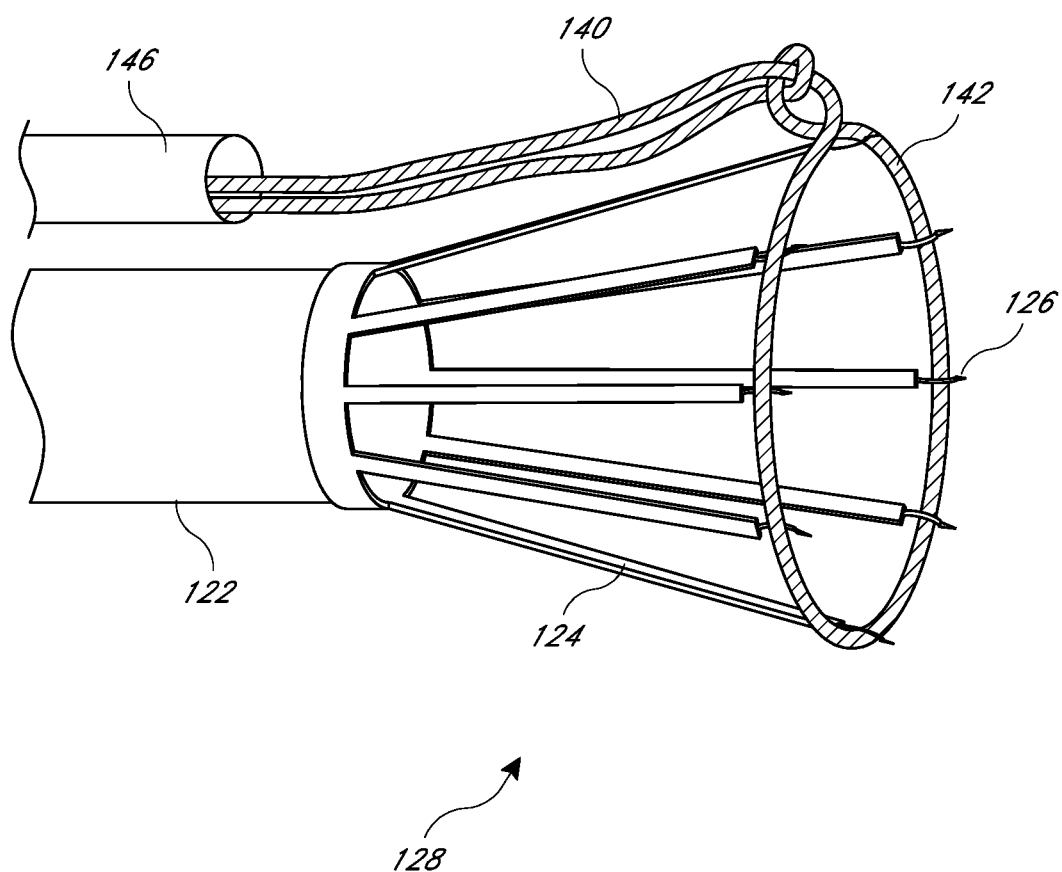
FIG. 14 is a perspective view of another embodiment of a diverticulum inverting device including a basket without a film attached to the arms of the basket.

FIG. 14 is a perspective view of another embodiment of a diverticulum inverting device including a basket 128 without a film attached to the arms 124 of the basket 128. One advantage of such an embodiment is that the basket 128 can be made smaller and cheaper than would otherwise be possible. The diverticulum inverting device can otherwise be structured the same as or substantially similar to the embodiments discussed above. For example, the distal ends of arms 124 can still have spikes 126 and still define a distal rim that supports a closable loop 142. The excess loop material 140 can run through the working channel 18 of the colonoscope or 10 through the tube 122. Where no film is attached to the arms 124, the tube 122 can include a solid, flexible cylinder. As described above, if a knot pusher 146 is used, the loop material 140 can pass through the knot pusher 146.

Where the arms 124 of the basket 128 are not attached to a film, the closable loop 142 can be bonded directly to the arms 124 of the basket 128. As discussed above, this can be done with a releasable adhesive, some form of wax, or other releasable bonding substance. The closable loop 142 can be bonded to the basket 128 on a portion of the spikes 126, at the base of the spikes 126, or on more proximal portions of the arms 124.

The basket 128 can be pushed through the working channel 18 of a colonoscope 10, and, upon exiting or beginning to exit the working channel 18, the basket 128 will tend toward its expanded position. The basket 128 can then be positioned against tissue at the site surrounding an opening to the diverticulum 2, as discussed above. Once the basket 128 is positioned, the diverticulum 2 can be inverted by applying a negative pressure, also as discussed above. However, in this embodiment, because without the film a substantially airtight seal does not exist between the interior and the exterior of the basket 128, the negative pressure can be applied to the entire colon and not just the interior of the basket 128. The negative pressure can be applied through the tube 122 or can be applied through other lumens of the colonoscope, such as the lumen 16, illustrated in FIG. 2.

Figure 15:
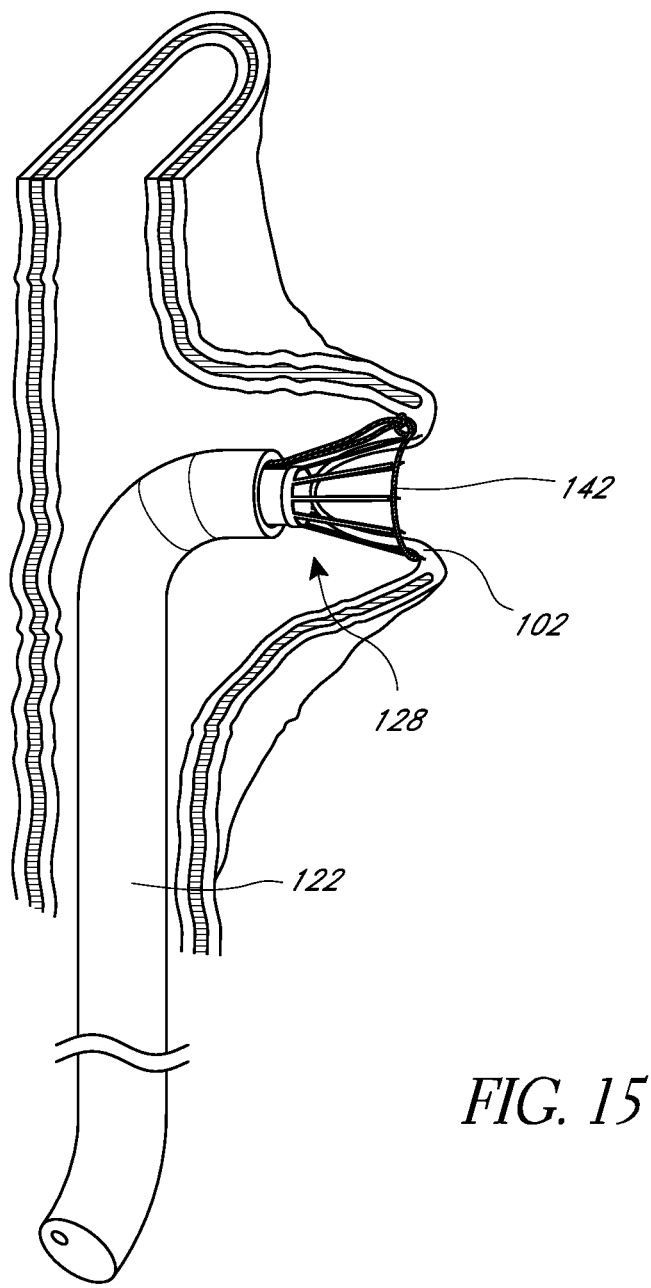
FIG. 15 is a perspective and cross-sectional view of application of a negative pressure within the colon causing inversion of a diverticulum into an expanded basket.

FIG. 15 is a perspective and cross-sectional view of application of a negative pressure within the colon causing inversion of a diverticulum 102 into an expanded basket 128. As illustrated in FIG. 15, the colon has deflated, the diverticulum 102 has inverted into the basket 128, and the diverticulum 102 is positioned within the closable loop 142 on the distal rim of the basket. The basket 128 can then be removed and the closable loop 142 tightened around the diverticulum 102, as described above.

It can be beneficial to at least partially reflate the colon before removing the basket 128 and tightening the closable loop 142. Alternatively, the colon may be at least partially reflated after removing the basket 128 but before fully tightening the closable loop 142. The colon can be reflated by applying pressure through a lumen of a colonoscope or a separate device. Additionally, in certain situations, the basket 128 can be positioned around a diverticulum 102 after the negative pressure has been applied and the diverticulum 102 has inverted. This process can be beneficial where applying negative pressure inverts multiple diverticula 102 at the same time.

Figure 16:
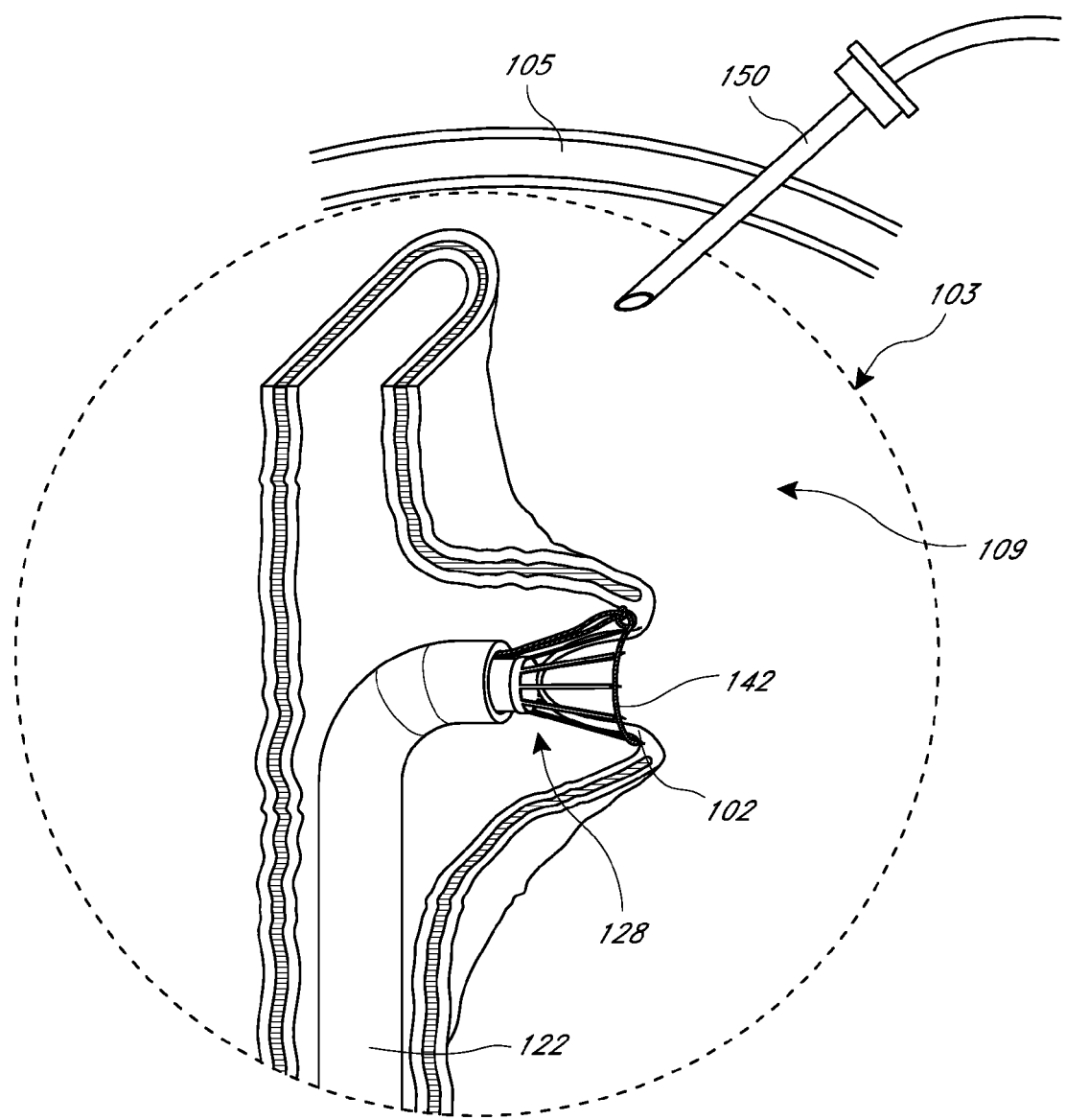
FIG. 16 is a perspective and cross-sectional view of application of a positive pressure within the peritoneal cavity causing inversion of the diverticulum into an expanded basket.

Diverticula 102 can also be inverted by applying a positive pressure outside of the colon, instead of applying a negative pressure within the colon. Applying positive pressure outside of the colon can be done where the basket 128 has a film attached to it and where the basket 128 does not have a film attached to it. FIG. 16 is a perspective and cross-sectional view of application of a positive pressure within the peritoneal cavity causing inversion of the diverticulum 2 into an expanded basket 128. As illustrated in FIG. 16, a positive pressure device 150 is inserted into a patient, through the abdominal wall 105, through the peritoneum 103, and into the peritoneal cavity 109. The positive pressure device 150 can be a needle connected to a source of pressure, a trocar, or any other instrument capable of penetrating the peritoneal cavity 109 and delivering a positive pressure. The positive pressure can be delivered in the form of air, $CO_2$, or any other gas or fluid. As with the embodiments discussed above relating to application of negative pressure within the entire colon, positive pressure can be applied to the peritoneal cavity 109 with a basket 128 already positioned against mucosal tissue 8 at the site surrounding an opening to a diverticulum 102. Similarly, the basket 128 can also be positioned around a diverticulum 102 that has already inverted by the positive pressure.

One advantage of applying positive pressure to the peritoneal cavity 109 or of applying negative pressure to the entire colon is that the basket 128 does not need to be sealed tightly against the tissue at the site surrounding an opening to the diverticulum 102. Additionally, applying pressure in this manner can improve the speed of the procedure if applying pressure causes multiple diverticula 102 to invert.

With reference to FIGS. 17-38D, instead of using a closable loop 42, 142 to ensnare and tie off an inverted diverticulum 2, 102, the device includes a closure clip placed over an inverted diverticulum 202. The closure clip may close around and compress the diverticulum 202, allowing tissue at the base of the diverticulum 202 to adhere to itself and heal while causing necrosis in the tissue of the diverticulum 202 itself—much as described above with regard to tying off the diverticulum 2, 102. The closure clip can allow the serosa 4 to adhere to and heal itself, while allowing the mucosa 8 at the base of the diverticulum 202 to necrose. The closure clip can be employed where the diverticulum inverting device includes a film attached to arms of a basket, where the diverticulum inverting device does not have a film attached to arms of a basket, where the diverticulum inverting device includes a temporary basket, where the diverticulum inverting device includes a detachable basket, where the diverticulum inverting device uses negative pressure applied within the colon or basket, and/or where the diverticulum inverting device uses positive pressure applied in the peritoneal cavity, all discussed above.

The general structure of a device, described in more detail below, may include a delivery sheath configured to slide coaxially over the basket and over the tube connected to the basket. A clip and a pusher tube can be coaxially and slidably positioned around the delivery sheath, and the clip may be positioned distal to the pusher tube. When a diverticulum has been inverted into the basket, the delivery sheath can be positioned around the basket. The pusher tube can then be used to push the clip to a portion of the delivery sheath that is around the basket. The pusher tube can push the clip off of the delivery sheath, or retain the clip in position while the delivery sheath and basket are retracted, or while just the delivery sheath is retracted, leaving the clip around the diverticulum.

Figure 17:
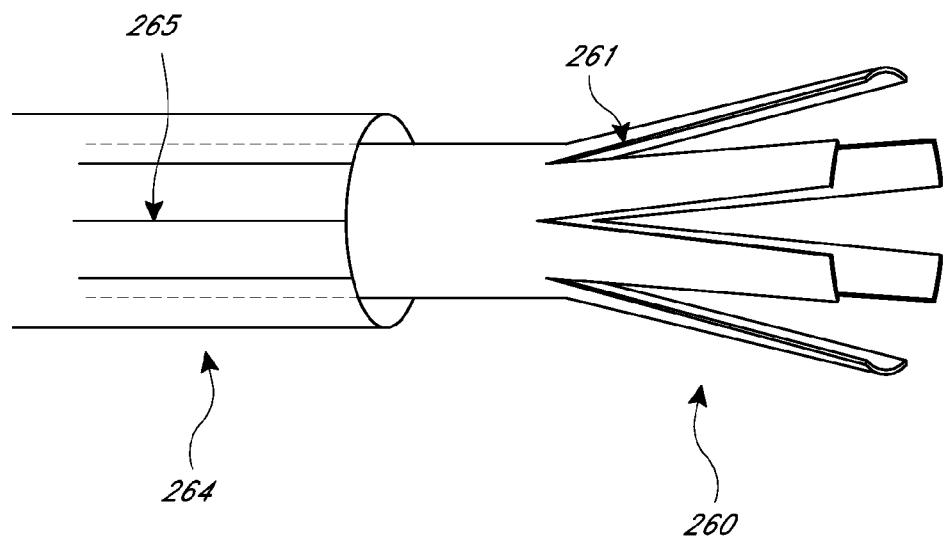
FIG. 17 is a perspective view of a device including an expandable delivery sheath extending from and coaxially engaged within a pusher tube.

FIG. 17 is a perspective view of a device including an expandable delivery sheath 260 extending from and coaxially engaged with a pusher tube 264. The delivery sheath 260 can include a plurality of slits 261 extending proximally from its distal end. The slits 261 are configured to allow the delivery sheath 260 to expand as needed to slide over a basket. A delivery sheath 260 without slits, for example including an expandable material, is also possible. The pusher tube 264 is positioned coaxially around the delivery sheath 260, and also may include slits 265 that allow the pusher tube 264 to expand as needed to slide over a portion of the delivery sheath 260 when the delivery sheath 260 is around a basket.

Figure 18:
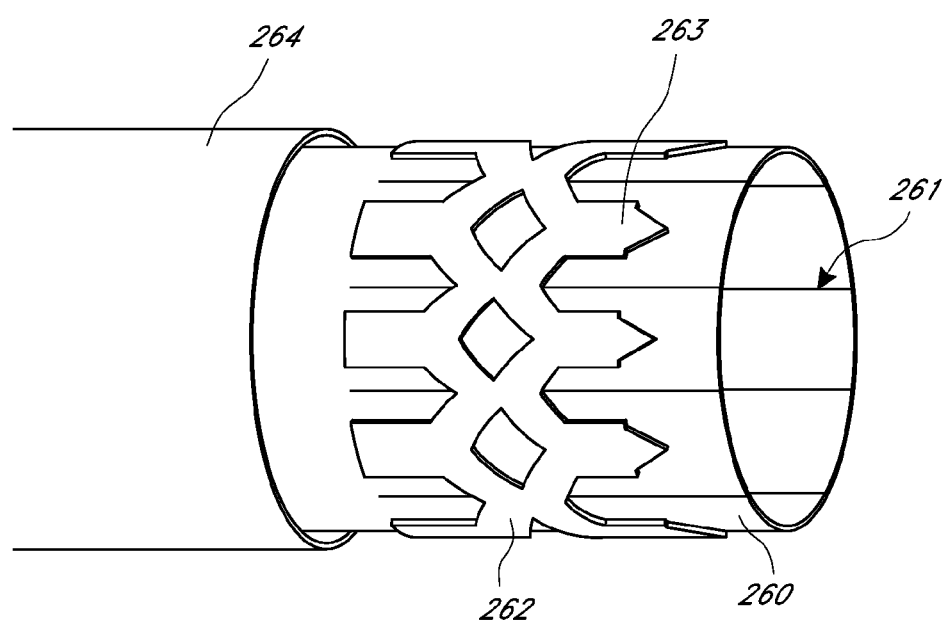
FIG. 18 is a perspective view of a closure clip coaxially arranged over the expandable delivery sheath of FIG. 17.

FIG. 18 is a perspective view of a closure clip 262 coaxially arranged over the delivery sheath 260. The pusher tube 264 is around the delivery sheath 260. The clip 262 can include a distal portion including teeth 263. As the pusher tube 264 is moved toward the distal end of the delivery sheath 260, the pusher tube 264 pushes the clip 262 until the clip 262 falls off of the distal end of the delivery sheath 260. The clip 262 may be expandable so that it can fit over and be pushed off the distal end of the delivery sheath 260 even when the delivery sheath 260 has expanded over a basket. Additionally, the clip 262 may include, for example, a SMA material, such that when the clip 262 releases from the delivery sheath 260, the clip 262 can return to an initial compacted shape.

FIGS. 19-22 illustrate an example clip in more detail. FIG. 19 is a cross-sectional view of a closure clip 262 showing radially inward orientation of tissue-engaging teeth 263. The clip 262 has been heat set or the like such that the teeth 263 angle radially inward when the clip 262 is in an expanded shape. FIG. 20 is a perspective view of the closure clip 262 showing radially inward orientation of tissue-engaging teeth 263, for example because a delivery sheath or the like does not cause the teeth 263 to extend along the longitudinal axis of the clip 262.

FIG. 21 is a projected side view of the closure clip in a compressed state. For example FIG. 21 is an example of how the closure clip 262 may look when positioned around the delivery sheath 260, which prevents the teeth 263 from angling inward. The clip 262 can include cuts or slits 266 that allow the clip 262 to expand. The clip 262 can include combinations of a single central slit 266 that does not reach an edge of the clip 262 and pairs of slits 267, each slit 267 of the pairs of slits extending toward the other slit 267 of the pairs of slits from opposite sides of the clip 262. Each slit 267 of the pairs of slits can be substantially straight (e.g., does not have portions that vary by more than about 10 degrees from either end of a perfectly straight slit 267). Each slit 267 of the pairs of slits can also be substantially parallel to the longitudinal axis of the generally tubular body (e.g., does not vary by more than about 10 degrees from the longitudinal axis). As illustrated in FIG. 21, the clip 262 can include central slits 266 and pairs of slits 267 that alternate around the diameter of the clip 262. Alternatively, the clip 262 can include any other configuration, formation, combination, or design of slits that would allow the clip 262 to expand. FIG. 22 is a projected side view of the closure clip 262 in an expanded state, and illustrates how the slits 266, 267 can allow the clip 262 to expand, for example by widening to form apertures.

Figure 23:
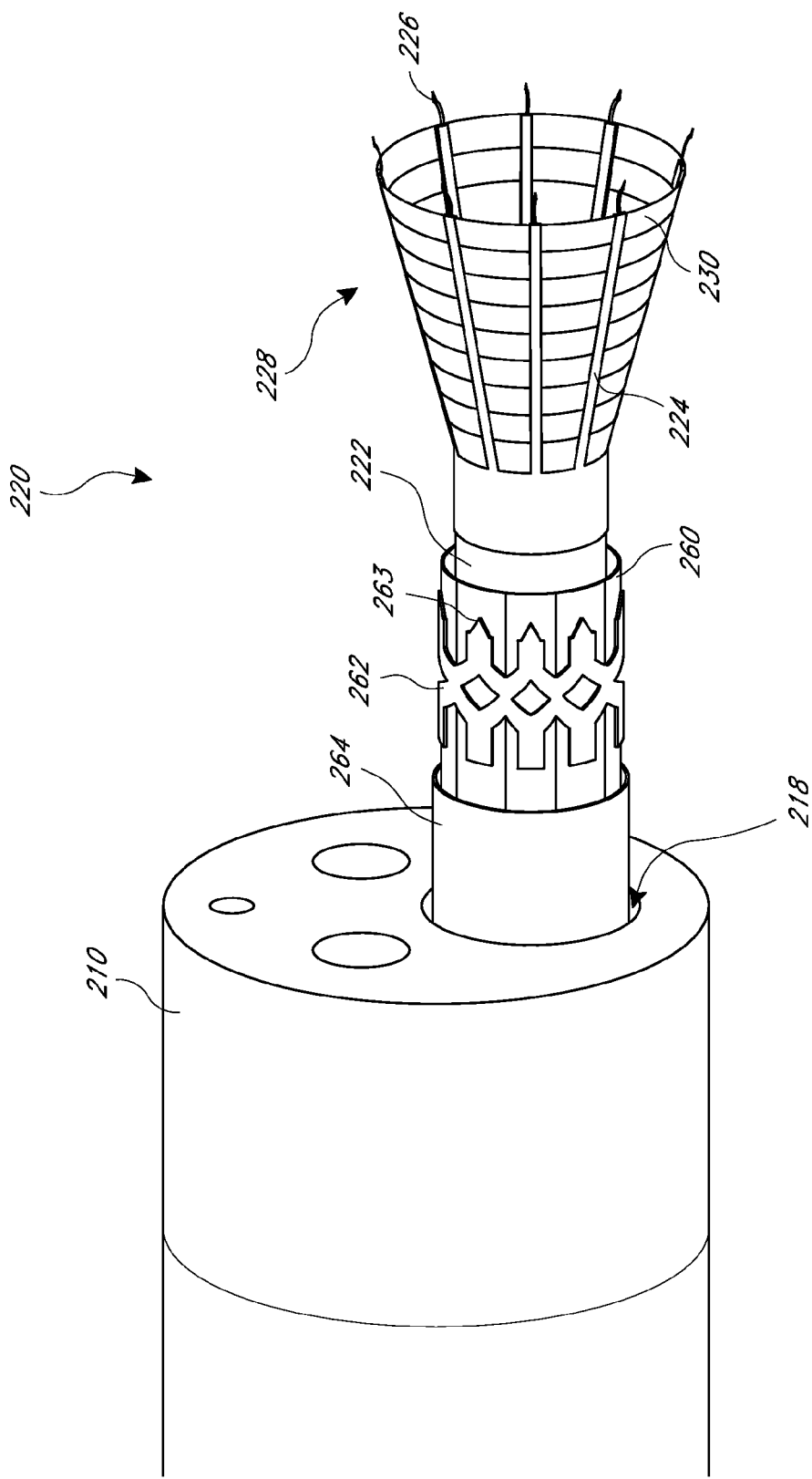
FIG. 23 is a perspective view of a device extending distally from the working channel of a colonoscope, the device including an expanded basket including a film of material, a delivery sheath, and a closure clip.

FIG. 23 is a perspective view of a device extending distally from the working channel 218 of a colonoscope 210, the device including an expandable basket 228 including a film 230 of material, a delivery sheath 260, and a closure clip 262. As illustrated in FIG. 23, the tube 222, the basket 228, the delivery sheath 260, the closure clip 262, and the pusher tube 264 have all been deployed through the working channel 218 of a colonoscope 210. As discussed above, because the diverticulum inverting device 220 can fit through the working channel 218, when a physician discovers a diverticulum during a colonoscopy, the physician can keep the colonoscope 210 in the colon and focused on the diverticulum, and advance the device through the working channel 218 of the colonoscope 210 in order to treat the diverticulum at that time.

Figure 24A:
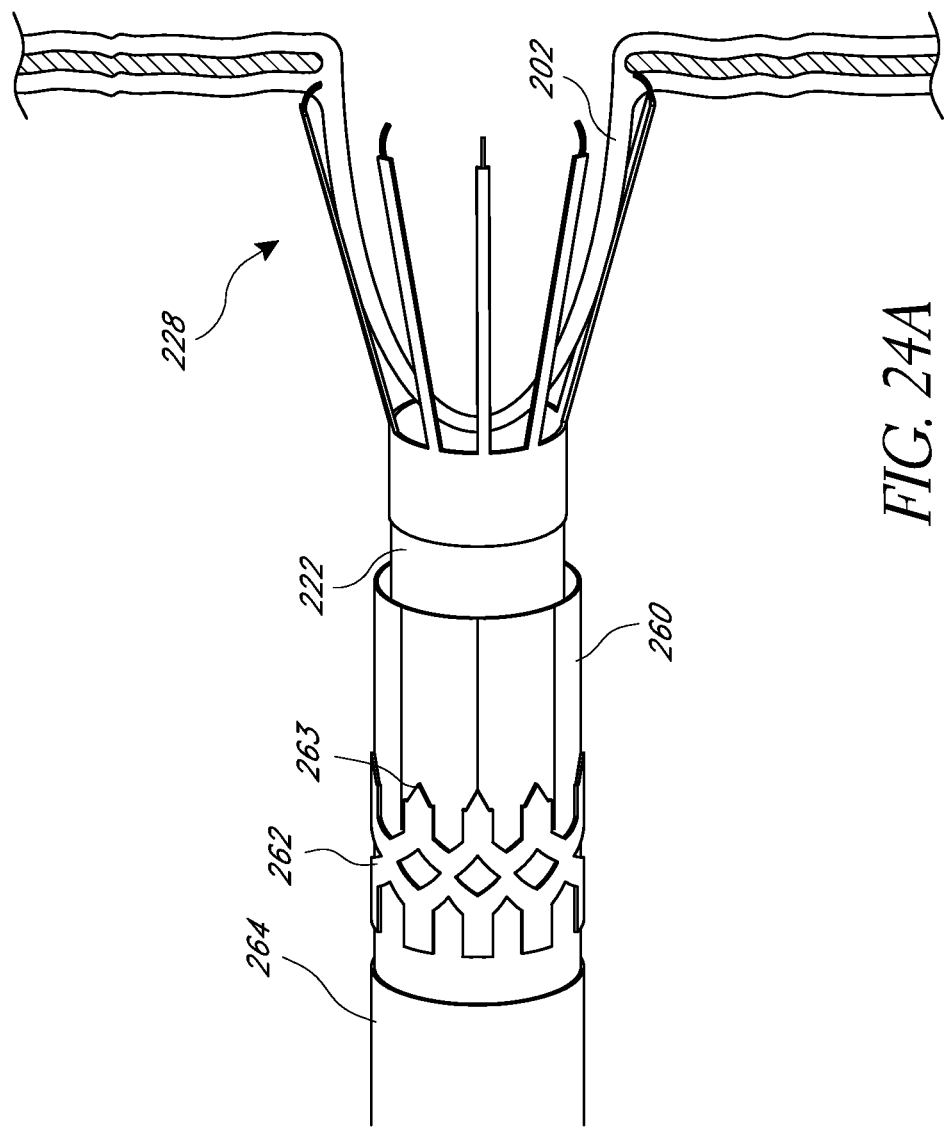
FIGS. 24A-24D schematically illustrate a method including, respectively, (A) contacting the lining of the colon around a site of an opening to a diverticulum with the distal rim of an expanded basket and inverting the diverticulum into the basket; (B) advancing an expandable delivery sheath including a closure clip distally over the expanded basket; (C) further advancing the closure clip and a pusher tube distally over the expanded basket, the closure clip over the distal rim of the basket; and (D) deploying the clip around the neck of the inverted diverticulum by pushing the clip off of the delivery sheath using the pusher tube, and withdrawing the basket.

FIGS. 24A-24D schematically illustrate a method by which the closure clip 262 can be deployed over an inverted diverticulum 202. In FIG. 24A, the diverticulum 202 has been inverted according to any of the methods discussed above and the basket 228 has been positioned around the tissue at the base of a diverticulum 202, the inverted diverticulum 202 at least partially within the basket 228. The delivery sheath 260 is not around the basket 228, the clip 262 is over the delivery sheath 260, and the pusher tube 264 is proximal to the delivery sheath 260. The basket 228 may include a film 230, as in the diverticulum inverting device 220, or not, as described above.

Figure 24B:
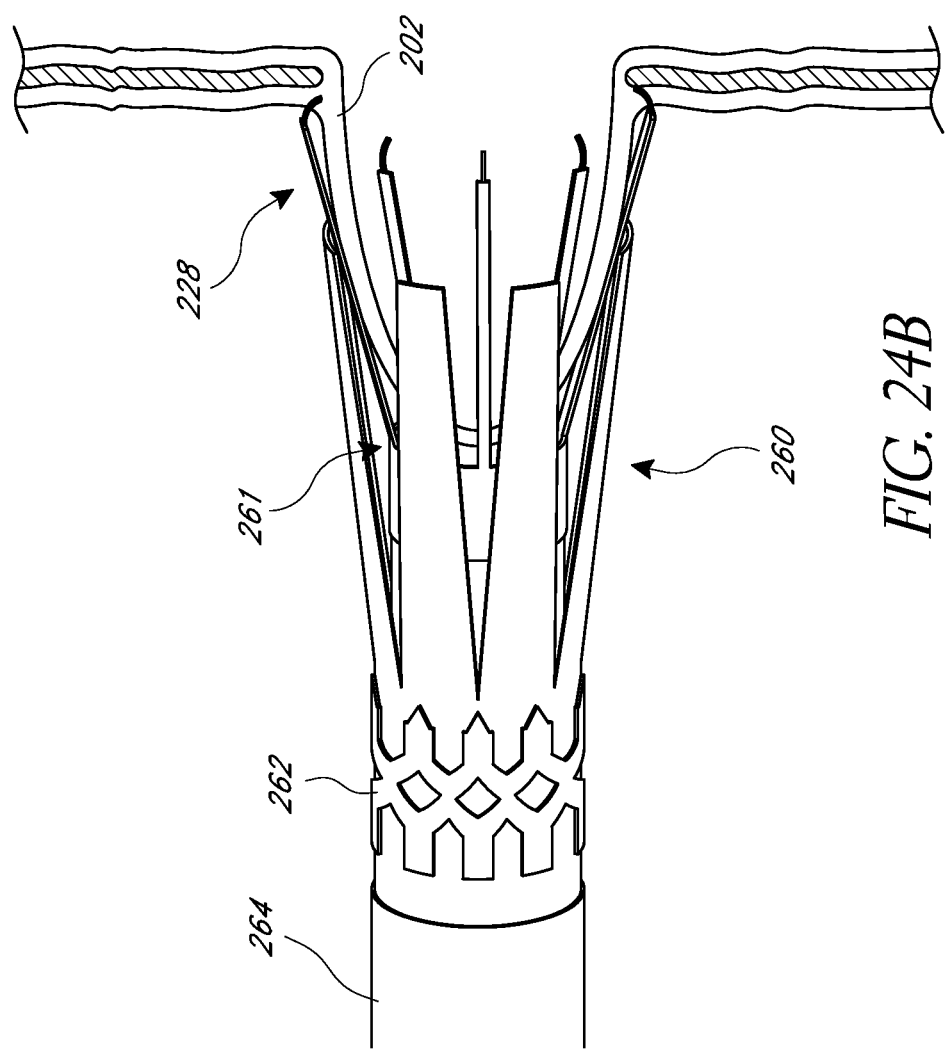

In FIG. 24B, the delivery sheath 260 has been pushed toward the basket 228. As the delivery sheath 260 reaches the basket 228, the slits 261 in the delivery sheath 260 spread apart, allowing the delivery sheath 260 to expand as it progresses over the basket 228. The slits 261 can be longer than, as long as, or shorter than the length of the basket 228. As the delivery sheath 260 distally advances, the portions between the slits 261 create a compressive force on the basket 228 and on the inverted diverticulum 202 at least partially within the basket 228, which causes the basket 228 and the inverted diverticulum 202 to at least partially collapse. Although the delivery sheath 260 can advance to the base of the diverticulum 202, it need not advance all the way. For example, the delivery sheath 260 can advance far enough to compress the basket 228 and the diverticulum 202 sufficiently to allow the clip 262 to fit over the basket 228 and the diverticulum 202.

Figure 24C:
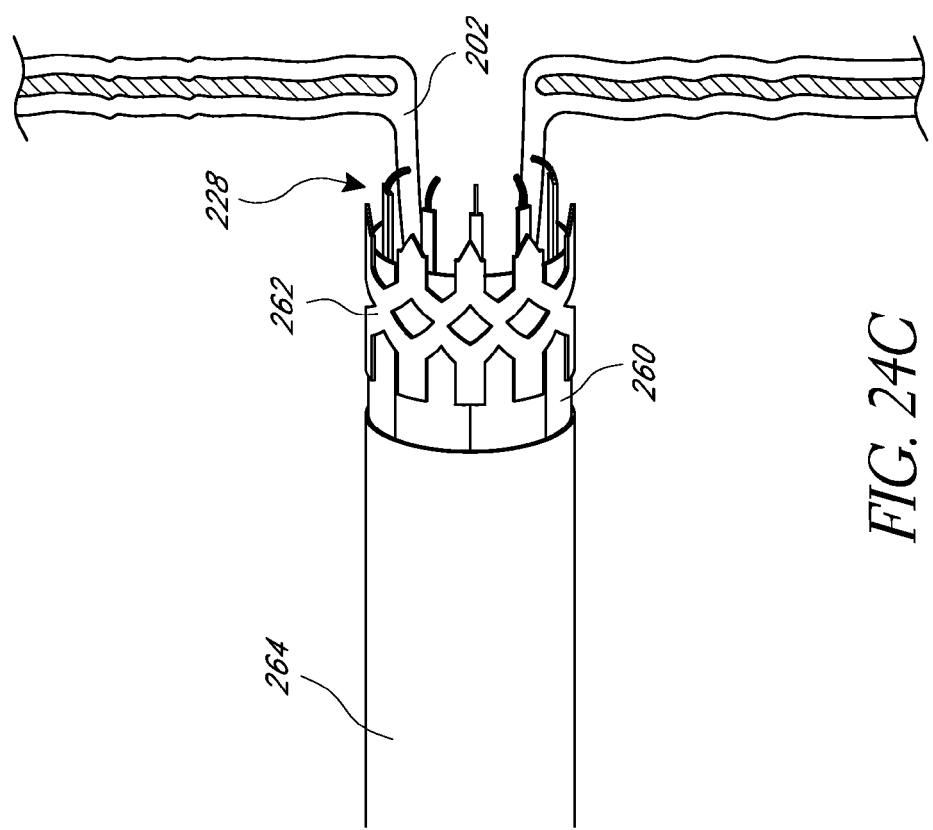

In FIG. 24C, the pusher tube 264 has pushed the clip 262 toward the distal end of the delivery sheath 260, which is around the basket 228 and the diverticulum 202. As illustrated in FIG. 24C, for example by the apertures in the clip 262, the clip 262 has expanded to fit around the basket 228 and the diverticulum 202. Although the pusher tube 264 has not expanded, it can includes slits that allow the pusher tube 264 to expand around the delivery sheath 260, for example like the delivery sheath 260 includes slits 261 that allow the delivery sheath 260 to expand around the basket 228, and/or the pusher tube can include material that is radially expandable. The pusher tube 264 may be smaller, the basket 228 may be larger, and/or the diverticulum 202 may be more resistant to compression such that the pusher tube 264 will need to expand in order to be able to push the clip 262 to the distal end of the delivery sheath 260 and around the basket 228 and the diverticulum 202.

Figure 24D:
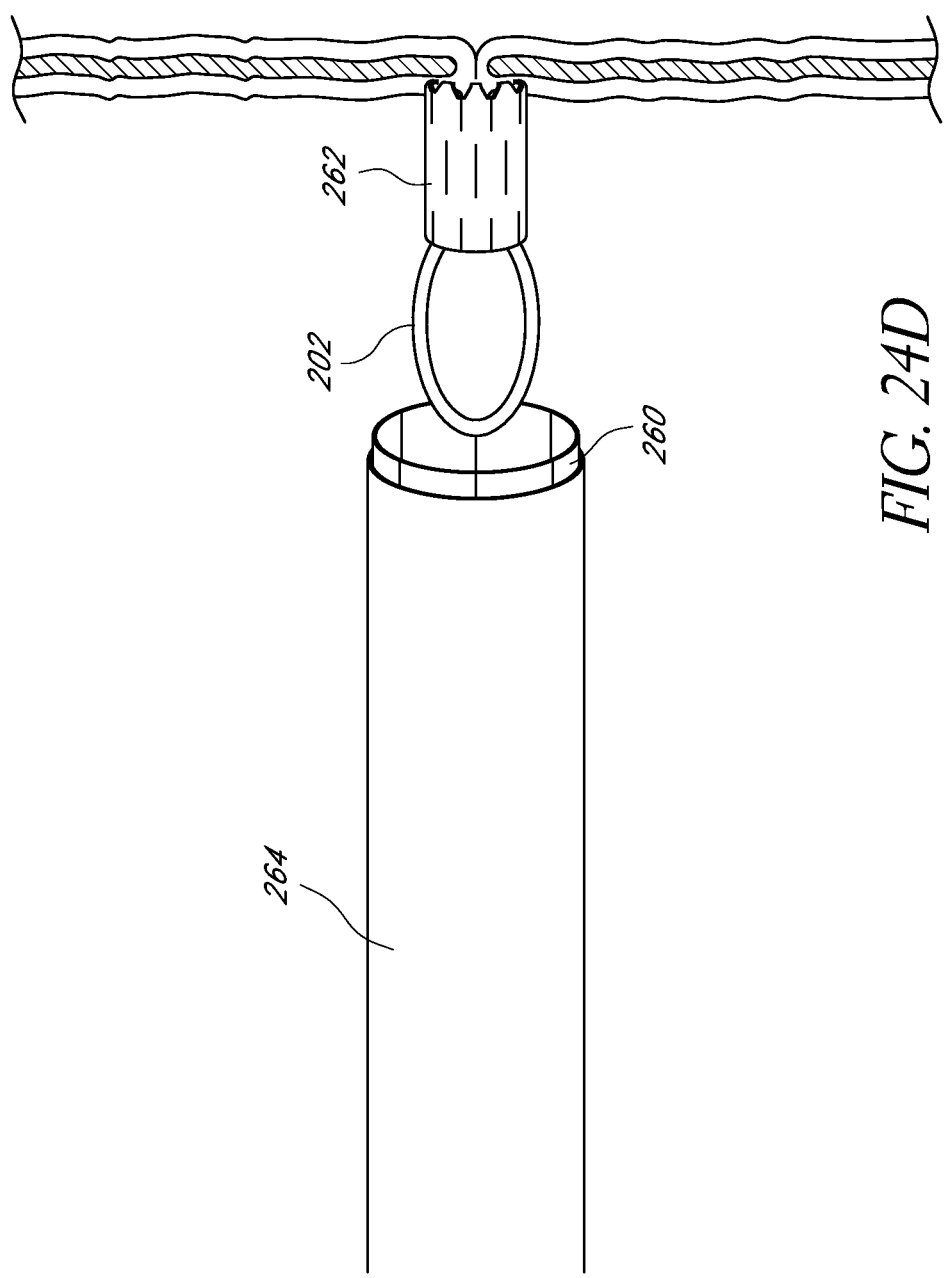

In FIG. 24D, the basket 228 has been withdrawn, the delivery sheath 260 and the pusher tube 264 are partially withdrawn, and the clip 262 is around the diverticulum 202. Starting from the positions of FIG. 24C, placement of the clip 262 may include: withdrawing the basket 228, withdrawing the delivery sheath 260 while holding the clip 262 in position with the pusher tube 264 until the clip is around the diverticulum 202, and then removing the pusher tube 264. However, other orders of operation and timing of movements can be used. For example, the delivery sheath 260 and basket 228 can be partially withdrawn, and then the pusher tube 264 can be advanced to physically push the clip 262 off of the delivery sheath 260 and onto the diverticulum 202. Generally, the procedure can be thought of as "pushing" the clip 262 off of the delivery sheath 260 and onto the diverticulum 202, where "pushing" describes any relative movement of the components where the clip 262 is ultimately around the diverticulum 202 and the basket 228, the delivery sheath 260, and the pusher tube 264 have all been withdrawn from around the diverticulum 202.

Figure 25:
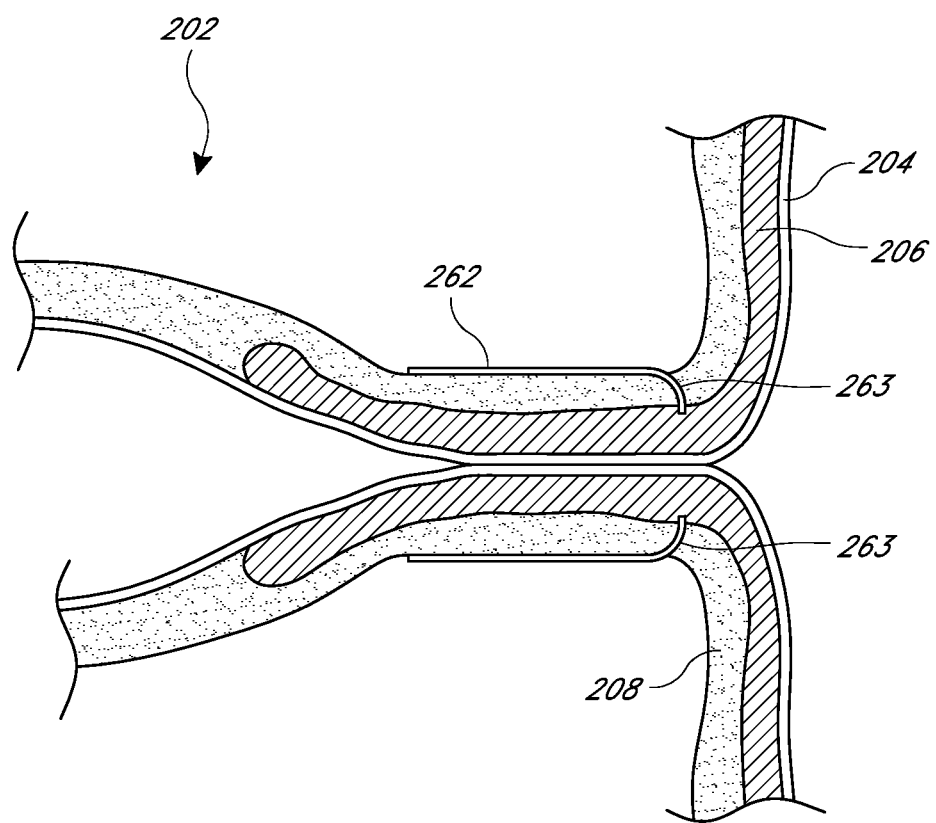
FIG. 25 is a cross-sectional view of a closure clip deployed around the neck of an inverted diverticulum.

Once released from its position around the delivery sheath 260, the clip 262 can return to its initial shape. This shape can have a smaller diameter than when the clip 262 is around the delivery sheath 260. Additionally, in the initial shape, the teeth 263 can turn radially inward, as discussed above. FIG. 25 is a cross-sectional view of a closure clip 262 deployed around the neck of an inverted diverticulum 202. As illustrated in FIG. 25, the clip 262 can compress the diverticulum 202 and the teeth 263 can engage with the tissue of the diverticulum 202. As illustrated in FIG. 25, the teeth 263 extend past the mucosa 208 and slightly into the muscularis 206. Alternatively, the teeth 263 can be sized to extend no further than the mucosa 208 or to extend further into or through the muscularis 206. The teeth can help maintain the serosa 204 in contact, promoting healing and growth that will close the serosa 204.

The initial shape of the clip 262 and size of the teeth 263 can be adjusted or selected prior to use, and they may be of a size that puts opposing layers of serosa 204 in contact when the clip 262 is placed around a diverticulum 202. It may also be beneficial to lower the colon pressure in order to assure contact between the layers of serosa 204 at the mouth of the diverticulum 202. The clip 262 remains in place once the diverticulum inverting device 220 is completely withdrawn, and the layers of serosa 204 can join together while the diverticulum 202 is allowed to necrose and slough off. The clip 262 may slough off with the necrosed diverticulum 202 and pass through the body. Alternatively, the clipped diverticulum 202 can be removed with a RF snare, cautery wire, blade, or other removal implement, as is known in the art. Removing the clipped diverticulum 202 can be done after the serosa 204 has grown and closed the opening to the diverticulum 202. Once removed, the diverticulum 202 and the clip 262 can be collected and removed from the colon, or can be allowed to pass.

Figure 26:
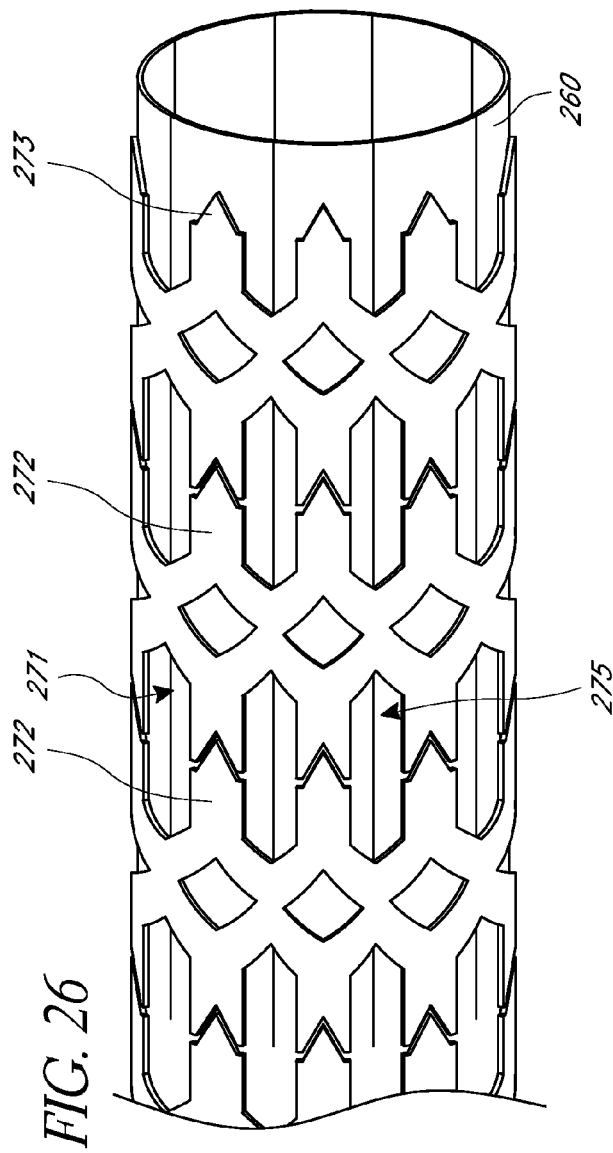
FIG. 26 is a side elevational view of a plurality of expanded closure clips.

FIG. 26 is a side elevational view of a plurality of expanded closure clips 272. The closure clips 272 are arranged end-to-end on a delivery sheath 260. The clips 272 may include SMA such as nitinol. The clips 272 include a distal portion including tissue-engaging teeth 273, for example similar to the tissue-engaging teeth 263 of the clip 262. The clips 272 also includes a proximal portion including recesses 271. The recesses 271 are configured to fit into, be complementary with, nest in, or otherwise engage the teeth 273 of a clip 272 proximal thereto. The proximal region of the clip 272 may include apertures 275 so that the teeth 273 of a clip 272 proximal thereto extend into the apertures 275, which may allow more clips 272 to be stacked, but may reduce flexibility.

Figure 27:
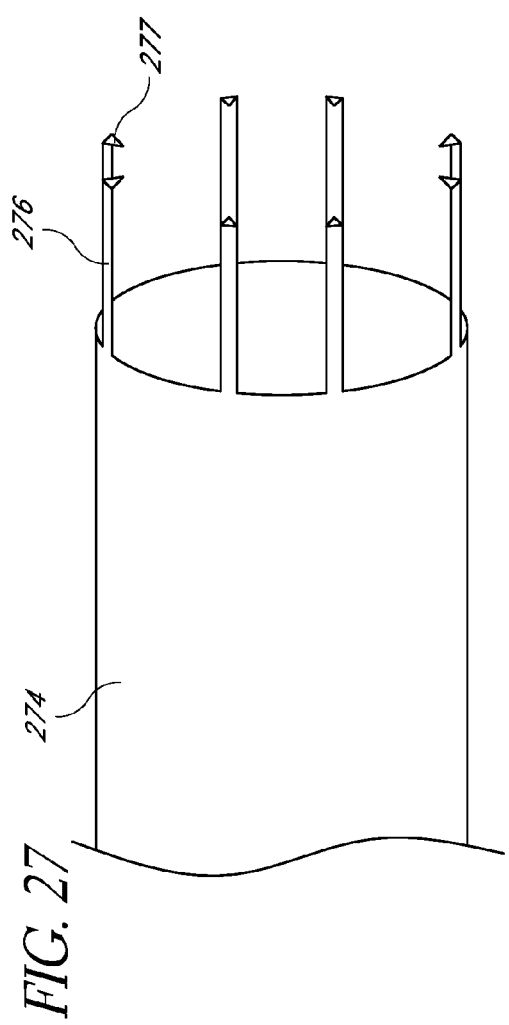
FIG. 27 is a perspective view of a closure clip advancing tool.
Figure 28:
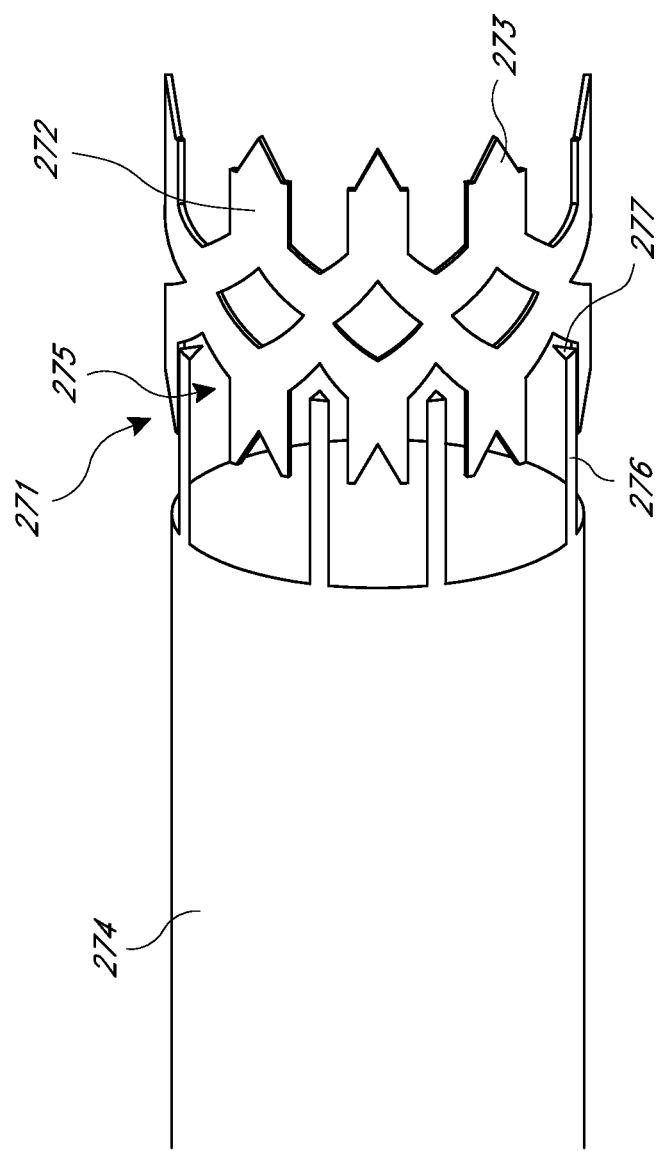
FIG. 28 is a perspective view of the advancing tool of FIG. 27 engaged with one of the closure clips of FIG. 26.

FIG. 27 is a perspective view of a closure clip advancing tool 274. The tool 274 includes a proximal portion and a plurality of distally-extending fingers 276. The fingers 276 may include teeth 277 to provide a larger surface for engaging the clips 272. FIG. 28 is a perspective view of the advancing tool 274 engaged with a closure clip 272. The tips of the fingers 276 of the tool 274 engage a clip 272 at edges of apertures 275. The clips 272 may be around the advancing tool 274, in which case the teeth 277 may extend radially outward, or the advancing tool 274 may be around the clips 272, in which case the teeth 277 may extend radially inward. As the tool 274 is distally advanced, the clip 272 is distally advanced, similar to the interaction between the pusher 264 and the clip 262 described above. The teeth 277 may point at least partially distally, allowing them to push clips 272 distally, but to slide over or through clips 272 if retracted proximally.

Figure 29:
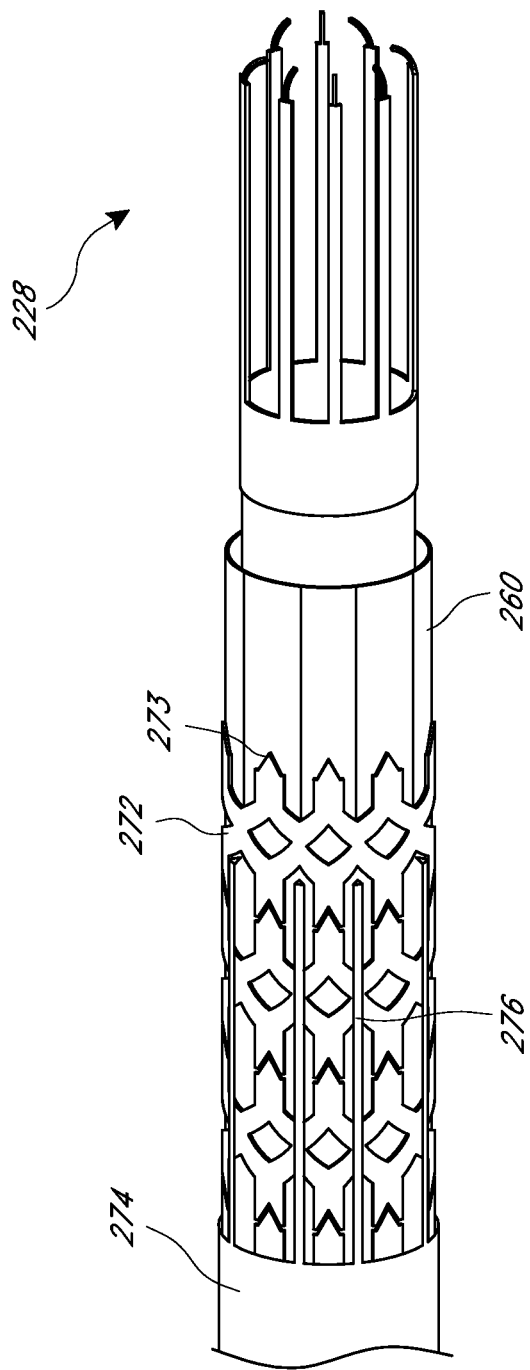
FIG. 29 is a perspective view of the plurality of closure clips of FIG. 26 coaxially arranged over an expandable delivery sheath and the advancing tool of FIG. 27 engaged with one of the closure clips.

FIG. 29 is a perspective view of the plurality of closure clips 272 coaxially arranged over an expandable delivery sheath 260 and the advancing tool 274 engaged with one of the closure clips 272. The tool 274 is initially engaged with the distal-most clip 272. As described above, a basket 228 extends through the delivery sheath 260, and all of the components illustrated in FIG. 29 may extend out of a working lumen of a colonoscope.

Figure 30:
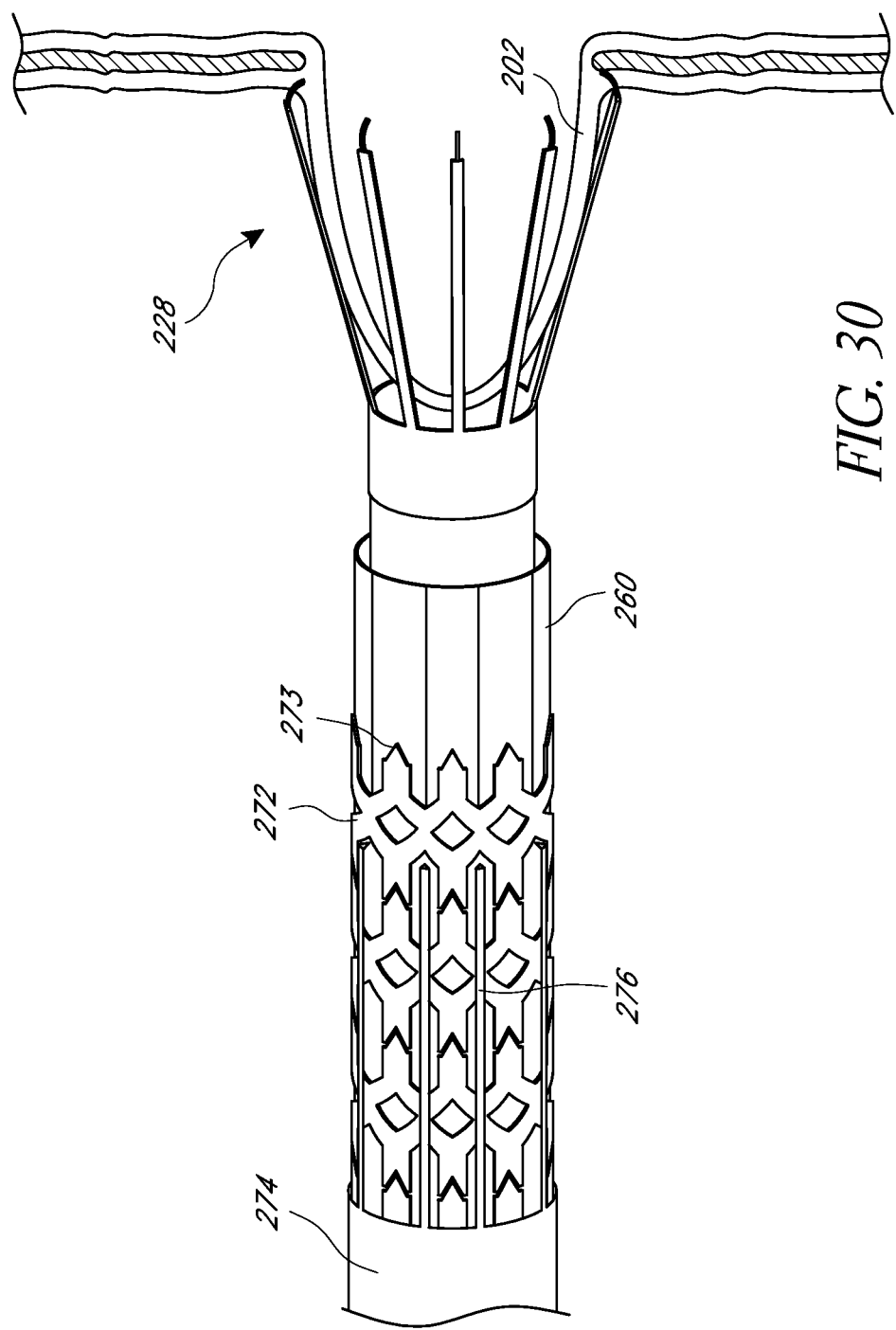
FIG. 30 schematically illustrates another method including contacting the lining of the colon around a site of an opening to a diverticulum with the distal rim of an expanded basket and inverting the diverticulum into the basket, a plurality of closure clips proximal to the basket.

FIG. 30 schematically illustrates another method including contacting the lining of the colon around a site of an opening to a diverticulum 202 with the distal rim of an expanded basket 228 and inverting the diverticulum 202 into the basket 228. A plurality of closure clips 272 is proximal to the basket 228. As described above with respect to FIGS. 24A and 24B and as shown in FIG. 30, the diverticulum 202 may be inverted by negative pressure applied to the colon and/or the basket 228 and/or positive pressure applied to the peritoneal cavity, the inverted diverticulum 202 can be at least partially within the basket 228, and the delivery sheath 260 can be advanced over the basket 228.

As described with respect to FIG. 24C, the advancing tool 274 can be used like the pusher tube 264 to distally push a single clip 272 toward the distal end of the delivery sheath 260, which is around the basket 228 and the diverticulum 202. Like the clip 262, the clip 272 can expand to fit around the basket 228 and the diverticulum 202. The fingers 276 of the advancing tool 274 allow the advancing tool 274 to expand around the delivery sheath 260. As described with respect to FIG. 24D, the basket 228 may then be withdrawn and the delivery sheath 260 and the advancing tool 274 may be at least partially withdrawn, leaving the clip 272 around the diverticulum 202. Withdrawing the advancing tool 274 may include proximally sliding the advancing tool 274 until the teeth 277 engage or snap into an aperture in the most distal clip 272 remaining on the delivery sheath 260. Once released from its position around the delivery sheath 260, the clip 272 can return to its initial shape, including the teeth 273 turning radially inward, substantially as illustrated in FIG. 25. The initial shape of the clip 272, the size and shape of the teeth 273, and the size and shape of the recesses 271 can be adjusted, for example to enhance the engagement of multiple clips 272 on a delivery sheath 260. The clip 272 remains in place once the diverticulum inverting device 220 is withdrawn, and the diverticulum 202 is allowed to necrose and slough off or is removed.

Once the advancing tool 274 has engaged the next clip 272, the process may be repeated on the next diverticulum 202. In this manner, multiple clips 272 can be stored in the working channel of a colonoscope for sequential delivery to treat multiple diverticula 202 without removing the diverticulum inverting device from the colonoscope (e.g., without reloading a new clip onto the device and without loading a new device with a preloaded clip) and without removing the colonoscope from the colon.

The clips 262, 272 may present procedural complications. For example, if improperly sized, there is a potential to create microperforations in the colon that could result in the release of colonic bacteria into the peritoneal cavity, at least until the onset of serosal healing where the teeth 263, 273 transect the colonic wall tissue. Even absent microperforation, the tissue proximate to the clips 262, 272 could become infected. Additionally, local bleeding at the site entry point of the teeth 263, 273 is possible. To limit, reduce, inhibit, or eliminate the impact any such complications and/or to promote rapid healing, at least a portion of the clips 262, 272, for example at least the teeth 263, 273, may include a drug coating.

As described above, the clip 262, 272 may include SMA such as nitinol or chromium cobalt, or a metal such as stainless steel. Coating the clip 262, 272 with a drug coating may be in accordance with methods known in the art, such as direct attachment (e.g., with or without surface treatment), embedding in a polymer layer, and the like. Various polymers can help control the elution rate of the drug and/or allow the coating to include multiple drugs (e.g., both coagulants and antibiotics).

The drug coating may include antibiotics to inhibit or prevent infection while the injured tissue is healing and/or coagulation modifiers to reduce or minimize blood loss and promote rapid healing. Examples of antibiotic drugs that may be used include amoxicillin-clavulanate (augmentin), trimethoprim-sulfamethoxazole (co-trimoxazole), fluoroquinolone, metronidazole (flagyl), clindamycin (cleocin), aminoglycoside, gentamicin, tobramycin, monobactam (aztreonam), cephalosporin, ceftriaxone, ceftazidime (fortaz), cefotaxime, cefoxitin (mefoxin), cefotetan, an β-lactamase inhibitors (e.g., ampicillin-sulbactam, ticarcillin-clavulanate (timentin)). Other antibiotics are also possible. Examples of coagulation modifiers that may be used include oxidized cellulose, absorbable gelatin, fibrin foam, thrombin, and microfibrillar collagen. Other coagulation modifiers are also possible.

Figure 31:
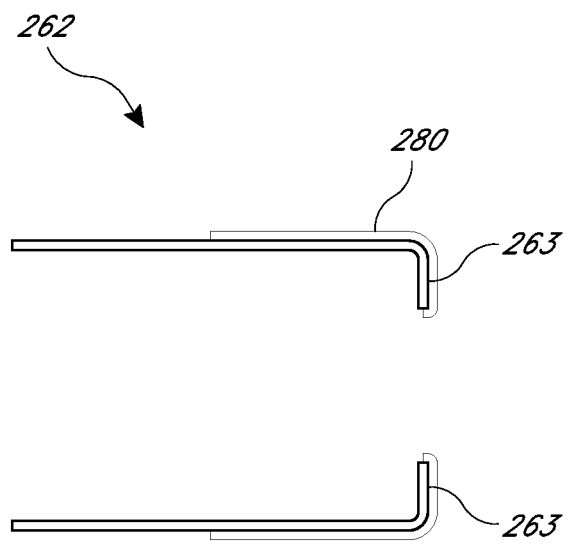
FIG. 31 is a cross-sectional view of a closure clip showing radially inward orientation of tissue-engaging teeth, the closure clip including a drug coating.
Figure 32:
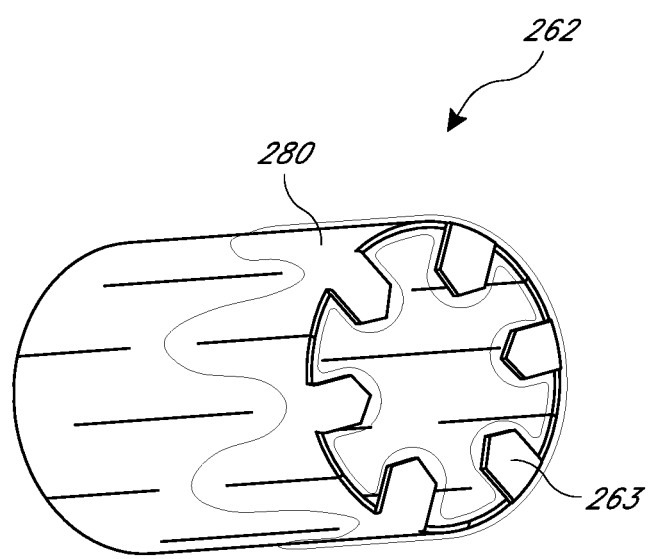
FIG. 32 is a perspective view of a closure clip showing radially inward orientation of tissue-engaging teeth, the closure clip including a drug coating.
Figure 33:
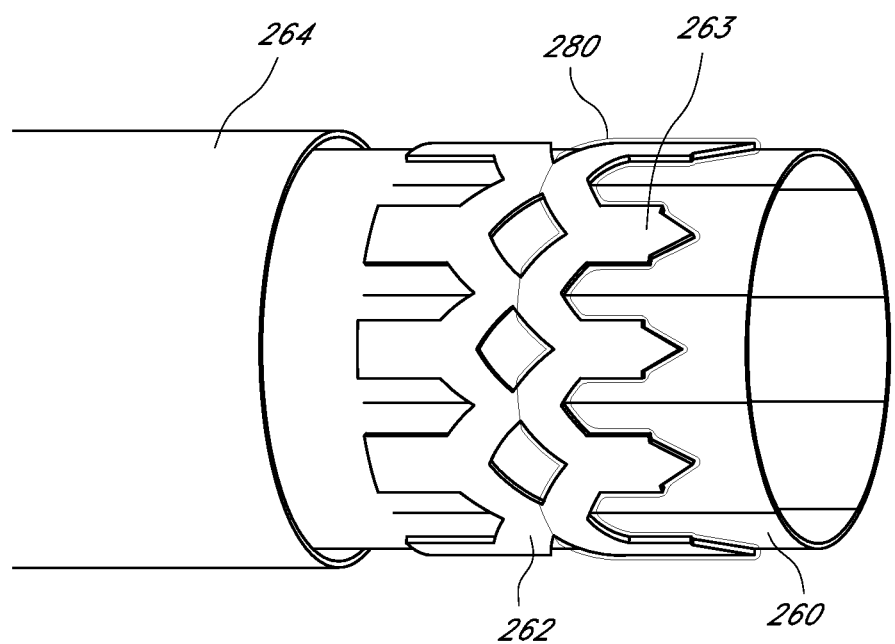
FIG. 33 is a perspective view of a closure clip including a drug coating coaxially arranged over an expandable delivery sheath.

FIG. 31 is a cross-sectional view of a closure clip 262 showing radially inward orientation of tissue-engaging teeth 263. The closure clip 262 includes a drug coating 280 over the teeth 263, and a distal portion. FIG. 32 is a perspective view of the closure clip 262 showing radially inward orientation of tissue-engaging teeth 263 and the drug coating 280. FIG. 33 is a perspective view of a closure clip 262 including a drug coating 280 coaxially arranged over an expandable delivery sheath 260. The drug coating 280 may be only on portions of the clip 262 that do not contact other components. For example, the interior surfaces of the clip 262 illustrated in FIG. 33, which contact the delivery sheath 260, and the proximal end, which contacts the pusher tube 264, do not include the drug coating. The drug coating 280 may be over the inside and outside of a clip 262, for example fully covering the teeth 263.

Figure 34:
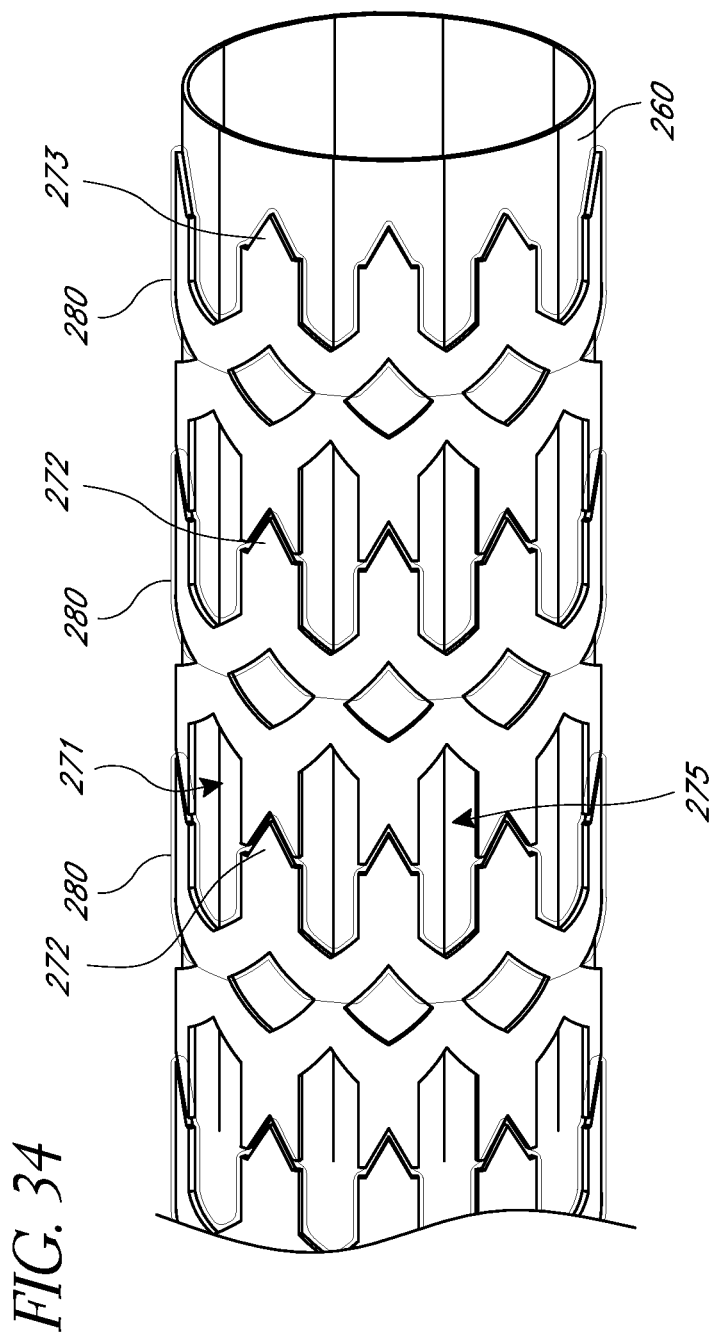
FIG. 34 is a side elevational view of a plurality of expanded closure clips including a drug coating.

FIG. 34 is a side elevational view of a plurality of expanded closure clips 272 including a drug coating. The closure clips 272 include a drug coating 280 over the teeth 273, and a distal portion. The drug coating 280 may be only on portions of the clips 272 that do not contact other components. For example, the interior surfaces of the clip 272 that are configured to contact a delivery sheath 260, as shown in FIG. 26, and the proximal apertures, which contact the advancing tool 274, do not include the drug coating. Although the teeth 273 contact the recesses 271, they may include the drug coating 280.

Figure 35:
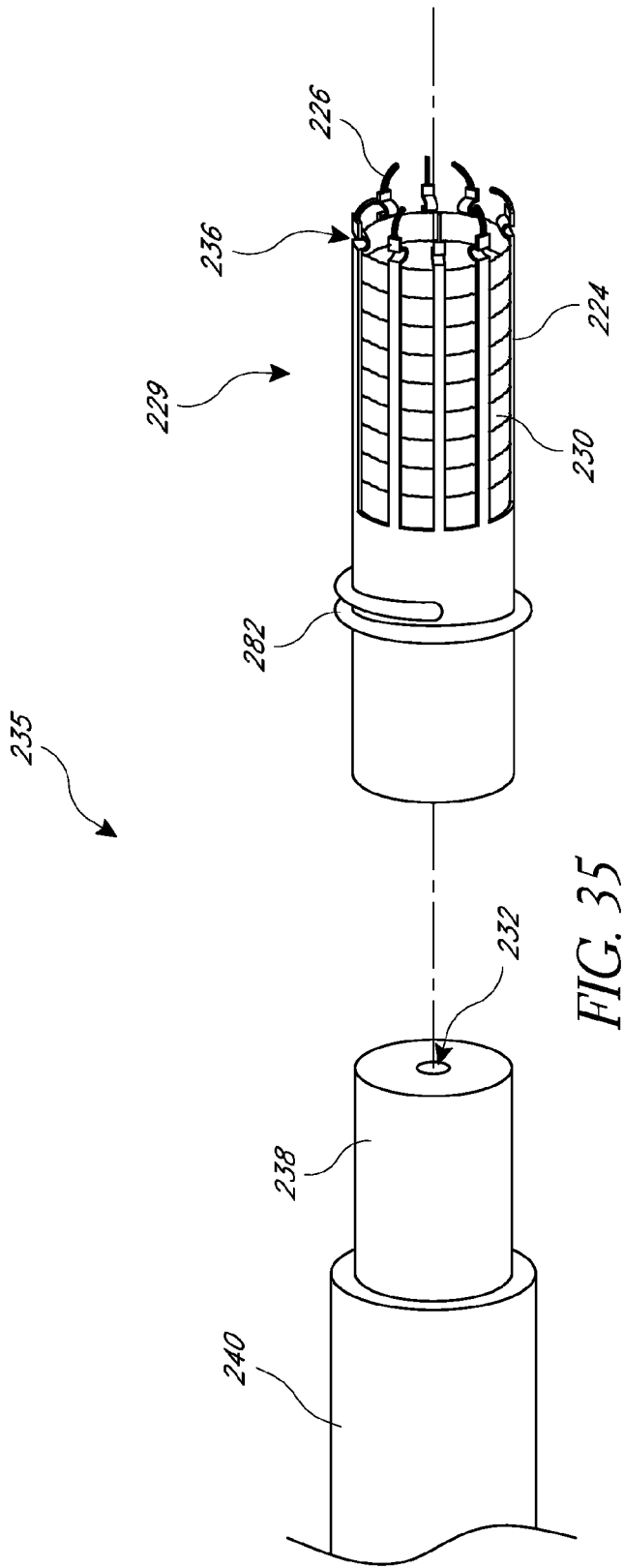
FIG. 35 is an exploded perspective view of a detachable basket, coaxial pusher tubes, and a spring ring.

FIG. 35 is an exploded perspective view of a detachable basket 229, coaxial pusher tubes 238, 240, and a spring ring 282. Although the elements may not be completely interchangeable with the components described above, the basket 229 may be similar to the basket 228 (e.g., including arms 224, spikes 226, and a film 230). As illustrated in FIG. 35, the basket 229 is in a collapsed or delivery configuration. However, the basket 229 is detachable, so it may be considered an element of a closure clip. The spring ring 282 is configured to maintain a mouth of an inverted diverticulum and remain after withdrawal of the device 235, so the spring ring 282, may also be considered a closure clip or an element of a closure clip, even though it may not contact the diverticulum directly.

The spring ring 282 includes greater than 180° of an arcuate shape such that the spring ring 282 can radially inwardly compress after expansion. The spring ring may include greater than 360° of an arcuate shape, where portions of the spring ring 282 longitudinally overlap like a coil, as illustrated in FIG. 35. The spring ring 282 may include a SMA such as nitinol, although the spring ring 282 is shaped such that non-SMA biocompatible materials may also be able to spring back, for example due to tempering. The spring ring 282 is initially proximal to the arms 224 of the basket 229, which allows the basket 229 to open when not confined, for example within a working lumen of a colonoscope or a delivery sheath. Like a closure clip 262, 272, the spring ring 282 is distally advanced by a pusher tube 240 during a diverticulum treatment procedure.

The basket 229 optionally includes detents 236, for example in the arms 224, which can help to maintain the position of a spring ring 282 after it is distally advanced. For example, the shape memory of the arms 224 causes an outward force that might push the spring ring 282 proximally unless the spring ring 282 is nestled in detents 236. The detents can be proximal to the spikes 226.

The basket 229 is removably or detachably attached to a pusher 238. The pusher 238 includes a vacuum lumen 232, which can apply negative pressure to the interior of the basket 229, which can help invert a diverticulum. The basket 229 may be attached to the pusher 238 by an adhesive, wax, a thermal bond, threading, or vacuum, which can be applied through the vacuum lumen 232 or another lumen.

Figure 36:
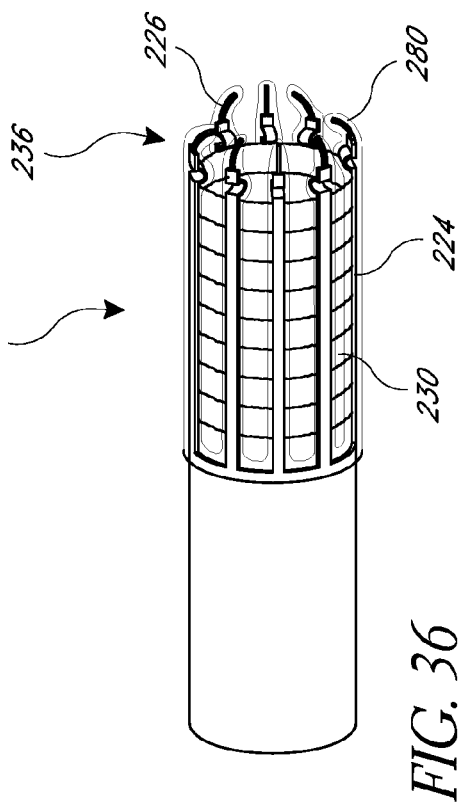
FIG. 36 is a perspective view of a detachable basket including a drug coating.

FIG. 36 is a perspective view of a detachable basket 229 including a drug coating 280. As described above, the drug coating 280 may include at least one of antibiotics and coagulation modifiers. The drug coating 280 covers at least the spikes 226 at the distal regions of the arms 224, which may contact and dig into tissue like the teeth 263, 273 of the clips 262, 272. In use, the spring ring 282 is also proximate to the mouth of the diverticulum, so the spring ring 282, which as described above may be characterized as a clip because its action maintains closure of a collapsed inverted diverticulum, may also include a drug coating like the drug coating 280.

Figure 37:
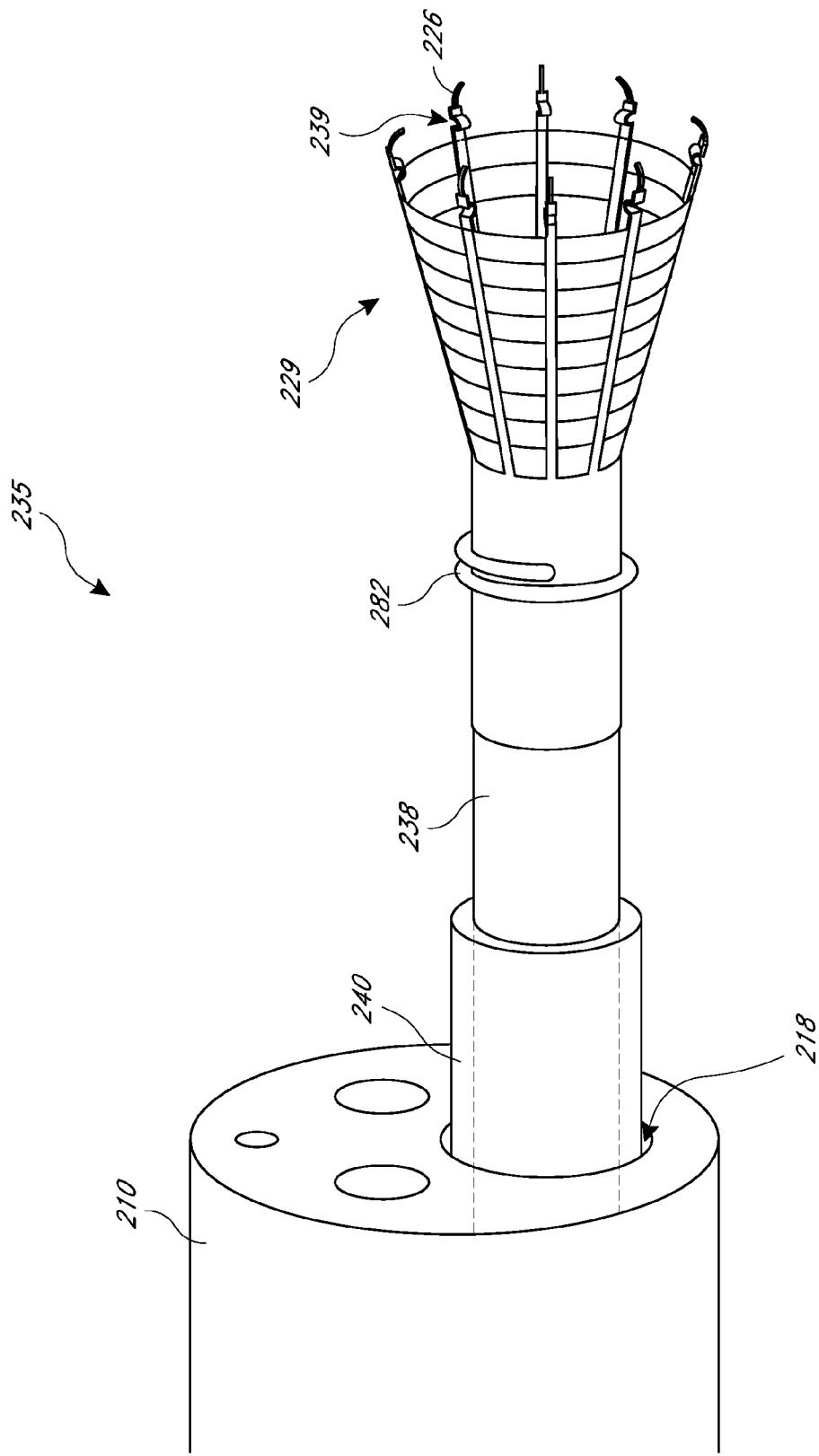
FIG. 37 is a perspective view of a device extending distally from the working channel of a colonoscope, the device including a detachable basket of FIG. 36 with the arms of the detachable basket expanded radially outward after exiting from the working channel of the colonoscope.

FIG. 37 is a perspective view of a device 235 extending distally from the working channel 218 of a colonoscope 201. The device 235 includes a detachable basket 229. The arms 224 of the detachable basket 229 expand radially outward after exiting from the working channel 218 of the colonoscope 210 because the arms 224 of the basket are self-expanding, although methods and devices to force radial expansion of the arms 224 are also possible.

Figure 38A:
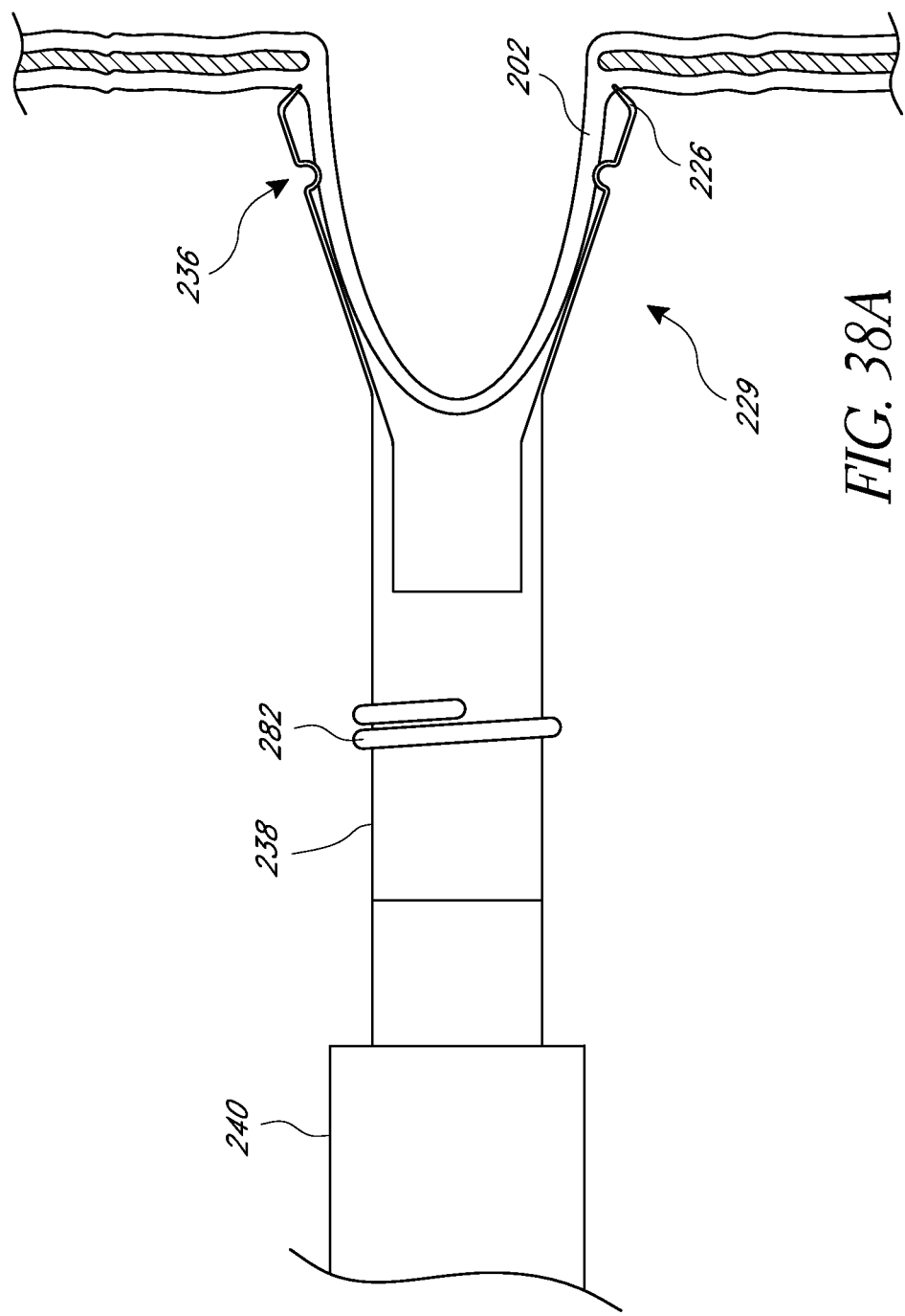
FIGS. 38A-38D schematically illustrate a method including, respectively, (A) contacting the lining of the colon around a site of an opening to a diverticulum with the distal rim of an expanded detachable basket and inverting the diverticulum into the basket; (B) advancing a pusher and a spring ring distally over the expanded detachable basket; (C) further advancing the spring ring distally over the expanded basket, the closure clip over the distal rim of the detachable basket, and detaching the detachable basket; and (D) withdrawing the device proximal to the detached basket, leaving the detached basket around the inverted diverticulum.

FIGS. 38A-38D schematically illustrate a method of treating a diverticulum 202. The method is similar to the methods described above, with some differences that will be highlighted. In FIG. 38A, the diverticulum 202 has been inverted according to any of the methods discussed above and the basket 229 has been positioned around the tissue at the base of a diverticulum 202, the inverted diverticulum 202 at least partially within the basket 229 and the spikes 226 engaging the tissue surrounding the diverticulum 202. The basket 229 is still coupled to the pusher 238. The system 235 does not include a delivery sheath 260. The spring ring 282 is proximal to the basket 229.

Figure 38B:
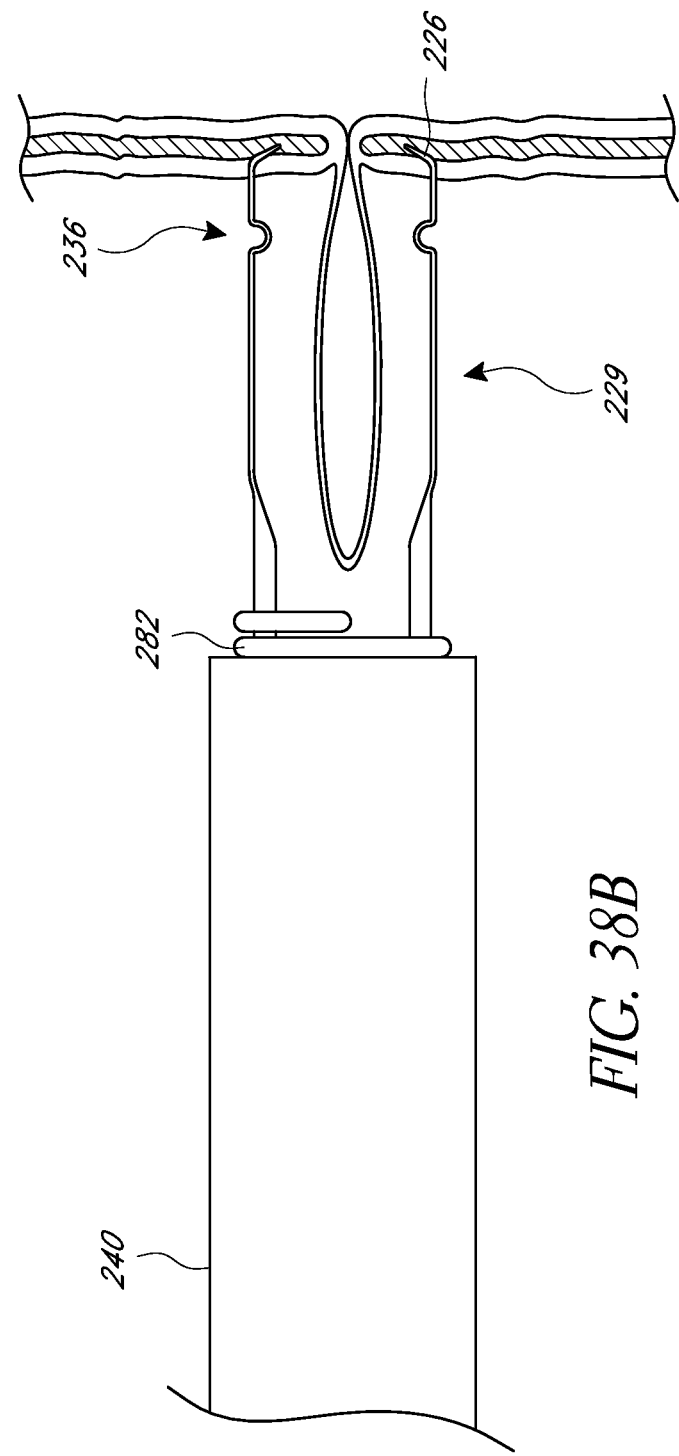

In FIG. 38B, the pusher tube 240 has been distally advanced over a proximal portion of the basket 229, which distally pushes the spring ring 282 over the basket 229. The spring ring 282 may expand as it travels over the basket 229. The pusher tube 240 alone, the spring ring 282 alone, or the pusher tube 240 and the spring ring 282 in combination, may force the arms 224 of the basket 229 radially inward, compressing the diverticulum 202 in the basket 229. The pusher tube 240 continues to push the spring ring 282 distally until the spring ring is proximate the mouth of the diverticulum 202, for example engaging the detents 236. The torque that can be applied to the arms 224 of the basket 229 by the spring ring 282 when the spring ring is proximate to a distal end of the arms 224 can maintain the basket 229 in a collapsed state with the diverticulum 202 inside. The spring ring 282 may hold the mouth of the diverticulum closed even more strongly than a clip 262, 272.

Figure 38C:
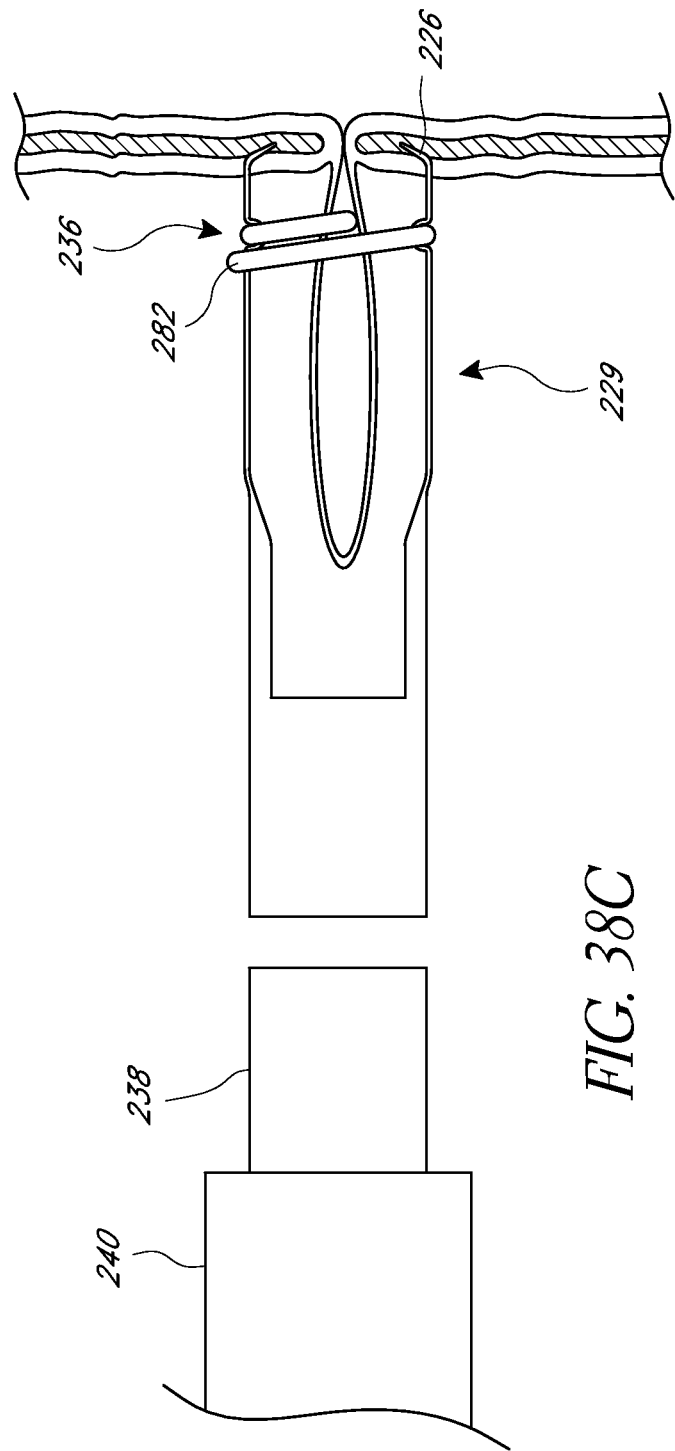

In FIG. 38C, the spring ring 282 has engaged the detents 236, and the basket 229 has been detached from the pusher 238, for example by releasing vacuum, threading, removing adhesive, etc. as described above. The remainder of the device 235, including the pusher tubes 238, 240 may then be withdrawn, leaving the basket 229 and the spring ring 282 around the inverted diverticulum 202.

Figure 38D:
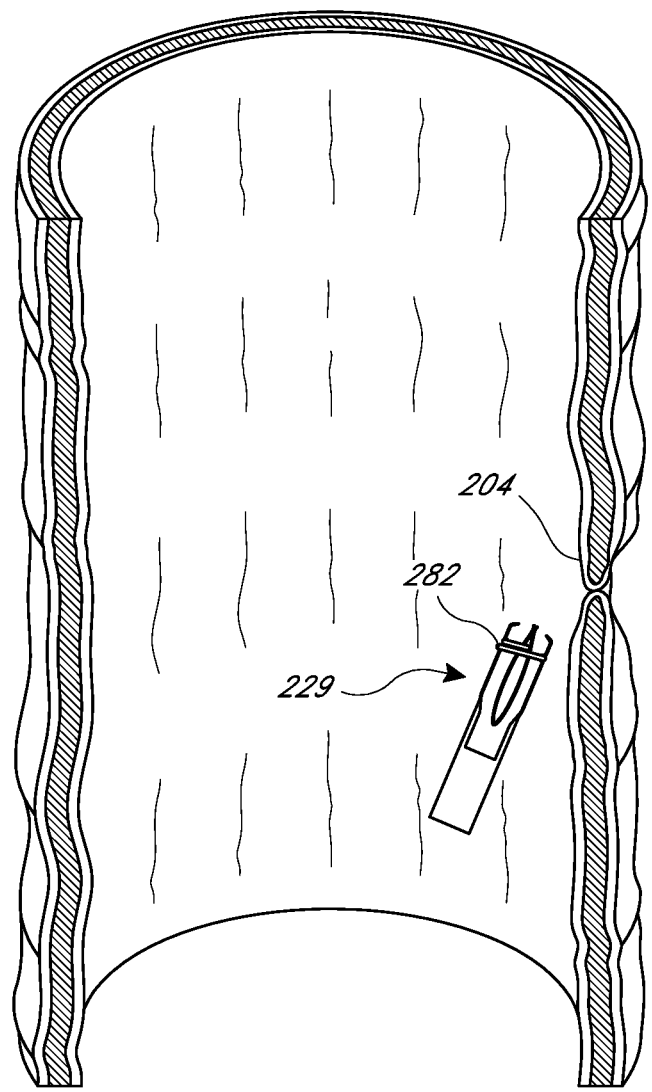

FIG. 38D is a perspective view of a basket 229 and the spring ring 282 around the neck of a necrosed diverticulum 202 that is in the process of sloughing off the colon. The layers of serosa 204 have joined together while the diverticulum 202 is necrosed. The clip basket 229 and the spring ring 282 may slough off with the necrosed diverticulum 202 and pass through the body. Alternatively, the clipped diverticulum 202 can be removed with a RF snare, cautery wire, blade, or other removal implement, as is known in the art. Removing the clipped diverticulum 202 can be done after the serosa 204 has grown and closed the opening to the diverticulum 202. Once removed, the diverticulum 202, the basket 229, and the spring ring 282 can be collected and removed from the colon, or can be allowed to pass.

In contrast to the devices and methods described above that use a clip 262, 272, in which the spikes of a basket engage tissue and then teeth 263, 273 of the clip 262, 272 engage the tissue, creating two sets of punctures, the basket 229 only engages the tissue once with the spikes 226.

The basket 229 and spring ring 282 may accommodate very large diverticula, as the process is only limited by the diameter of the distal rim of the basket 229, which may contrast, for example to other methods and devices described herein in which the size of a diverticulum that may be treated is limited by the maximum expansion of a clip 262, 272.

As described above, the basket 229 is similar to other baskets described herein such that the cost of the basket 229 may be similar to the cost of other baskets described herein. When treating a single diverticulum or in embodiments where only one closure clip is loaded on the device, the basket is not reused, so the cost of the basket 229, which is detached, remains at parity. However, the spring ring 282, which may be a relatively simple portion of a coil, may be significantly less expensive than the clips 262, 272, which may be, for example, laser-cut hypotubes that are also bent (e.g., to orient the teeth 263, 273 radially inward) and heat-set. Accordingly, the cost of the system 235 can be reduced over the cost of systems including a clip 262, and even less expensive than systems including clips 272.

In addition to inverting and treating a diverticulum with a device inserted into the colon, diverticula can be treated laparoscopically. Laparoscopic treatment provides another minimally invasive, tissue sparing method to surgically close and remove diverticula without removing large segments of colon tissue. Although described in more detail below, a laparoscopic device for inverting a diverticulum can include a flange portion surrounding a working channel of the device that can attach (e.g., through suction) to tissue surrounding a diverticulum. Applying positive pressure within the laparoscopic device can then invert the diverticulum, and the working channel of the device can be used to access the diverticulum with a diverticulum closing tool.

Laparoscopic treatment can be performed in conjunction with or independently of an endoscopic procedure. For example, a colonoscope can be used initially to help identify a diverticulum, a laparoscopic tool can be used to help treat it, and the colonoscope can help monitor the treatment. Alternatively, a laparoscopic tool can be used to identify, invert, and close a diverticulum, and a colonoscope can be used to monitor the treatment and/or remove the closed diverticulum.

Figure 39:
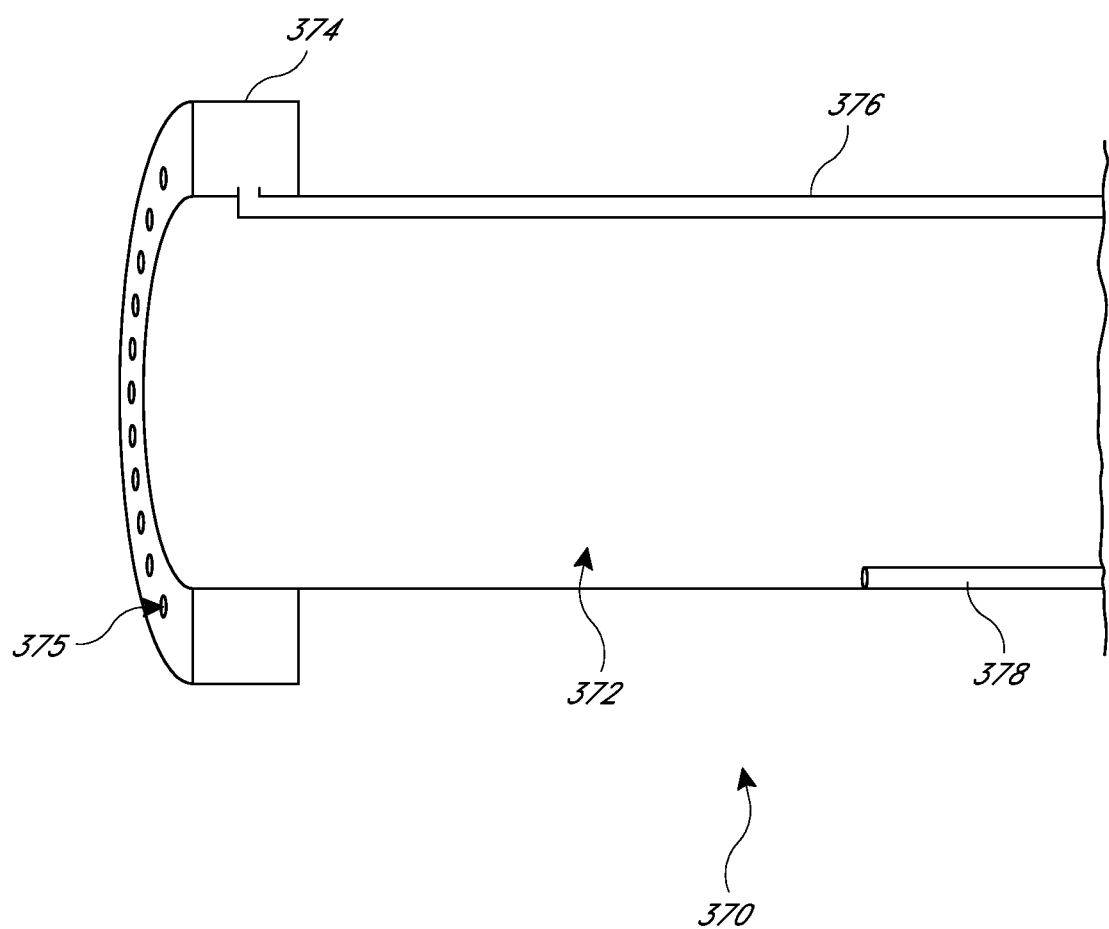
FIG. 39 is a perspective cross-sectional view of a laparoscopic access port including a working channel, a positive pressure line, and a distal end including a hollow suction flange, the hollow suction flange coupled to a negative pressure line.

FIG. 39 is a perspective cross-sectional view of a laparoscopic access port 370. The access portion includes a working channel 372, a positive pressure line 378, and a distal end including a hollow suction flange 374. The hollow suction flange 374 is coupled to a negative pressure line 376. The working channel 372 can be a hollow tube. The working channel 372 may be accessible at a proximal end to a person using the access port 370, and extends all the way to the distal end of the access port 370.

The access port 370 may include a distal portion including a hollow flange 374 The hollow flange 374 may include a plurality of holes 375 along a distal surface. The hollow flange 374 can be in fluid communication with a negative pressure line 376, and the interior of the working channel 372 can be in fluid communication with a positive pressure line 378. The hollow flange 374 may surround the entire circumference of the working channel 372, and can have a diameter on the order of about two centimeters. Alternatively, the diameter can be larger or smaller, depending on the diverticulum or other lesion sought to be treated. The hollow flange 374 should be at least slightly larger than any diverticulum sought to be inverted.

Figure 40:
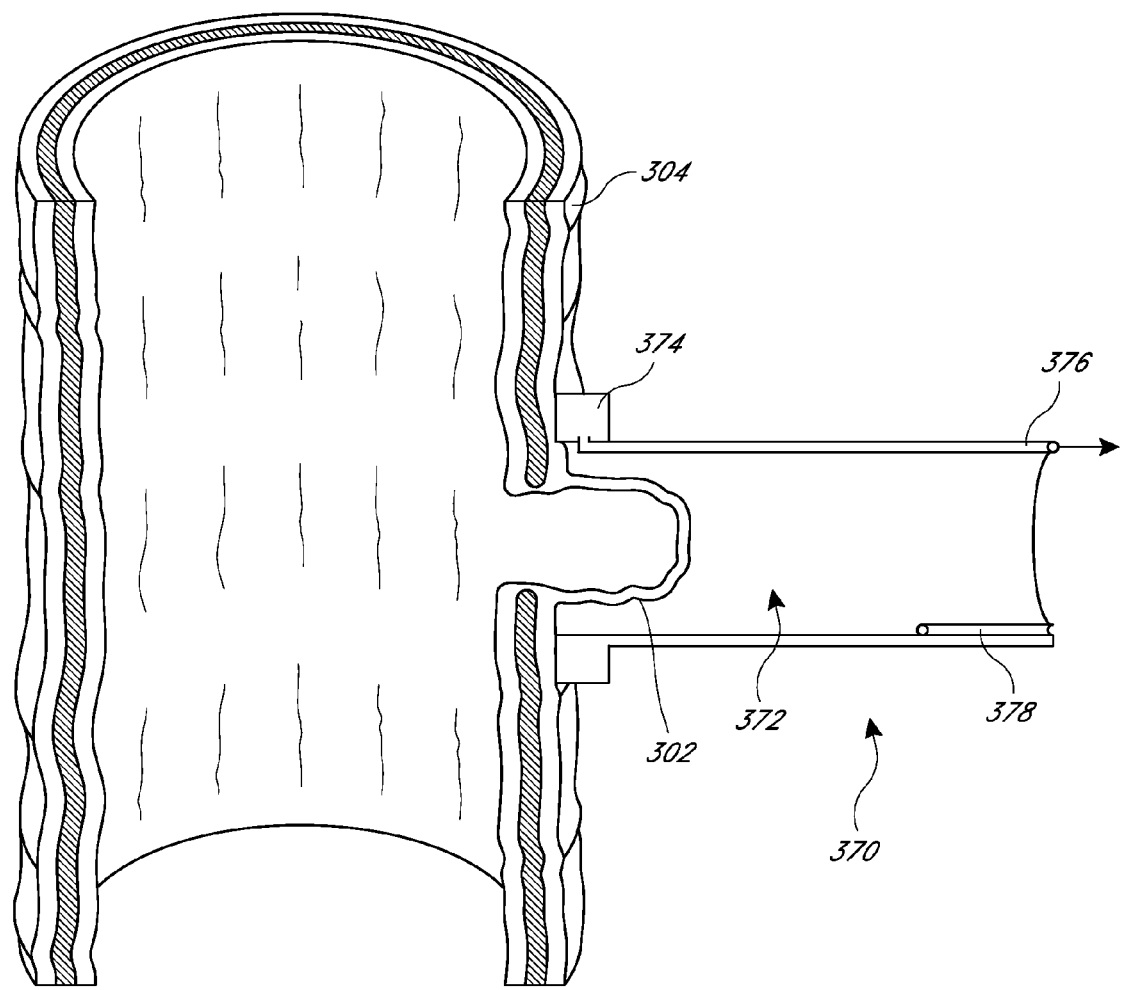
FIG. 40 is a perspective cross-sectional view of the laparoscopic access port of FIG. 39 and a diverticulum extending into the access port from a wall of a colon.

FIG. 40 is a perspective cross-sectional view of the laparoscopic access port 370 and a diverticulum 302 extending into the access port 370 from a wall of a colon. The flange 374 can be positioned substantially flush against the tissue surrounding the diverticulum 302—in the case of a colonic diverticulum 302, the flange 374 may be substantially flush against the serosa 304. Any imaging device known in the art can be used to help locate the diverticulum 302 and appropriately position the access port 370. The imaging device can be included within the working channel 372 of the access port 370 or used separately from the access port 370. Additionally, if desired, the light of a colonoscope within the colon can help guide the access port 370 toward the diverticulum 302 being treated.

Figure 41:
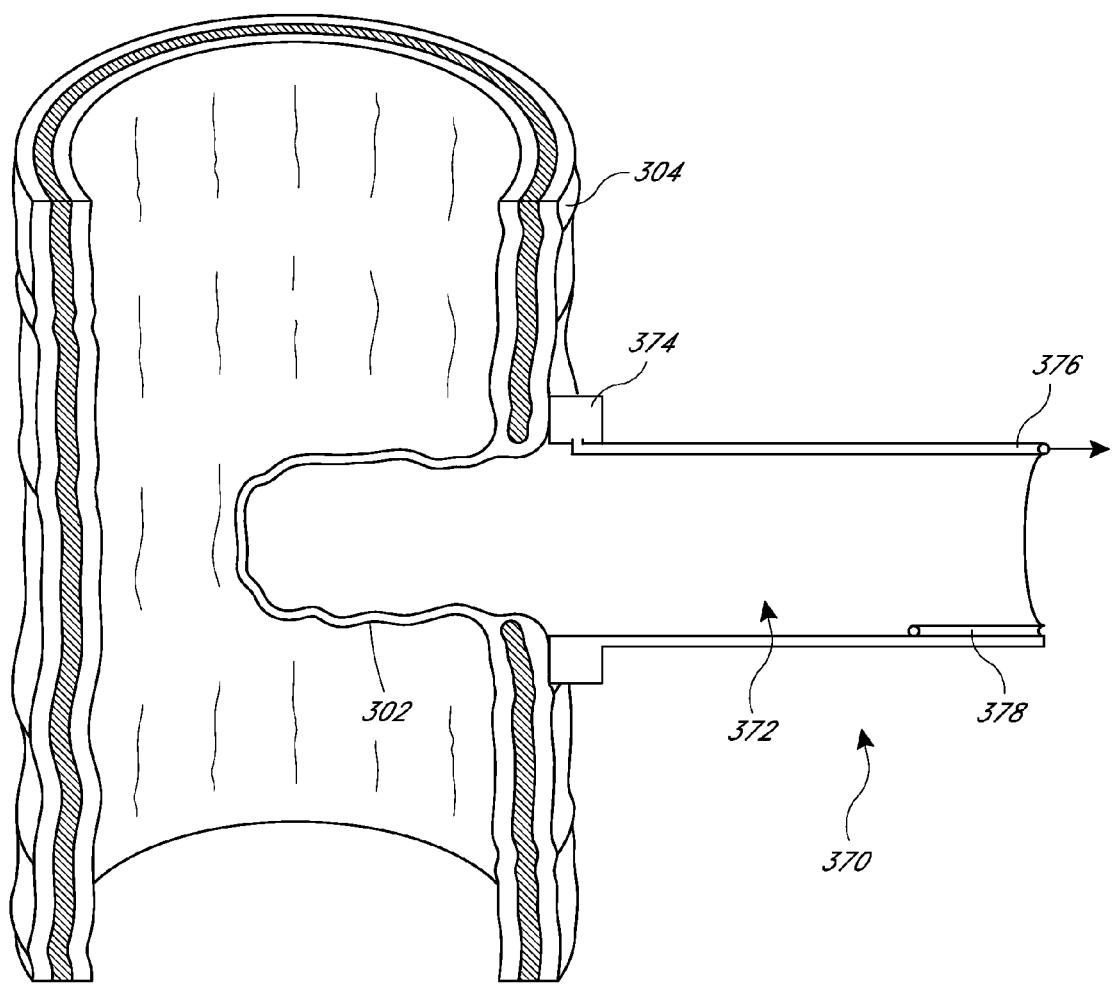
FIG. 41 is a perspective cross-sectional view of the laparoscopic access port of FIG. 39 and a diverticulum following application of positive pressure within the access port to cause the diverticulum to at least partially invert into the lumen of the colon.

Once the access port 370 is in place against the tissue surrounding the diverticulum 302, the negative pressure line 376 can be activated, creating a negative pressure in the flange 374 and a suction fit between the holes 375 (FIG. 39) and the tissue surrounding the diverticulum 302. The suction fit can create a substantially airtight seal between the flange 374 and the serosa 304. With a substantially airtight seal in place, and good contact between the flange 374 and the tissue surrounding the diverticulum 302, the positive pressure line 378 can be activated to increase the pressure in the working channel 372. FIG. 41 is a perspective cross-sectional view of the laparoscopic access port 370 and a diverticulum 302 following application of positive pressure within the access port 370 to cause the diverticulum 302 to at least partially invert into the lumen of the colon. It is not necessary that the substantially airtight seal between the flange 374 and the tissue surrounding the diverticulum 302 is airtight or absolute. It is sufficient that the negative pressure from line 376 creates an attractive force between the flange 374 and the tissue surrounding the diverticulum 302 that tends to cause the tissue surrounding the diverticulum 302 to adhere to the flange 374, even when the pressure within the working channel 372 is increased (to invert the diverticulum 302). In cases when the fit between the flange 374 and the tissue surrounding the diverticulum 302 is not airtight, the negative pressure may be higher than the positive pressure. Once the diverticulum 302 has been inverted, it can be closed through a number of methods.

Figure 42:
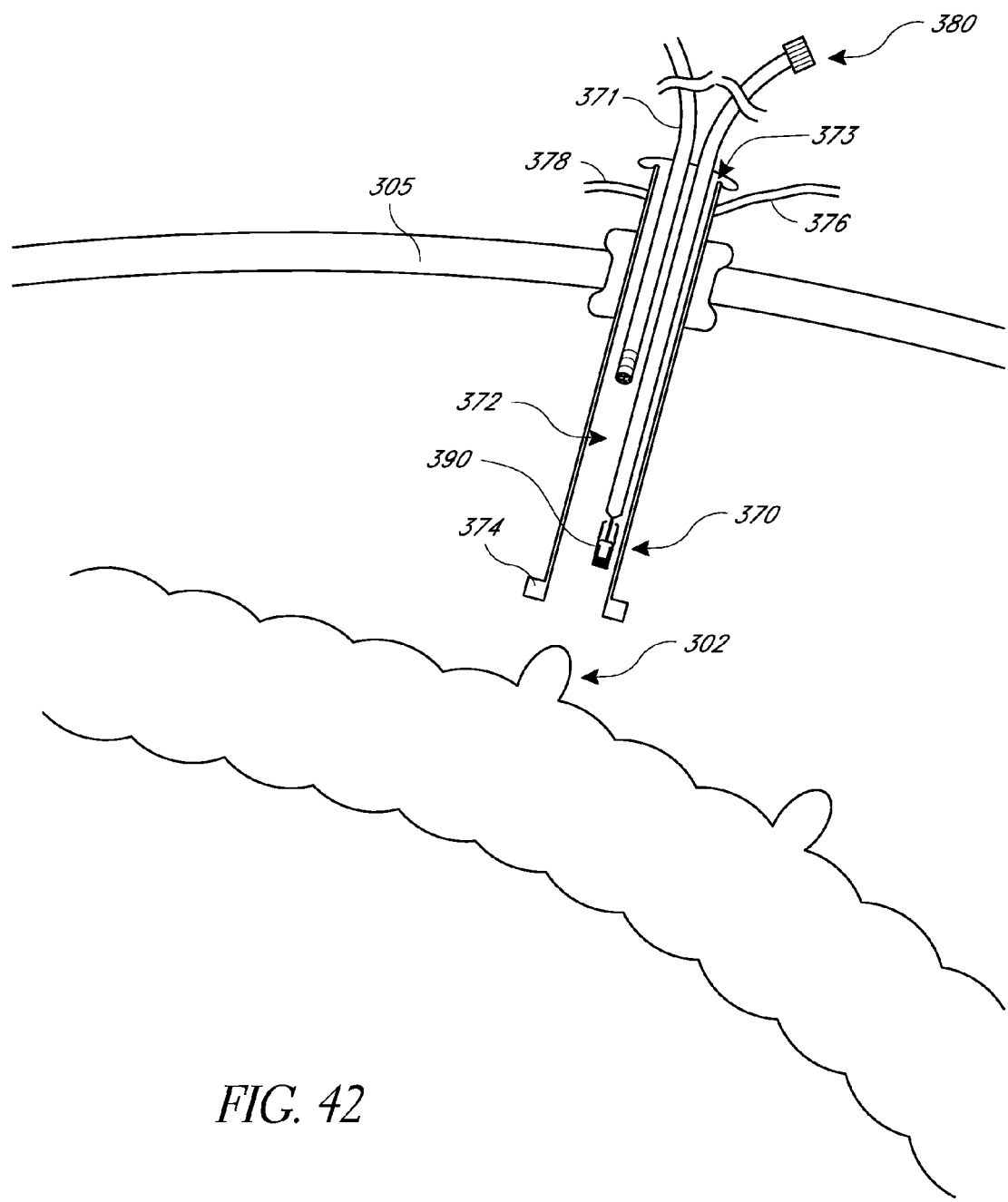
FIG. 42 shows a laparoscopic diverticulum inverting device including a laparoscopic access port, and a scope and a closure clip assembly within the access port of the laparoscopic access port, a distal end of the laparoscopic device proximate a diverticulum.

FIG. 42 shows a laparoscopic diverticulum inverting device including a laparoscopic access port 370, and a scope 371 and a closure clip assembly or deployment tool 380 within the laparoscopic access port 370. The laparoscopic device has been inserted through the abdominal wall 305 and the distal end of the laparoscopic device is proximate a diverticulum 302. The access port 370 may include a proximal region including a sealed port 373, which can allow the insertion of a scope 371 and/or a deployment tool 380 into the working channel 372. The scope 371 can help visualize the location of the access port 370 and/or a treatment performed using the deployment tool 380. The closure clip deployment tool 380 can deliver a clip 390 to into the diverticulum 302.

Figure 43:
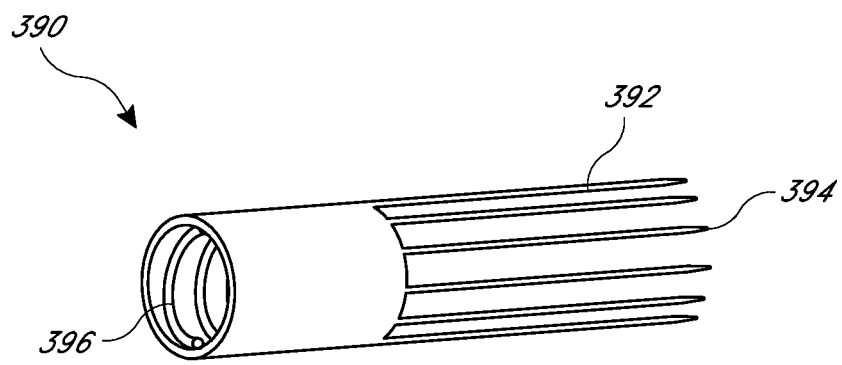
FIG. 43 is a perspective view of a closure clip including an internally threaded distal region and a plurality of closure arms extending proximally from the internally threaded distal region.
Figure 44:
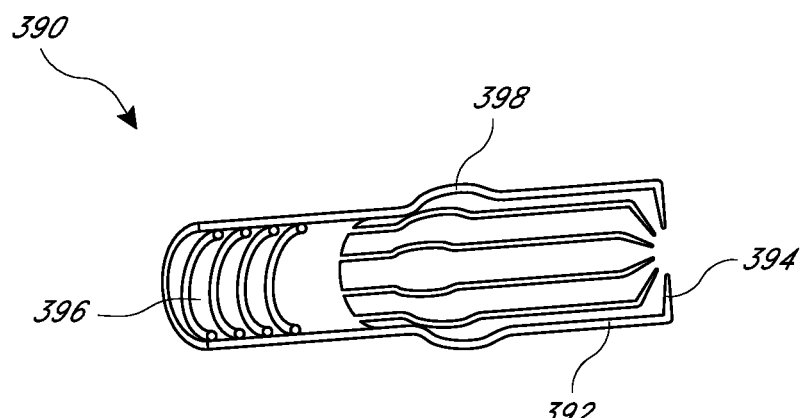
FIG. 44 is a cross-sectional view of a closure clip including an internally threaded distal region and a plurality of closure arms extending proximally from the internally threaded distal region, the plurality of closure arms including an expander receiving area and tissue-engaging tips biased radially inward.

FIG. 43 is a perspective view of a closure clip 390 including an internally threaded distal region 396 and a plurality of closure arms 392 extending proximally from the internally threaded distal region 396. The clip 390 may include a hypotube that is cut to form the plurality of closure arms 392 and spikes 394 at a proximal end of the clip 390. FIG. 44 is a cross-sectional view of a closure clip 390 including an internally threaded distal region 396 and a plurality of closure arms 392 extending proximally from the internally threaded distal region 396. The plurality of closure arms 392 include an expander receiving area 398 and tissue-engaging tips 394 biased radially inward. The clip 390 illustrated in FIG. 43 may assume the shape of the clip 390 illustrated in FIG. 44 when the clip 390 is not restrained, for example by a deployment tool 380. In FIG. 44, the proximal ends of the arms 392 are bent radially inward. Alternatively, just the spikes 394 may be bent inward. Additionally, the unrestrained shape of the clip 390 can include a curved portion that forms an expander receiving area 398.

Figure 45:
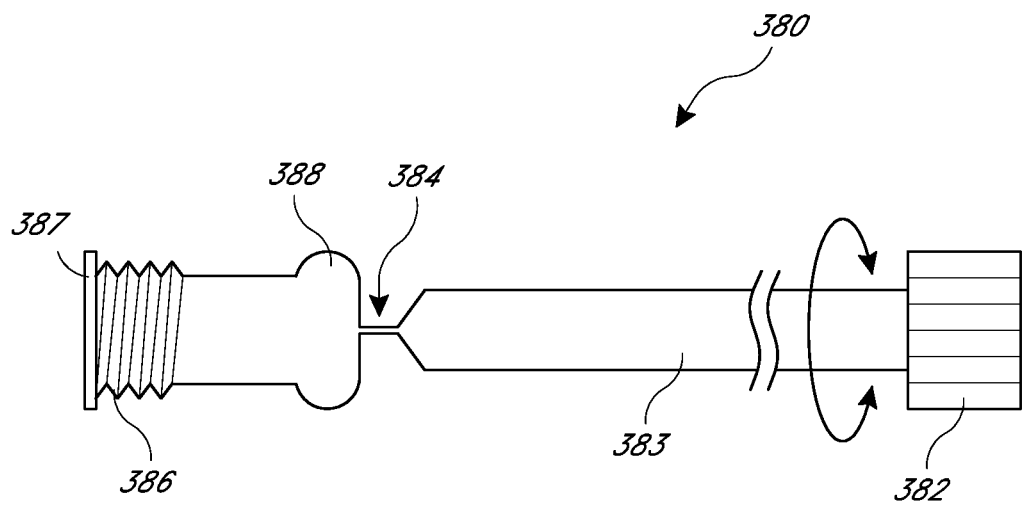
FIG. 45 is a side view of a closure clip deployment tool including a shaft, a handle, a frangible region, an expander region, an externally threaded distal region configured to threadably engage the internally threaded distal region of a closure clip, and a stop.

FIG. 45 is a side view of a closure clip deployment tool 380. The deployment tool 380 includes a handle 382 at a proximal end, a shaft 383 extending distally from the handle 382, an externally threaded region 386 distal to the shaft 383, an expander region 388 located between the externally threaded region 386 and the shaft 383, and a frangible portion 384 between the expander region 388 and the shaft 383. The deployment tool 380 can include a stop 387 at an extreme distal end having a larger diameter than the externally threaded region 386. The clip 390 can be attached to the distal end of the deployment tool 380 for delivery to a diverticulum 302. The clip 390 may be oriented such that the arms 392 point toward the proximal end of the deployment tool 380.

Figure 49:
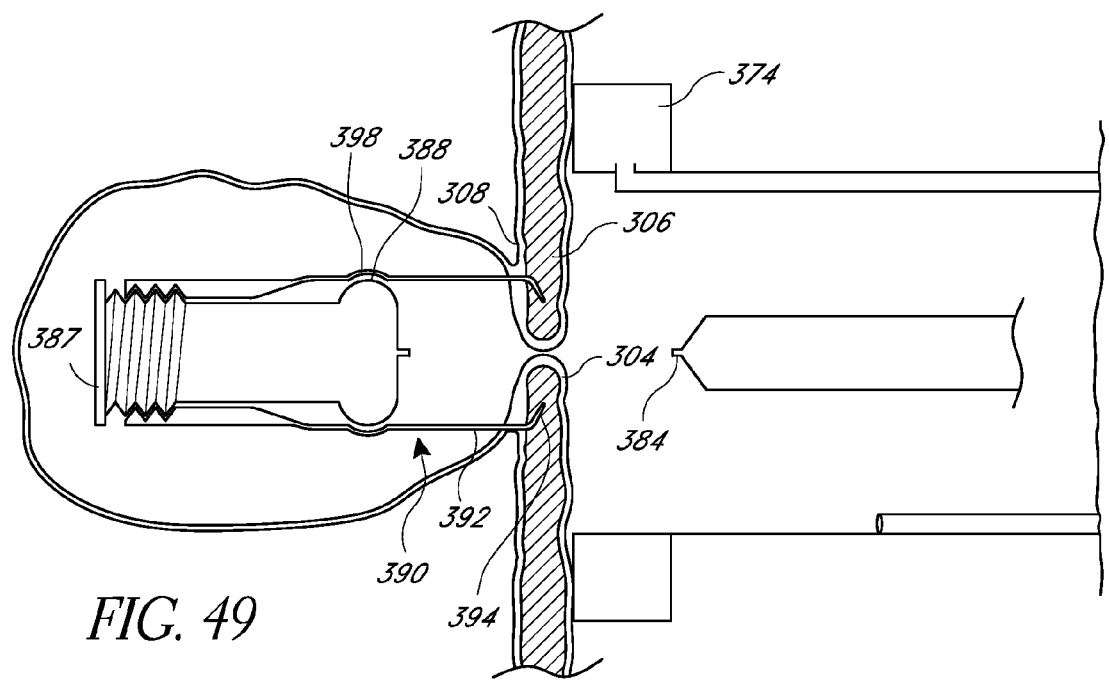
FIG. 49 is a cross-sectional view showing the tissue-engaging tips of the closure clip of the closure clip assembly of FIG. 46 after closing the opening to the inverted diverticulum.

The externally threaded region 386 of the deployment tool 380 may be threaded into the internally threaded region 396 of the clip 390 by rotating the handle 382 in a first direction (e.g., clockwise). Additionally, the expander receiving area 398 and the expander region 388 may be roughly the same size such that the expander region 388 can fit within the expander receiving area 398, as illustrated in FIG. 49. The expander region 388 and the expander receiving area 398 may line up when the deployment tool 380 is completely screwed into the clip 390. A stop 387 can inhibit or prevent the deployment tool 380 from screwing too far into the clip 390.

Figure 46:
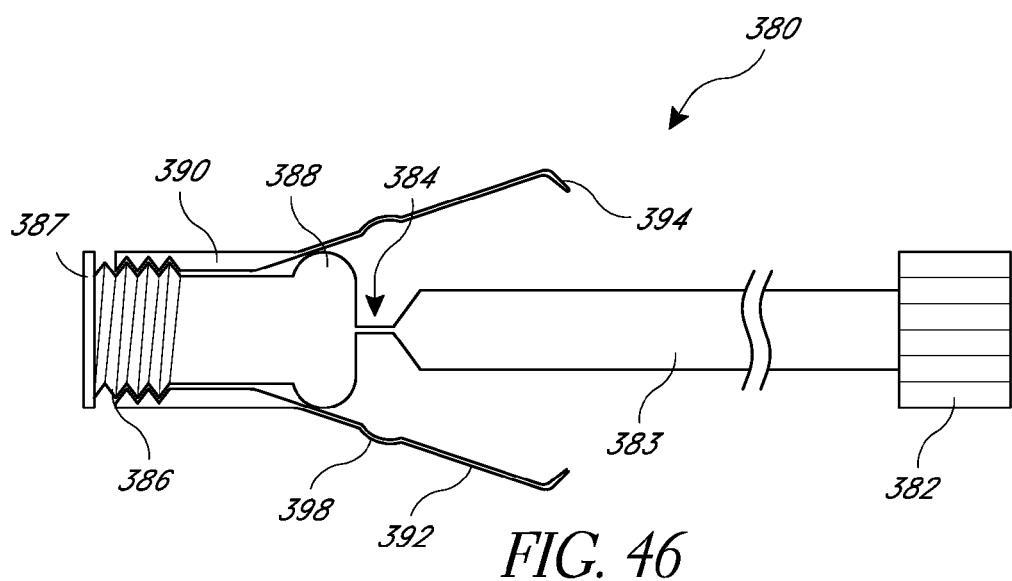
FIG. 46 is a partial cross-sectional view of a closure clip assembly including the closure clip of FIG. 44 and the deployment tool of FIG. 45, the plurality of closure arms being expanded by the expander region of the deployment tool.
Figure 47:
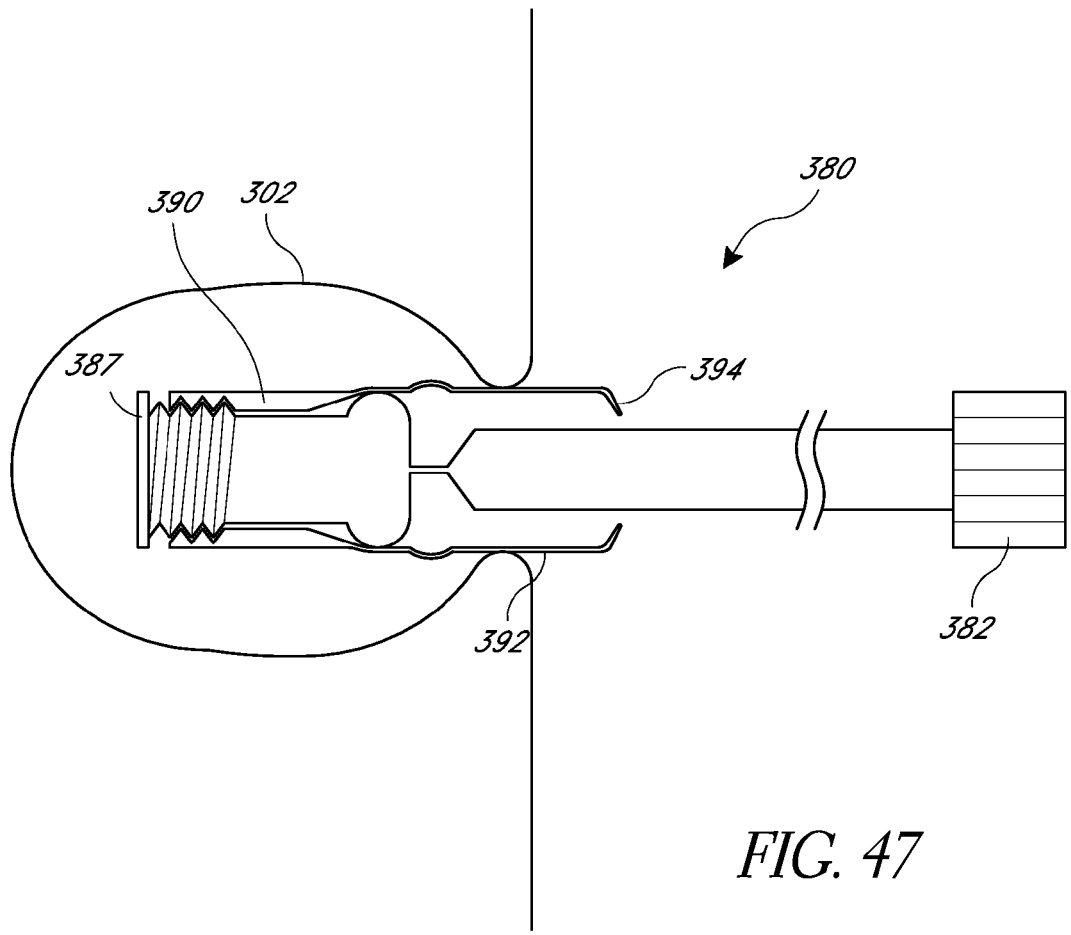
FIG. 47 is a partial cross-sectional view showing the closure clip assembly of FIG. 46 at least partially within an inverted diverticulum.

FIG. 46 is a partial cross-sectional view of a closure clip assembly including the closure clip 390 and the deployment tool 380. The deployment tool 380 can be positioned relative to the clip 390 such that the expander region 388 forces the arms 392 radially outward from their initial shape and toward an expanded configuration. The deployment tool 380 can deliver the clip 390 to an inverted diverticulum 302 while the arms 392 are in the expanded configuration. The clip 390 can be placed at least partially within an inverted diverticulum 302, as illustrated in FIG. 47. The arms 392 can be of sufficient flexibility to allow them to pass into the opening of the diverticulum 302.

Figure 48:
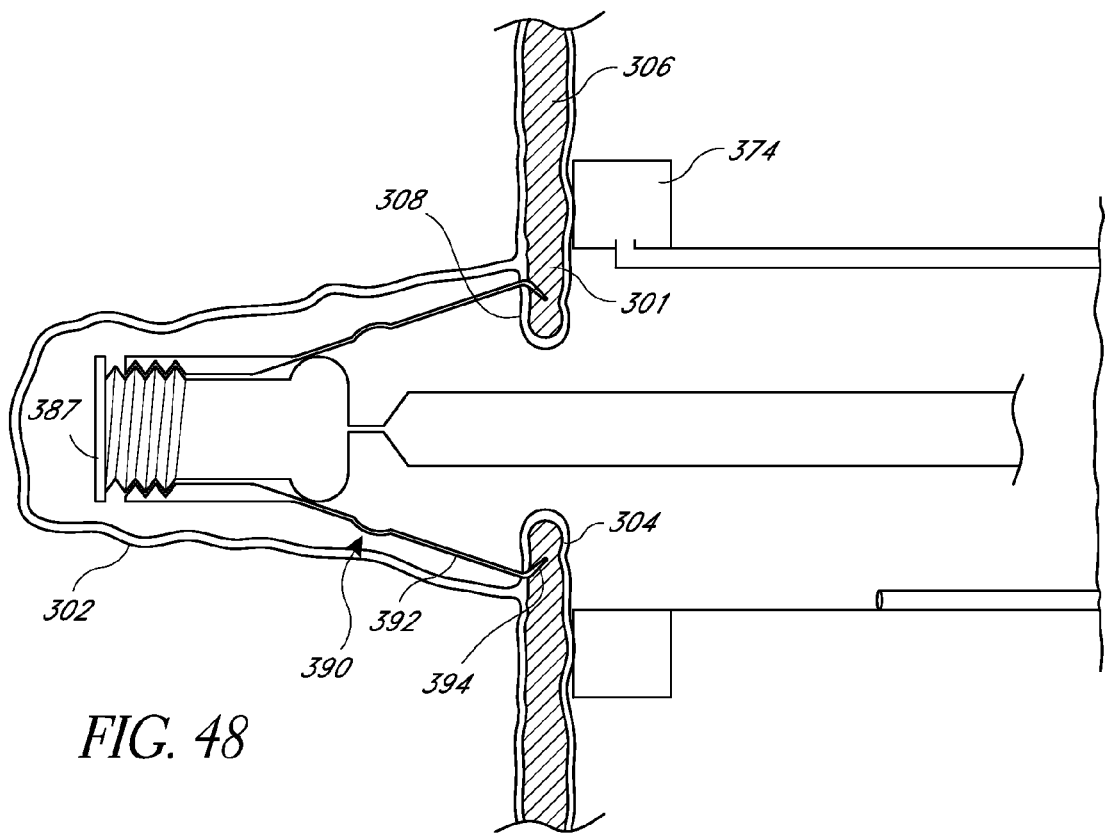
FIG. 48 is a cross-sectional view showing the tissue-engaging tips of the closure clip of the closure clip assembly of FIG. 46 engaging the colon wall surrounding the site of the opening to the inverted diverticulum.

FIG. 48 is a cross-sectional view showing the tissue-engaging tips 394 of the closure clip 390 of the closure clip assembly engaging the colon wall surrounding the site of the opening to the inverted diverticulum 302. Once the clip 390 is completely within the diverticulum 302, the arms 392 can expand back out toward the expanded configuration, the diverticulum 302 being forced wider. Upon beginning to pull the clip 390 proximally, for example by retracting the handle 382 proximally, the spikes 394 can catch along a portion 301 of the diverticulum 302. Alternatively, the arms 392 may not need to force the diverticulum 302 wider in order to catch or engage a portion 301 of the diverticulum 302 when proximally retracted. When engaged with the portion 301, the spikes 394 may extend into the muscularis 306 of the colon wall, although they may alternatively extend only into the mucosa 308.

With the spikes 394 engaged with the mucosa 308 and possibly the muscularis 306, the handle 382 of the closure clip deployment tool 380 can be rotated in a second direction (e.g., counter-clockwise) to proximally retract the tool 380 with respect to the clip 390. As the tool 380 retracts from the clip 390, the expander region 388 has a diminishing effect on the position of the arms 392, and the clip 390 can return closer to its initial shape as illustrated in FIG. 44. As the clip 390 contracts, the spikes 394 draw closer together, bringing the tissue 301 surrounding the diverticulum 302 with them to draw the mouth of the diverticulum 302 closed. FIG. 49 is a cross-sectional view showing the tissue-engaging tips 394 of the closure clip 390 of the closure clip assembly after closing the opening to the inverted diverticulum 302.

When the deployment tool 380 is screwed sufficiently into the clip 390 such that the expander region 388 generally coincides with the expander receiving area 398, the clip 390 can be in or almost in its initial shape, as illustrated in FIG. 49. Alternatively, the clip 390 and the deployment tool 380 can be configured to allow the clip 390 to reach its initial shape without the expander region 388 coinciding with the expander receiving area 398. As illustrated in FIG. 49, the spikes 394 are close enough to each other when the clip 390 is in the initial shape that the spikes 394 can draw the base of the diverticulum 302 generally closed. Once the diverticulum 302 is generally closed, the frangible portion 384 of the deployment tool 380 can be broken by twisting or otherwise manipulating the handle 382, and the portion of the deployment tool 380 proximal to the frangible portion 384 can be withdrawn, as also illustrated in FIG. 49. Once the deployment tool 380 has been withdrawn, the negative pressure applied to the flange 374 can be turned off, and the entire assembly can be removed. If another diverticulum 302 is somewhat proximate, the access port 370 can be repositioned, for example by being re-angled through the same entry point through the abdominal wall 305, and the procedure repeated on the next diverticulum with a different tool 380 and clip 390.

The clip 390 will hold the diverticulum 302 closed and allow the serosa 304 to heal and grow shut. Once the serosa 304 has grown shut, the diverticulum 302 and the clip 390 can be removed endoscopically using a RF snare, cautery wire, blade, or other removal implement, as is known in the art. Alternatively, the diverticulum 302 may necrose and fall off by itself, along with the clip 390. One advantage of closing a diverticulum 302 in this way is that it can leave nothing on the serosa 304 side of the colon that could cause adhesions.

Figure 50:
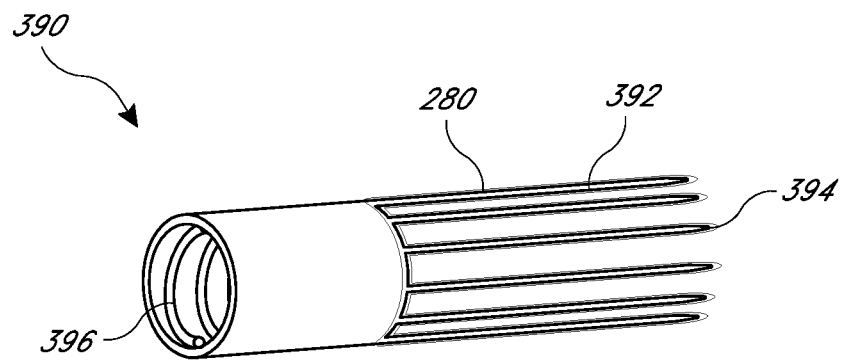
FIG. 50 is a perspective view of the closure clip of FIG. 43 including a drug coating.
Figure 51:
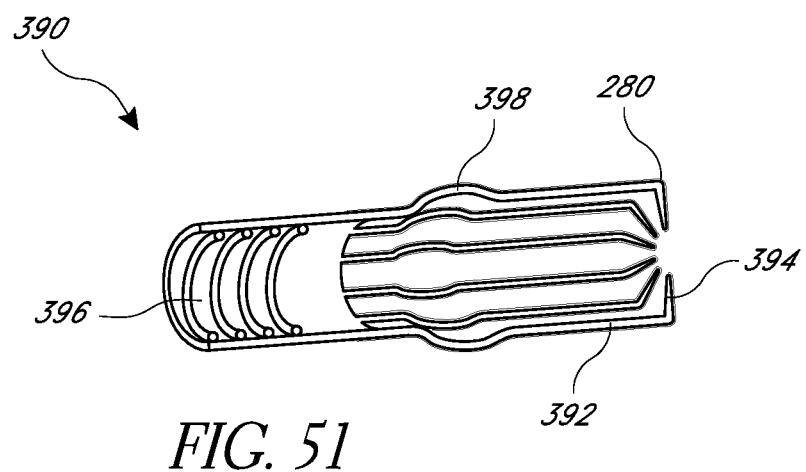
FIG. 51 is a cross-sectional view of the closure clip of FIG. 44 including a drug coating.

FIG. 50 is a perspective view of the closure clip 390 including a drug coating 280. FIG. 51 is a cross-sectional view of the closure clip 390 including a drug coating 280. As described above, the closure clip 390 illustrated in FIG. 51 may be the closure clip 390 illustrated in FIG. 50 in an expanded configuration, which can allow the tips 394 to orient radially inward and/or the expander receiving portion 398 to bulge radially outward. The clip 390 may include SMA such as nitinol or chromium cobalt, or a metal such as stainless steel. Coating the clip 390 with a drug coating may be in accordance with methods known in the art, such as direct attachment (e.g., with or without surface treatment), embedding in a polymer layer, and the like. The closure clip 390 may include the drug coating 280 over the tips 394, the arms 392, and a distal portion. The drug coating 280 may be at least on a portion of the clip 390 that contacts the tissue 301 of the diverticulum 302.

Various polymers can help control the elution rate of the drug and/or allow the coating to include multiple drugs (e.g., both coagulants and antibiotics). The drug coating may include antibiotics to inhibit or prevent infection while the injured tissue is healing and/or coagulation modifiers to reduce or minimize blood loss and promote rapid healing, for example including the drugs described above.

Figure 52:
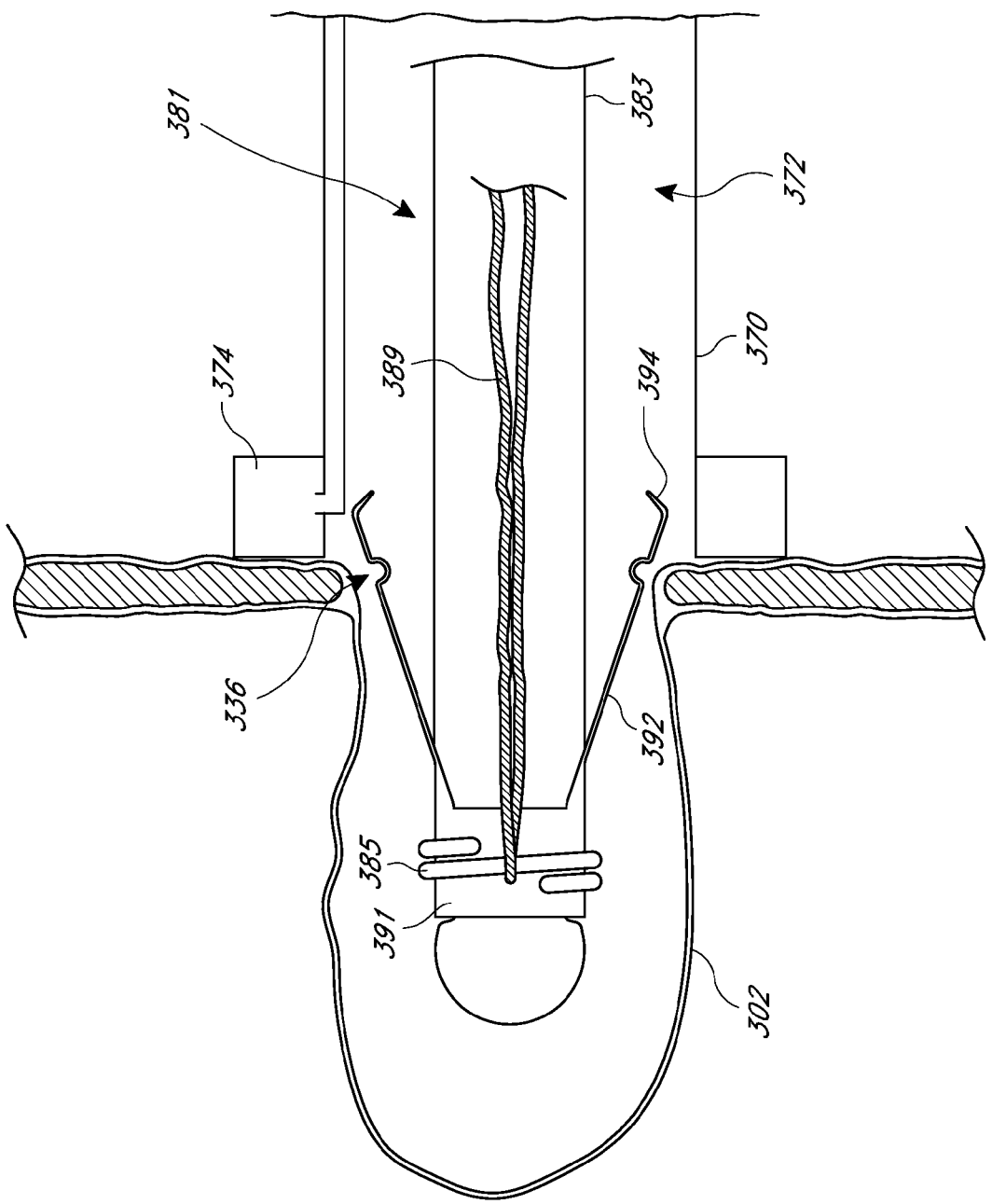
FIG. 52 is a partial cross-sectional view showing another closure clip assembly at least partially within an inverted diverticulum, the closure clip assembly including a closure clip and a deployment tool, the closure clip including a distal region and a plurality of closure arms extending proximally from the distal region, the plurality of closure arms including tissue-engaging tips bias radially inward, the deployment tool including a shaft, a spring ring over the closure clip, and a pulling mechanism.

FIG. 52 is a partial cross-sectional view showing another closure clip assembly at least partially within an inverted diverticulum 302. The closure clip assembly including a closure clip 391 and a deployment tool 381. The closure clip 391 includes a distal region and a plurality of closure arms 392 extending proximally from the distal region. The plurality of closure arms 392 include tissue-engaging tips 394 biased radially inward. Unlike the clip 390, in which the arms 392 are biased radially inward, the arms 392 of the clip 391 are biased radially outward. The arms 392 include detents 336 proximate and proximal to the tips 394. Portions of the clip 391 may include a drug coating, for example as described above with respect to the clip 390.

The deployment tool 381 includes a shaft or pusher 383, a spring ring 385 over the closure clip 391, and a pulling mechanism 389. The spring ring 385 can be similar to the spring ring 282 described above, for example including an arcuate coil of SMA. The pulling mechanism 389 illustrated in FIG. 52 includes a suture material extending from a proximal end, into the interior of the spring ring 385, around the distal end of the spring ring 385 to the outside of the spring ring 385, and extending back to the proximal end.

As illustrated in FIG. 52, the assembly has been inserted through a working lumen 372 of an access port 370 including a flange 374. Negative pressure has been applied to the flange 374 and positive pressure has been applied to the working lumen 372, as described above, to invert the diverticulum 302. Alternatively, the distal end of the deployment tool 381 may be atraumatic (e.g., rounded) such that the diverticulum 302 can be inverted by pushing the diverticulum 302 with the deployment tool 381. The deployment tool 380 described above may also include an atraumatic distal end (e.g., distal to the stop 387) such that the diverticulum 302 can be inverted by pushing the diverticulum 302 with the deployment tool 380.

The deployment tool 381 can deliver the clip 391 to an inverted diverticulum 302 while the arms 392 are expanded. The clip 391 can be placed at least partially within an inverted diverticulum 302, as illustrated in FIG. 52. The arms 392 can be of sufficient flexibility to allow them to pass into the opening of the diverticulum 302.

Figure 53:
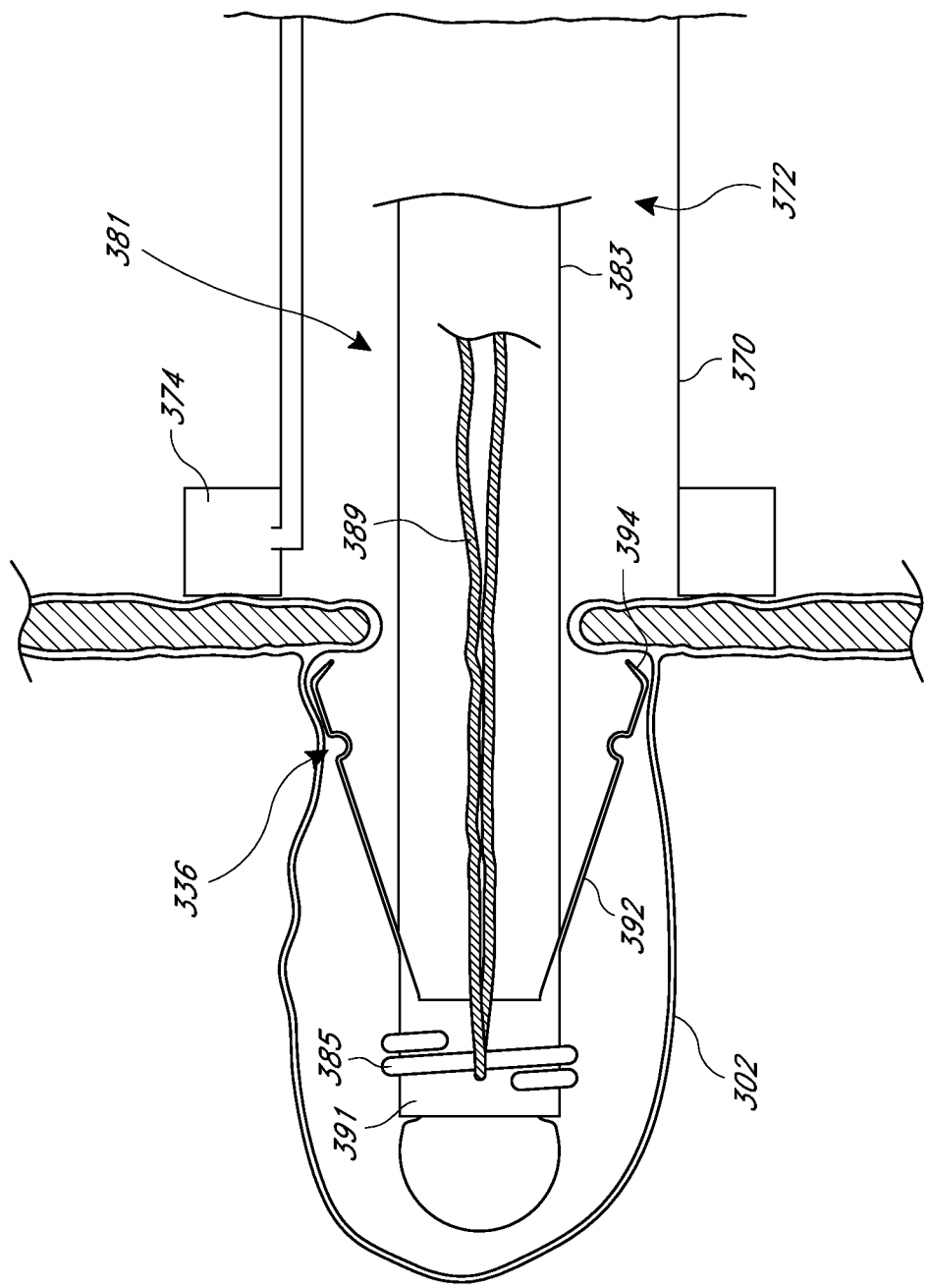
FIG. 53 is a partial cross-sectional view showing the tissue-engaging tips of the closure clip of the closure clip assembly of FIG. 52 engaging the colon wall surrounding the site of the opening to the inverted diverticulum.

FIG. 53 is a partial cross-sectional view showing the tissue-engaging tips 394 of the closure clip 391 of the closure clip assembly engaging the colon wall surrounding the site of the opening to the inverted diverticulum 302. Once the clip 391 is completely within the diverticulum 302, the arms 392 can expand back out toward the expanded configuration, the diverticulum 302 being forced wider. Upon beginning to pull the clip 391 proximally, the spikes 394 can catch along a portion of the diverticulum 302. Alternatively, the arms 392 may not need to force the diverticulum 302 wider in order to catch or engage a portion of the diverticulum 302 when proximally retracted. When engaged with the portion, the spikes 394 may extend into the muscularis of the colon wall, although they may alternatively extend only into the mucosa, as described above. Once the clip 391 is completely within the diverticulum 302, the shaft 383 can be withdrawn.

Figure 54:
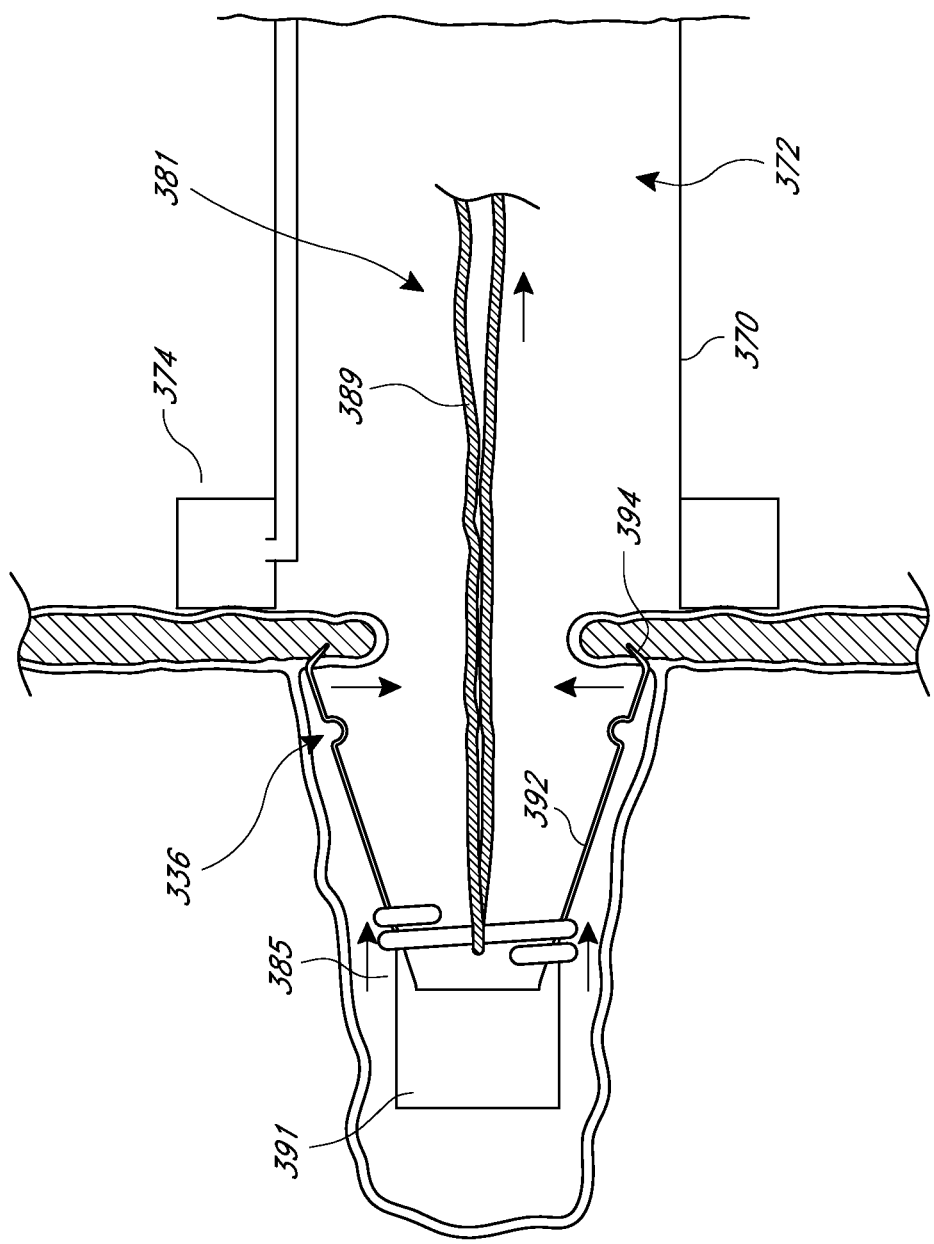
FIG. 54 is a partial cross-sectional view showing the tissue-engaging tips of the closure clip of the closure clip assembly of FIG. 52 during closing the opening to the inverted diverticulum as the spring ring is proximally retracted.
Figure 55:
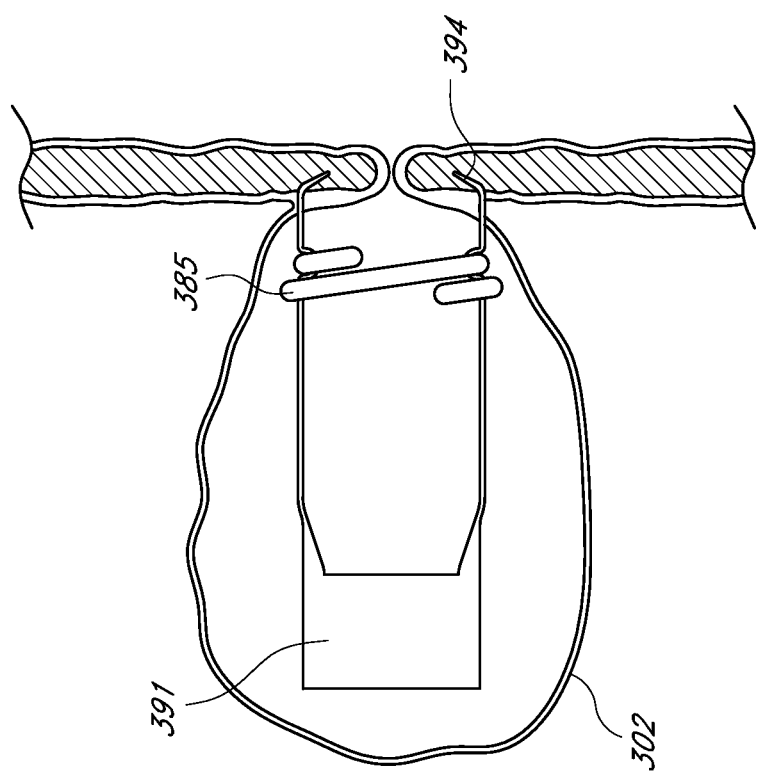
FIG. 55 is a partial cross-sectional view showing the tissue-engaging tips of the closure clip of the closure clip assembly of FIG. 52 after closing the opening to the inverted diverticulum, the spring ring over a proximal portion of the closure clip and around the neck of an inverted diverticulum.

FIG. 54 is a partial cross-sectional view showing the tissue-engaging tips 394 of the closure clip 391 of the closure clip assembly during closing the opening to the inverted diverticulum 302 as the spring ring 385 is proximally retracted. As the spring ring 385 is proximally retracted, for example by proximally retracting both ends of the suture material of the pulling mechanism 389, the spring ring 385 advances over the arms 392 of the clip 391, compressing the arms 392 radially inward. As the arms 392 of the clip 391 contract, the spikes 394 draw closer together, bringing the tissue surrounding the diverticulum 302 with them to draw the mouth of the diverticulum 302 closed. FIG. 55 is a partial cross-sectional view showing the tissue-engaging tips 394 of the closure clip 391 of the closure clip assembly after closing the opening to the inverted diverticulum 302. The spring ring 385 is over a proximal portion of the closure clip 391, for example in the detents 336, and around the neck of the inverted diverticulum 302.

Once the diverticulum 302 is generally closed, one end of the suture material of the pulling mechanism 389 may be pulled, unthreading the pulling mechanism 389 from the spring ring 385, thereby only leaving the clip 391 and the spring ring 385 in the closed and inverted diverticulum 302. Once the remaining components of the deployment tool 381 have been withdrawn, the negative pressure applied to the flange 374 can be turned off, and the entire assembly can be removed or another diverticulum 302 may be treated, for example using another clip 390, 391.

The clip 391 and the spring ring 385 will hold the diverticulum 302 closed and allow the serosa to heal and grow shut. Once the serosa has grown shut, the diverticulum 302, the clip 391, and the spring ring 385 can be removed endoscopically using a RF snare, cautery wire, blade, or other removal implement, as is known in the art. Alternatively, the diverticulum 302 may necrose and fall off by itself, along with the clip 391 and the spring ring 385. One advantage of closing a diverticulum 302 in this way is that it can leave nothing on the serosa 304 side of the colon that could cause adhesions. Another advantage of a clip 391 and a spring ring 385 is that the cost of the assembly may be reduced, for example for the reasons described above.

Figure 56:
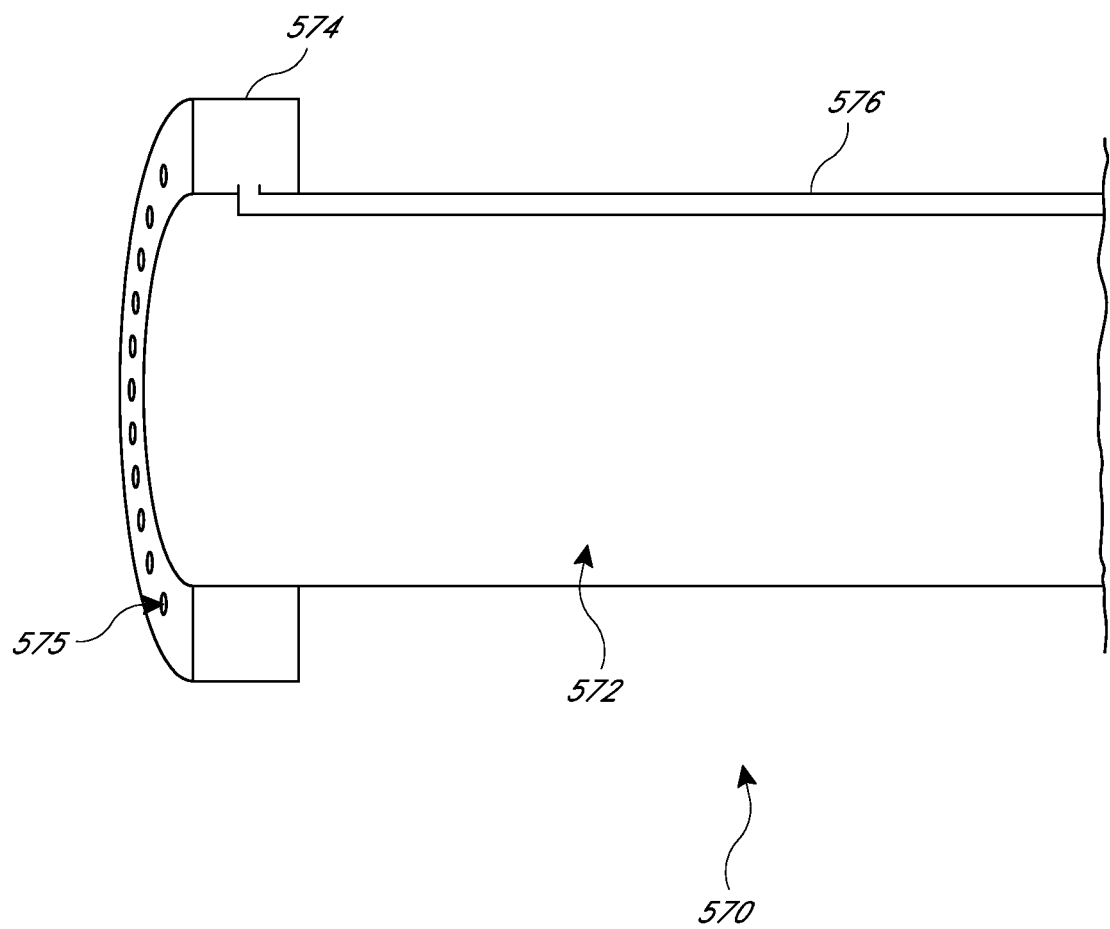
FIG. 56 is a perspective cross-sectional view of a laparoscopic access port including a distal end including a hollow suction flange, the hollow suction flange coupled to a negative pressure line.

FIG. 56 is a perspective cross-sectional view of a laparoscopic access port 570 including a distal end including a hollow suction flange 574. The hollow suction flange 574 is coupled to a negative pressure line 576. The access port 570 includes a working channel 572. The working channel 572 can be a hollow tube. The working channel 572 may be accessible at a proximal end to a person using the access port 570, and extends all the way to the distal end of the access port 570. The access port 570 may include a distal portion including a hollow flange 374. The hollow flange 574 may include a plurality of holes 575 along a distal surface. The hollow flange 574 can be in fluid communication with a negative pressure line 576. The hollow flange 574 may surround the entire circumference of the working channel 572, and can have a diameter on the order of about two centimeters. Alternatively, the diameter can be larger or smaller, depending on the diverticulum or other lesion sought to be treated. The hollow flange 574 should be at least slightly larger than any diverticulum sought to be inverted.

Figure 57:
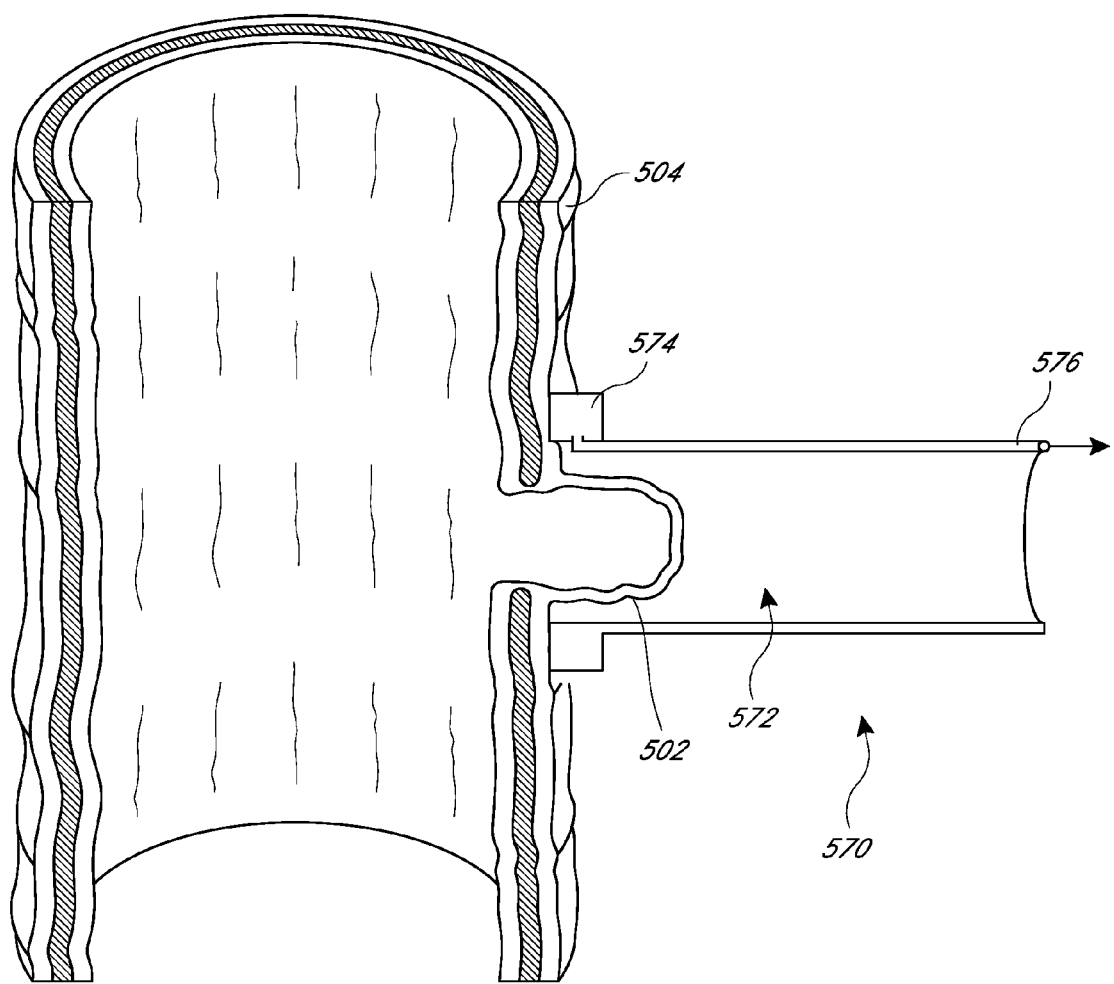
FIG. 57 is a perspective cross-sectional view of the laparoscopic access port of FIG. 56 and a diverticulum extending into the access port from a wall of a colon.

FIG. 57 is a perspective cross-sectional view of the laparoscopic access port 570 and a diverticulum 502 extending into the access port 570 from a wall of a colon. The flange 574 can be positioned substantially flush against the tissue surrounding the diverticulum 502—in the case of a colonic diverticulum 502, the flange 574 may be substantially flush against the serosa 504. Any imaging device known in the art can be used to help locate the diverticulum 502 and appropriately position the access port 570. The imaging device can be included within the working channel 572 of the access port 570 or used separately from the access port 570. Additionally, if desired, the light of a colonoscope within the colon can help guide the access port 570 toward the diverticulum 502 being treated.

Once the access port 570 is in place against the tissue surrounding the diverticulum 502, the negative pressure line 576 can be activated, creating a negative pressure in the flange 574 and a suction fit between the holes 575 (FIG. 56) and the tissue surrounding the diverticulum 502. The suction fit can create a substantially airtight seal between the flange 574 and the serosa 504. With a substantially airtight seal in place, and good contact between the flange 574 and the tissue surrounding the diverticulum 502, the diverticulum 502 may be at least partially inverted, for example by applying a positive pressure to the working lumen 572 or by pushing with an atraumatic device.

Figure 58:
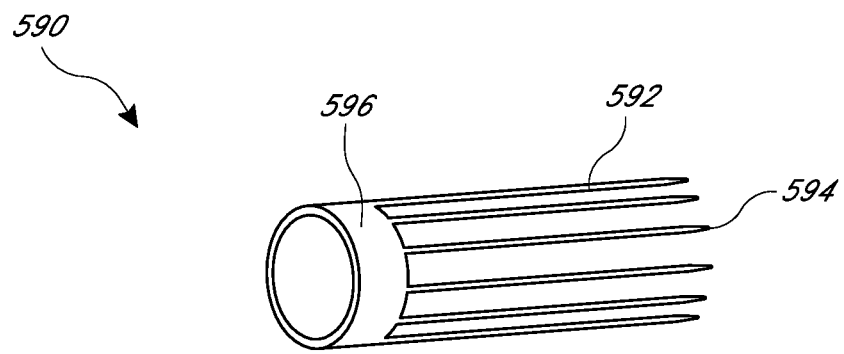
FIG. 58 is a perspective view of a closure clip including a distal region and a plurality of closure arms extending proximally from the distal region.
Figure 59:
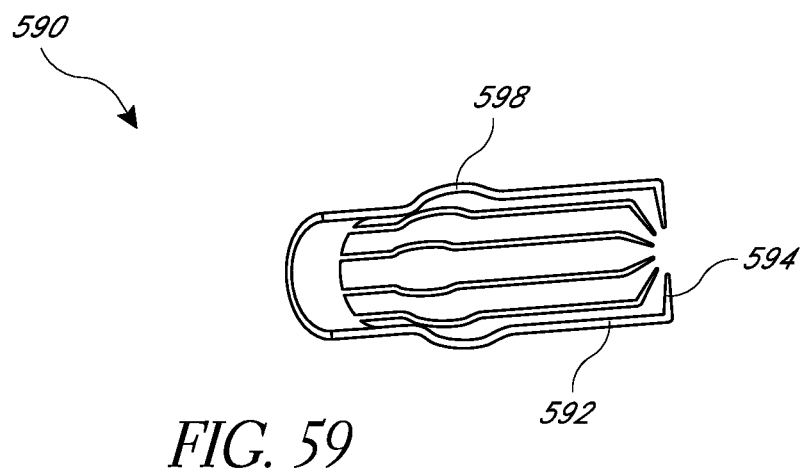
FIG. 59 is a cross-sectional view of a closure clip including a distal region and a plurality of closure arms extending proximally from the distal region, the plurality of closure arms including tissue-engaging tips of the arms biased radially inward.

FIG. 58 is a perspective view of a closure clip 590 including a distal region 596 and a plurality of closure arms 592 extending proximally from the distal region 596. The clip 590 may include a hypotube that is cut to form the plurality of closure arms 592 and spikes 594 at a proximal end of the clip 590. FIG. 59 is a cross-sectional view of a closure clip 590 including a distal region 596 and a plurality of closure arms 592 extending proximally from the distal region 596. The plurality of closure arms 592 include expander receiving areas 598 and tissue-engaging tips 594 biased radially inward. The clip 590 illustrated in FIG. 58 may assume the shape of the clip 590 illustrated in FIG. 59 when the clip 590 is not restrained, for example by a deployment tool. In FIG. 59, the proximal ends of the arms 592 are bent radially inward. Alternatively, just the spikes 594 may be bent inward.

FIG. 60 is a cross-sectional view of a deployment tool 549 including a distal expandable member 550 and a proximal expandable member 551. The expandable members 550, 551 are coupled to separate inflation lumens 552, 553, and can be independently inflated and deflated with fluid such as liquid or air, for example from a source connected to the lumens 552, 553, for example via Luer fittings. The expandable members 550, 551 may share features with angioplasty balloons, such as including polymer such as polyether block amide.

Figure 62:
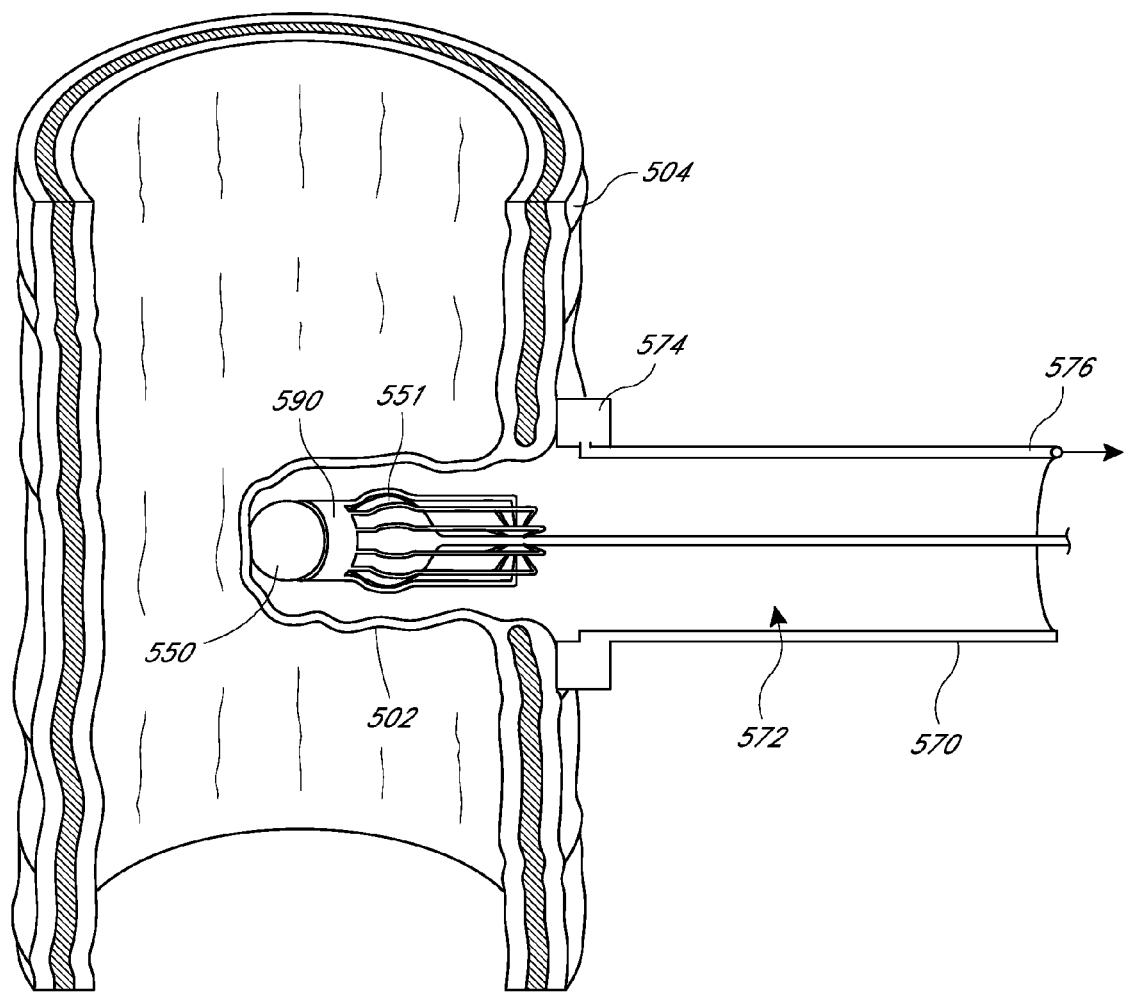
FIG. 62 is a partial cross-sectional view showing the closure clip assembly of FIG. 61 at least partially within an inverted diverticulum.

FIG. 61 is a perspective view of a closure clip assembly including the deployment tool 549 over the closure clip 590. The deployment tool 549 can be positioned relative to the clip 590 such that the proximal expandable member 551 is relatively aligned with the expander receiving areas 598. The proximal expandable member 551 may be partially inflated until the edges of the proximal expandable member contact the expander receiving areas, but not enough to cause the arms 592 to radially outwardly expand. The deployment tool 549 can deliver the clip 590 to an inverted diverticulum 502. The clip 590 can be placed at least partially within an inverted diverticulum 502, as illustrated in FIG. 62. The diverticulum 502 can be inverted by applying positive pressure to the working lumen 572 of the access port 570. The diverticulum 502 may be inverted by pushing on the diverticulum 502 with the distal expandable member 550 inflated, which can provide the assembly with an atraumatic soft contact area at the distal end.

Figure 63:
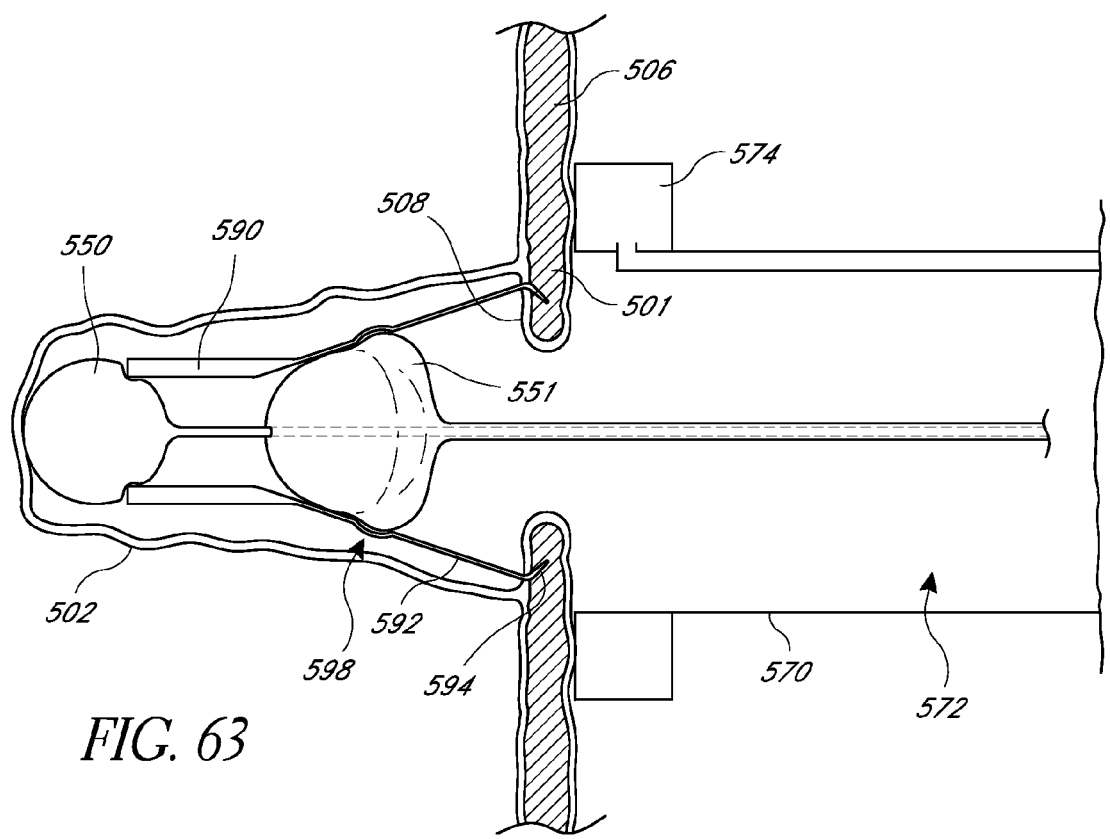
FIG. 63 is a cross-sectional view showing the tissue-engaging tips of the closure clip of the closure clip assembly of FIG. 62 engaging the colon wall surrounding the site of the opening to the inverted diverticulum.

FIG. 63 is a cross-sectional view showing the tissue-engaging tips 594 of the closure clip 590 of the closure clip assembly engaging the colon wall surrounding the site of the opening to the inverted diverticulum 502. Once the clip 590 is completely within the diverticulum 502, the proximal expandable member 551 may be inflated to cause the arms 592 to expand radially outward, which can force the diverticulum 502 wider. Upon beginning to pull the clip 590 proximally, for example by retracting the deployment tool 549, the spikes 594 can catch along a portion 501 of the diverticulum 502. Alternatively, the arms 592 may not need to force the diverticulum 502 wider in order to catch or engage a portion 501 of the diverticulum 502 when proximally retracted. When engaged with the portion 501, the spikes 594 may extend into the muscularis 506 of the colon wall, although they may alternatively extend only into the mucosa 508.

Figure 64:
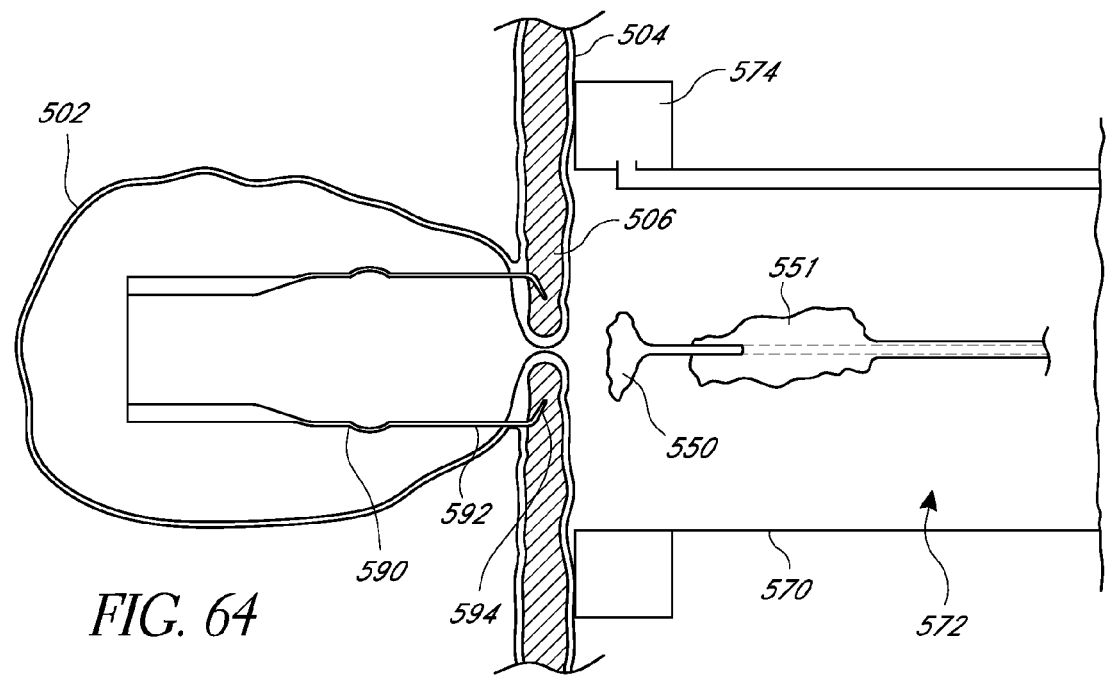
FIG. 64 is a cross-sectional view showing the tissue-engaging tips of the closure clip of the closure clip assembly of FIG. 62 after closing the opening to the inverted diverticulum and withdrawing the deployment tool out of the closed diverticulum.

With the spikes 594 engaged with the mucosa 508 and possibly the muscularis 506, the proximal inflatable element 551 may be deflated. As the proximal inflatable element 551 is deflated, the proximal inflatable element 551 has a diminishing effect on the position of the arms 592, and the clip 590 can return closer to its initial shape as illustrated in FIG. 59. As the clip 590 contracts, the spikes 594 draw closer together, bringing the tissue 501 surrounding the diverticulum 502 with them to draw the mouth of the diverticulum 502 closed. FIG. 64 is a cross-sectional view showing the tissue-engaging tips 594 of the closure clip 590 of the closure clip assembly after closing the opening to the inverted diverticulum 502 and withdrawing the deployment tool 549 out of the closed diverticulum 502. Prior to withdrawing the deployment tool 549, the inflatable elements 550, 551 may be deflated to allow them to fit through the clip 590 and the mouth of the diverticulum 502.

The clip 590 will hold the diverticulum 502 closed and allow the serosa 504 to heal and grow shut. Once the serosa 504 has grown shut, the diverticulum 502 and the clip 590 can be removed endoscopically using a RF snare, cautery wire, blade, or other removal implement, as is known in the art. Alternatively, the diverticulum 502 may necrose and fall off by itself, along with the clip 590. One advantage of closing a diverticulum 502 in this way is that it can leave nothing on the serosa 504 side of the colon that could cause adhesions.

Figure 65:
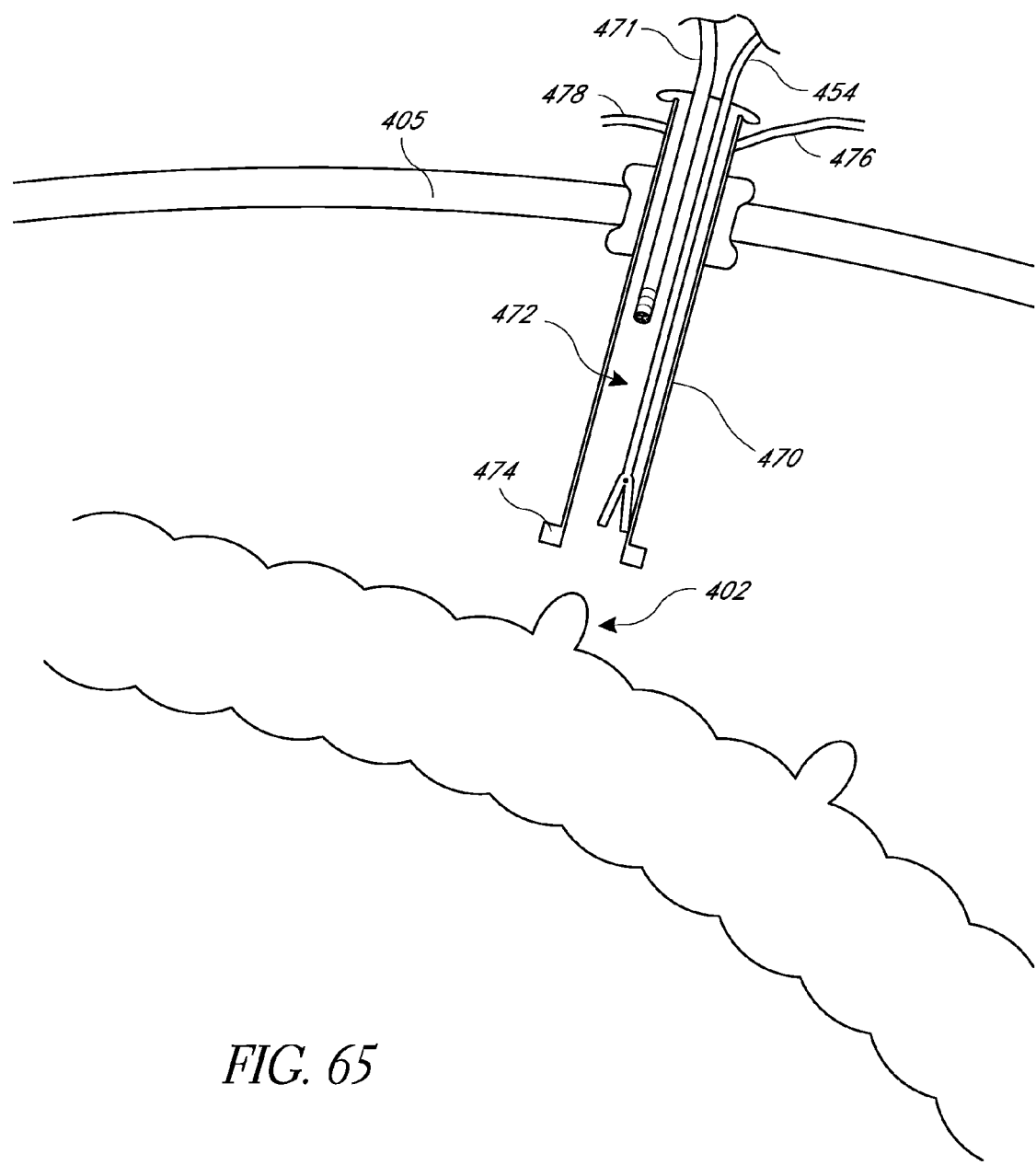
FIG. 65 is a partial cross-sectional view of a laparoscopic device including a laparoscopic access port, and a scope and a suturing tool deployed within the laparoscopic access port, a distal end of the laparoscopic device proximate to a diverticulum.

FIGS. 65-70 illustrate an alternative method of closing a diverticulum that has been inverted with a laparoscopic diverticulum inverting device. FIG. 65 is a partial cross-sectional view of a laparoscopic device including a laparoscopic access port 470, and a scope 471 and a suturing tool 454 within the laparoscopic access portion 470. A distal end of the laparoscopic access port 470 is proximate to a diverticulum 402. The laparoscopic device is roughly analogous to the embodiment illustrated in FIG. 42. The laparoscopic device 470 has been inserted through the abdominal wall 405 and is adjacent a diverticulum 402. However, rather than including a closure clip deployment tool 380, or other closure clip deployment tools described above, positioned within the working channel 472 of the access port 470, a suturing device 454 can be positioned within the working channel 472 of the access port 470. The suturing device 454 can be any laparoscopic suturing device known in the art, such as the ENDO STICH® device, available from Covidien of Mansfield, Mass. Neither here, nor as described with respect to FIGS. 42-64, is it necessary to position the device used to close the diverticulum within the working channel before the diverticulum is inverted. Positioning the device used to close the diverticulum in the working channel in advance, however, can improve the efficiency of the procedure.

Figure 66:
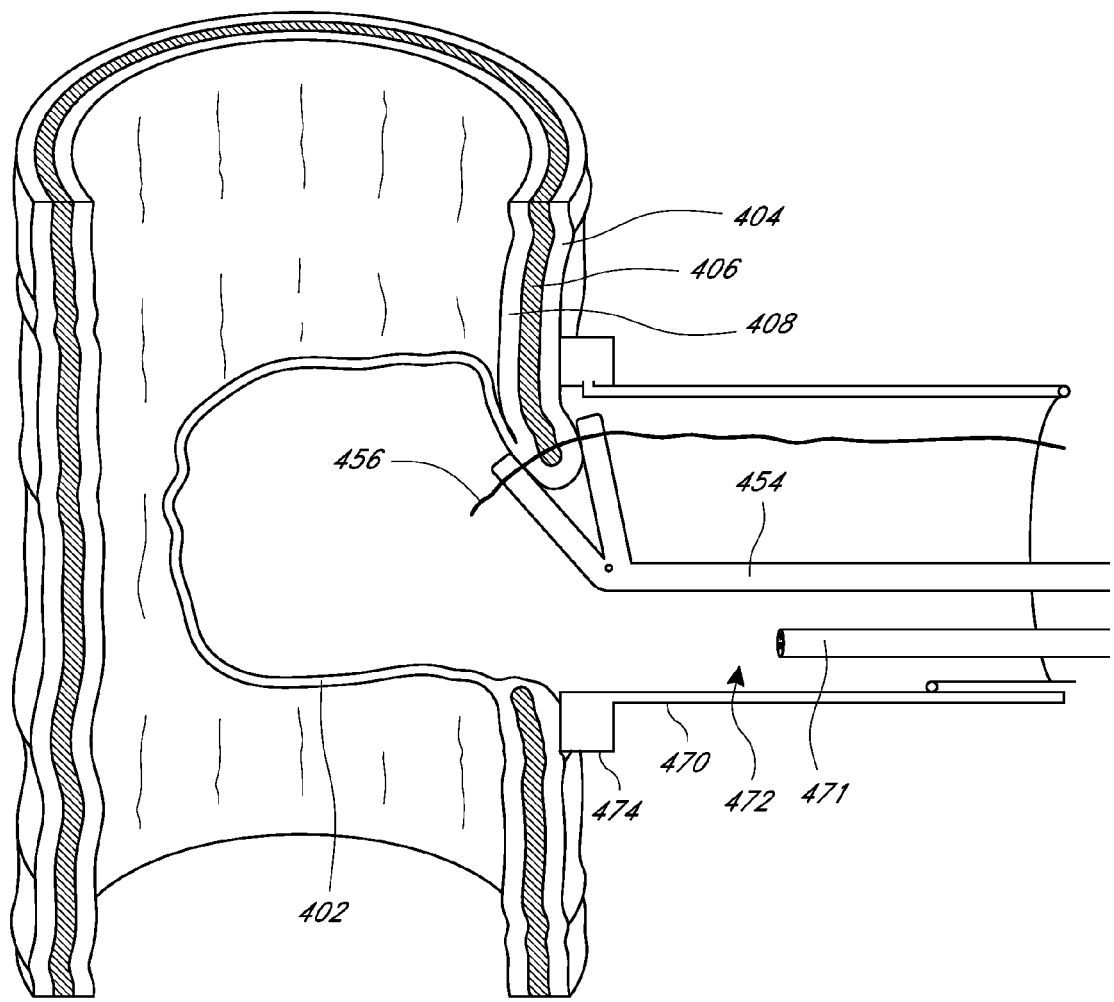
FIG. 66 is a partial cross-sectional view showing the suturing tool of the laparoscopic device of FIG. 65 passing a suture through a wall of a colon on one side of an opening to an inverted diverticulum.
Figure 67:
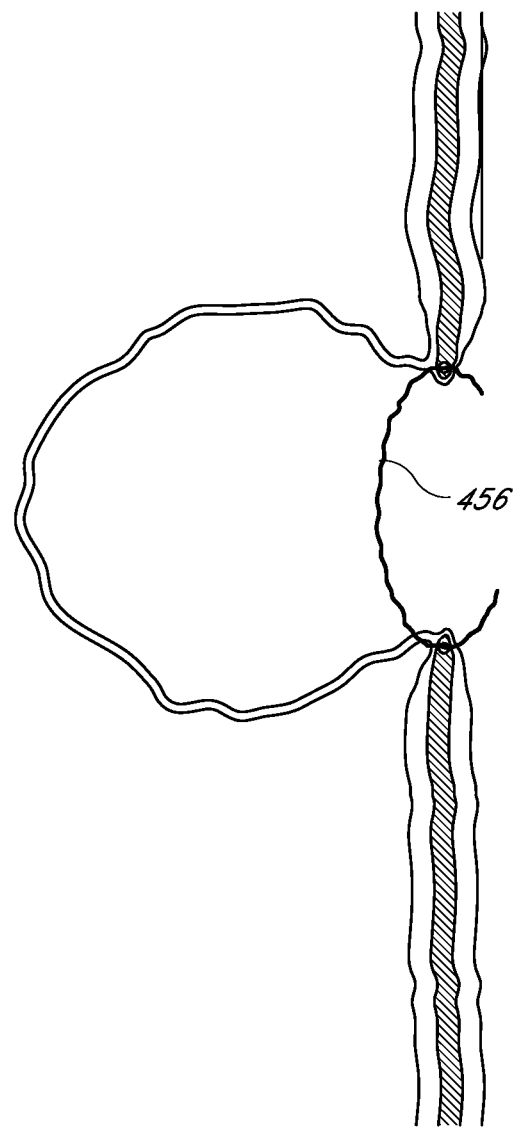
FIG. 67 is a partial cross-sectional view showing the suture of FIG. 66 after being passed through another wall of the colon on the other side of the opening to the inverted diverticulum.

FIG. 66 is a partial cross-sectional view showing the suturing tool 454 of the laparoscopic device passing a suture through a wall of a colon on one side of an inverted diverticulum 402 has been inverted. The suturing tool 454 can grasp the base of the diverticulum 402 and may pass a suture 456 through the serosa 404, the muscularis 406, and the mucosa 408 layers. Alternatively, the suturing tool 454 can pass a suture 456 through just one or two of the serosa 404, the muscularis 406, and the mucosa 408. The suturing tool 454 can then be moved to another side of the diverticulum 402, grasp the base again, and provide another suture as shown in FIG. 67. These steps can be repeated as is well known in the art until the diverticulum 402 is enclosed with a series of sutures.

Figure 68:
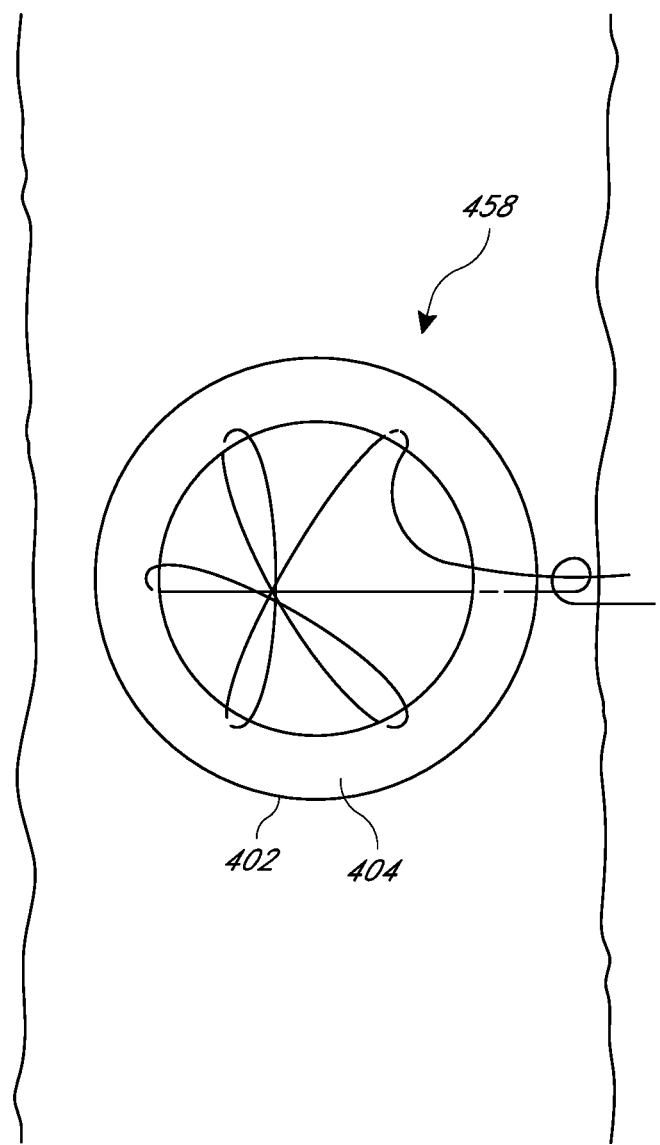
FIG. 68 is a top view showing a suture pattern that may be used to tie off the opening of an inverted diverticulum.
Figure 69:
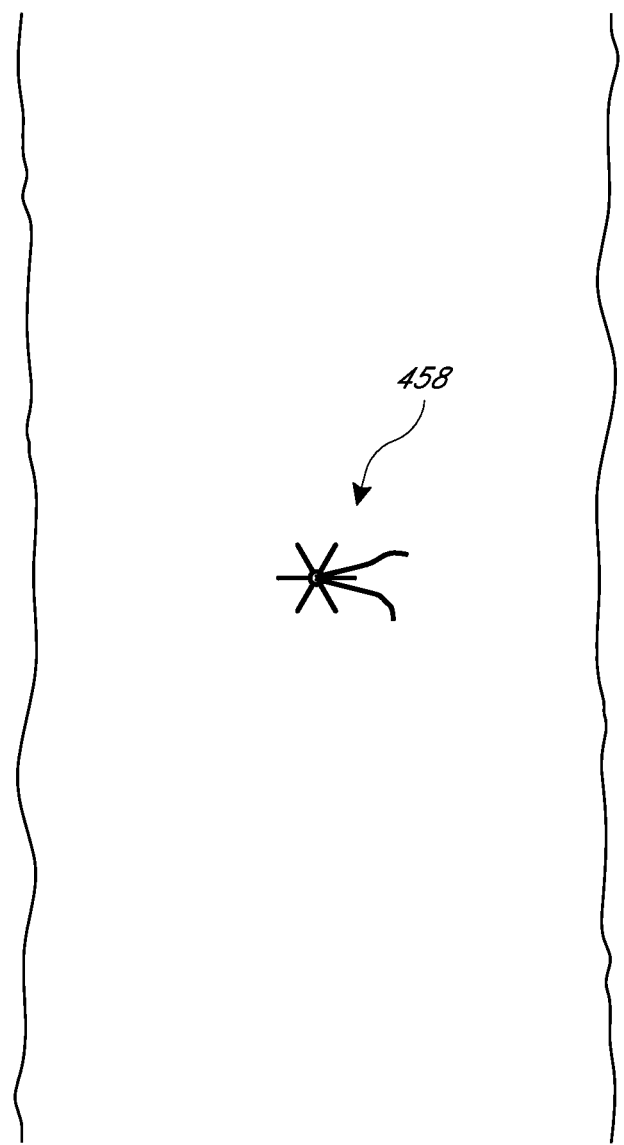
FIG. 69 is a top view showing the diverticulum closed by tightening the suture of FIG. 68.

Any number of suturing techniques may be used. For example, FIG. 68 is a top view showing a suture pattern that may be used to tie off the opening on an inverted diverticulum 402. In FIG. 68, the serosa 404 is engaged by a purse string suture 458. A purse string suture 458 can be beneficial because it draws the surfaces of the serosa 404 together, promoting a natural healing of the opening of the diverticulum 402. FIG. 69 is a top view showing the diverticulum 402 closed by tightening the suture 458. The scope 471, visible in FIG. 65, can be used to help with the suturing process and confirm that the diverticulum 402 has been properly closed.

Figure 70:
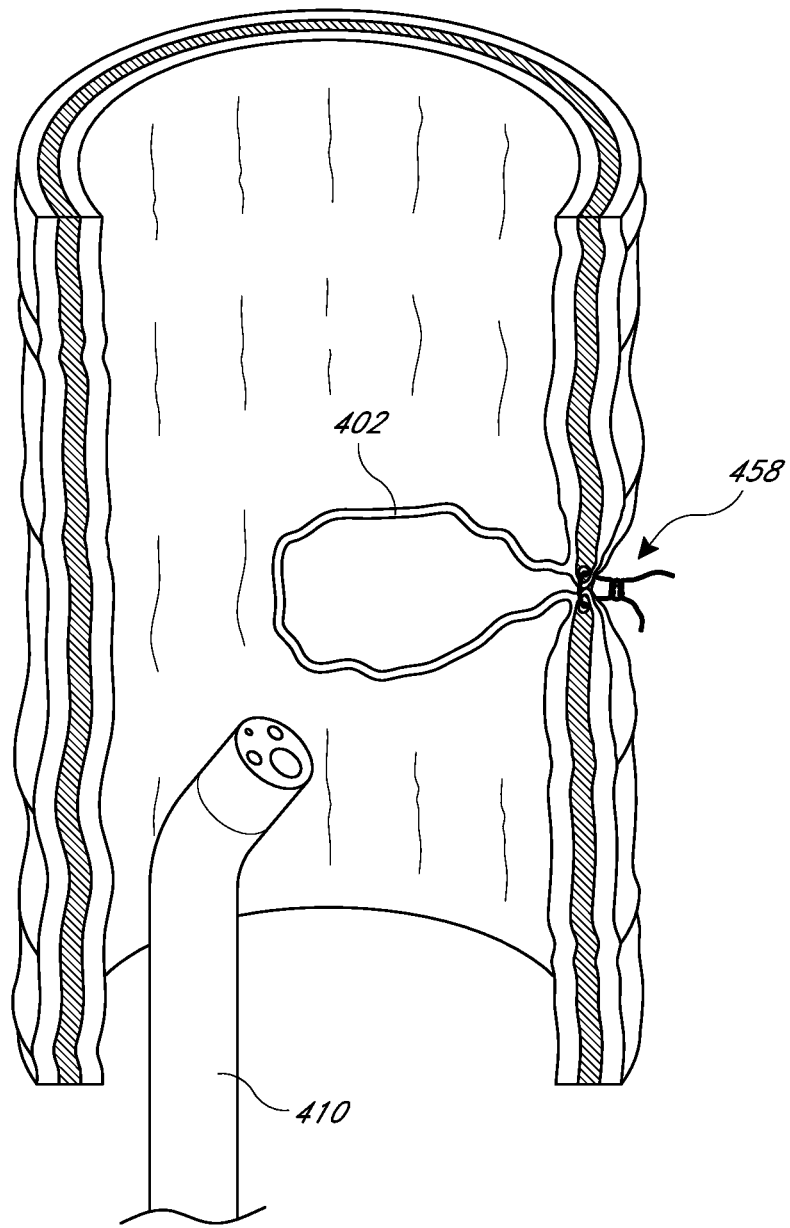
FIG. 70 is a partial cross-sectional view showing a diverticulum closed by a suture being examined by a colonoscope.

FIG. 70 is a partial cross-sectional view showing a diverticulum 402 closed by a suture 458 being examined by a colonoscope 410. The diverticulum 402 can be visually examined with a scope 410, alone or in addition to the scope 471. Once closed, the diverticulum 402 can be allowed to necrose and slough off, or it can be removed endoscopically using a RF snare, cautery wire, blade, or other removal implement, as is known in the art.

While the description generally refers to colonoscopes and treatments within a colon, the devices and methods described herein are not limited to applications within a colon. They can be used to invert and/or treat outpocketings (e.g., diverticula, aneurisms, etc.) in any body lumen. Any reference to a colonoscope should be understood to be applicable to endoscopes generally, and similarly, any reference to a colon should be understood to be applicable to any body lumen.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "between," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration, and are not intended to be limiting, with the true scope and spirit being indicated by the following claims.

EXAMPLE EMBODIMENTS

1. A device for treating a diverticulum, the device comprising:
   a basket having a first shape wherein the basket is advanceable through a catheter lumen and a second shape upon expansion within a body lumen, the basket operable in the first shape, the second shape, or any intermediate shape between the first shape and the second shape, the basket comprising:
      a plurality of ribs including distal ends defining a distal rim of the basket, the plurality of ribs configured to engage tissue of the body lumen proximate to an opening of a diverticulum; and
      an outer polymeric film;
   a closing component positionable around the basket; and
   a tubular member fluidly connected to the basket, the tubular member connectable to a source of negative pressure, wherein the diverticulum is invertible at least partially into the basket upon application of a negative pressure through the tubular member.

2. The device of Embodiment 1, wherein the body lumen is a colon.

3. The device of Embodiment 1 or 2, wherein the basket in the second shape is sized to receive an inverted diverticulum.

4. The device of any of Embodiments 1-3, wherein a colonoscope comprises the catheter lumen.

5. The device of any of Embodiments 1-4, wherein the closing component operates between a first shape, a second shape, and any intermediate shape between the first shape and the second shape.

6. The device of any of Embodiments 1-5, wherein the plurality of ribs extend distally from a shared hub.

7. The device of any of Embodiments 1-6, wherein the distal rim of the basket comprises a plurality of spikes.

8. The device of any of Embodiments 1-7, wherein the closing component includes a closable loop.

9. The device of Embodiment 8, wherein the closable loop is configured to release from a position around the basket when tightened.

10. The device of Embodiment 8 or 9, wherein a portion of the basket around which the closable loop is inwardly angled to assist release of the closable loop.

11. The device of any of Embodiments 8-10, wherein the closable loop comprises a suture material.

12. The device of Embodiment 11, wherein the suture material comprises a resorbable suture material.

13. The device of Embodiment 12, wherein the suture material is resorbable.

14. The device of any of Embodiments 8-13, further comprising a knot pusher.

15. The device of any of Embodiments 8-14, wherein the closable loop comprises two stops spaced by a distance along the closable loop.

16. The device of Embodiment 15, wherein the distance is between about 6 millimeters and about 12 millimeters.

17. The device of any of Embodiments 8-16, wherein the closable loop is releasably bonded to the outer polymeric film.

18. The device of Embodiment 17, wherein the releasable bond is releasable upon tightening the closable loop to allow the closable loop to release from a position around the basket.

19. The device of any of Embodiments 1-18, further comprising a delivery sheath configured to slide coaxially over the basket, wherein the closing component includes a closure clip coaxially over the delivery sheath.

20. The device of Embodiment 19, wherein the closure clip has a first shape over the delivery sheath and a second shape when moved off of the delivery sheath.

21. The device of Embodiment 20, wherein the second shape is sized such that, when the closure clip is positioned around the diverticulum, the closure clip draws serosa at the opening to the diverticulum into contact with the serosa.

22. The device of any of Embodiments 19-21, wherein the closure clip comprises a distal end including pointed elements.

23. The device of Embodiment 22, wherein the pointed elements are configured to turn radially inward when the closure clip is in the second shape.

24. The device of Embodiment 22 or 23, wherein the closing component comprises a plurality of closure clips each comprising a proximal end including recesses configured to complement the pointed elements when the closure clips are in the first shape.

25. The device of any of Embodiments 19-24, wherein the delivery sheath includes a radially expandable distal end.

26. The device of any of Embodiments 19-25, further comprising a pusher device configured to move the closure clip.

27. The device of Embodiment 26, wherein the pusher device includes a radially expandable distal end.

28. The device of Embodiment 26 or 27, wherein the pusher device includes a plurality of distally extending elements including bent tips engaged with a distal-most closure clip.

29. The device of any of Embodiments 1-18, further comprising a first pusher and a second pusher coaxially over the first pusher, wherein the closing component includes a spring ring coaxially over the first pusher and distal to the second pusher.

30. The device of Embodiment 29, wherein the plurality of ribs include detents proximate to the distal rim and configured to engage the spring ring.

31. The device of Embodiment 29 or 30, wherein the basket is releasably coupled to the first pusher.

32. The device of any of Embodiments 1-31, wherein the closing component comprises a shape memory material.

33. The device of any of Embodiments 1-32, wherein at least one of the closing component and the basket includes a drug coating.

34. The device of Embodiment 33, wherein the drug coating includes at least one of a coagulation modifier and an antibiotic.

35. The device of Embodiment 33 or 34, wherein the closing component includes the drug coating.

36. The device of Embodiment 35, wherein a distal end of the closing component includes a closure clip including a distal end comprising the drug coating.

37. The device of any of Embodiments 33-36, wherein the distal ends of the plurality of ribs comprise the drug coating.

38. A device for treating a diverticulum, the device comprising:
   a basket having a first shape wherein the basket is advanceable through a catheter lumen and a second shape sized to at least partially receive an inverted diverticulum upon deployment at a site within a body lumen, the basket comprising a distal rim configured to engage tissue of a body lumen surrounding an opening to a diverticulum, the basket operable in the first shape, the second shape, or any intermediate shape between the first shape and the second shape; and
   a closing component positionable around the basket.

39. The device of Embodiment 38, wherein the body lumen is a colon.

40. The device of Embodiment 38 or 39, wherein a colonoscope comprises the catheter lumen.

41. The device of any of Embodiments 38-40, wherein the distal rim of the basket comprises a plurality of spikes.

42. The device of any of Embodiments 38-41, wherein the closing component operates between a first shape, a second shape, and any intermediate shape between the first shape and the second shape.

43. The device of any of Embodiments 38-42, wherein the closing component includes a closable loop.

44. The device of Embodiment 43, wherein the closable loop is configured to release from a position around the basket when tightened.

45. The device of Embodiment 43 or 44, wherein a portion of the basket around which the closable loop positioned is inwardly angled to assist release of the closable loop.

46. The device of any of Embodiments 43-45, wherein the closable loop comprises a suture material.

47. The device of Embodiment 46, wherein the suture material comprises a resorbable suture material.

48. The device of any of Embodiments 43-47, further comprising a knot pusher.

49. The device of any of Embodiments 43-48, wherein the closable loop comprises two stops spaced by a distance along the closable loop.

50. The device of Embodiment 49, wherein the distance is between about 6 millimeters and about 12 millimeters.

51. The device of any of Embodiments 43-50, wherein the closable loop is releasably bonded to the basket.

52. The device of Embodiment 51, wherein the releasable bond is releasable upon tightening the closable loop to allow the closable loop to release from a position around the basket.

53. The device of any of Embodiments 38-52, further comprising a delivery sheath configured to slide coaxially over the basket, wherein the closing component includes a closure clip coaxially over the delivery sheath.

54. The device of Embodiment 53, wherein the closure clip has a first shape over the delivery sheath and a second shape when moved off of the delivery sheath.

55. The device of Embodiment 54, wherein the second shape is sized such that, when the closure clip is positioned around the diverticulum, the closure clip draws serosa at the opening to the diverticulum into contact with the serosa.

56. The device of any of Embodiments 53-55, wherein the closure clip comprises a distal end including pointed elements.

57. The device of Embodiment 56, wherein the pointed elements are configured to turn radially inward when the closure clip is in the second shape.

58. The device of Embodiment 56 or 57, wherein the closing component comprises a plurality of closure clips each comprising a proximal end including recesses configured to complement the pointed elements when the closure clips are in the first shape.

59. The device of any of Embodiments 53-58, wherein the delivery sheath includes a radially expandable distal end.

60. The device of any of Embodiments 53-59, further comprising a pusher device configured to move the closure clip.

61. The device of Embodiment 60, wherein the pusher device includes a radially expandable distal end.

62. The device of Embodiment 60 or 61, wherein the pusher device includes a plurality of distally extending elements including inwardly-bent tips engaged with a distal-most closure clip.

63. The device of any of Embodiments 38-62, further comprising a first pusher and a second pusher coaxially over the first pusher, wherein the closing component includes a spring ring coaxially over the first pusher and distal to the second pusher.

64. The device of Embodiment 63, wherein the plurality of ribs include detents proximate to the distal rim and configured to engage the spring ring.

65. The device of Embodiment 63 or 64, wherein the basket is releasably coupled to the first pusher.

66. The device of any of Embodiments 38-65, wherein the closing component comprises a shape memory material.

67. The device of any of Embodiments 38-66, wherein at least one of the closing component and the basket includes a drug coating.

68. The device of Embodiment 67, wherein the drug coating includes at least one of a coagulation modifier and an antibiotic.

69. The device of Embodiment 67 or 68, wherein the closing component includes the drug coating.

70. The device of Embodiment 69, wherein a distal end of the closing component includes a closure clip including a distal end comprising the drug coating.

71. The device of any of Embodiments 67-70, wherein the distal ends of the plurality of ribs comprise the drug coating.

72. A closure clip comprising:
a generally tubular body comprising
a first end,
a second end,
a plurality of slits between the first end and the second end, the plurality of slits expandable upon radial expansion of the closure clip from a first state to a second state, and
a plurality of spikes proximate to the second end, the plurality of spikes configured to point in a direction substantially parallel to the longitudinal axis of the generally tubular body when the clip is in the first state and configured to point radially inward when the clip is in the second state, the tubular body slideable over a delivery tube in the first state.

73. The closure clip of Embodiment 72, wherein the generally tubular body comprises a shape memory material.

74. The closure clip of Embodiment 72 or 73, wherein the plurality of slits comprises a first slit extending from the first end of the generally tubular body toward the second end and a second slit extending from the second end toward, but not reaching, the first slit.

75. The closure clip of Embodiment 74, wherein the first slit and the second slit are substantially straight.

76. The closure clip of Embodiment 75, wherein the first slit and the second slit are substantially parallel to the longitudinal axis of the generally tubular body.

77. The closure clip of any of Embodiments 74-76, wherein the plurality of slits further comprises a third slit between the first end and the second end.

78. The closure clip of Embodiment 77, wherein the plurality of slits comprises sets of the first slit and the second slit alternating with the third slit around the circumference of the generally tubular body.

79. The closure clip of any of Embodiments 72-78, wherein the generally tubular body comprises a plurality of recesses proximate to the first end, the recesses configured to complement the plurality of spikes at least when the closure clip is in the first state.

80. The closure clip of any of Embodiments 72-79, further comprising a drug coating over at least a portion of the generally tubular body.

81. The closure clip of Embodiment 80, wherein the drug coating is over at least the plurality of spikes.

82. The closure clip of Embodiment 80 or 81, wherein the drug coating is over at least a portion of the generally tubular body proximate to the second end.

83. The device of any of Embodiments 80-82, wherein the drug coating includes at least one of a coagulation modifier and an antibiotic.

84. The device of any of Embodiments 80-83, wherein the closing component includes the drug coating.

85. A method of treating a diverticulum, the method comprising:
advancing a device to a site proximate to a diverticulum in a body lumen, the device comprising a basket defining a distal rim;
engaging at least a portion of tissue at the site with the distal rim of the basket; and
applying pressure to the diverticulum sufficient to cause at least a portion of the diverticulum to invert into the body lumen.

86. The method of Embodiment 85, wherein the body lumen is a colon.

87. The method of Embodiment 85 or 86, wherein advancing the device comprises advancing the device through the body lumen.

88. The method of any of Embodiments 85-87, wherein applying the pressure comprises applying negative pressure to the body lumen.

89. The method of any of Embodiments 85-88, wherein applying the pressure comprises applying negative pressure within the basket.

90. The method of Embodiment 85 or 86, wherein applying the pressure comprises applying positive pressure to the peritoneal cavity.

91. The method of any of Embodiments 85-90, wherein engaging the portion of the tissue comprises engaging the portion of the tissue with a plurality of teeth along the distal rim of the basket.

92. The method of any of Embodiments 85-91, further comprising closing the diverticulum including positioning a closing component around the basket.

93. The method of Embodiment 92, wherein the closing component comprises a closable loop releasably coupled to the device at the distal rim.

94. The method of Embodiment 93, wherein closing the diverticulum comprises tightening the closable loop around the inverted diverticulum.

95. The method of Embodiment 92, wherein the closing component comprises a closure clip coaxially over a delivery sheath configured to slide coaxially over the expandable basket.

96. The method of Embodiment 95, wherein closing the diverticulum comprises pushing the closure clip off of the delivery sheath.

97. The method of Embodiment 96, wherein closing the diverticulum comprises positioning the delivery sheath at least partially over the basket and at least partially withdrawing the basket prior to pushing the closure clip.

98. The method of Embodiment 95 or 96, further comprising, after closing the diverticulum and without withdrawing the device from the body lumen, engaging a second closure clip.

99. The method of Embodiment 98, further comprising treating a second diverticulum using the second closure clip.

100. The method of any of Embodiments 92-99, further comprising decreasing a pressure within the body lumen prior to closing the diverticulum.

101. A laparoscopic device for inverting a diverticulum, the device comprising:
a tubular member configured to be laparoscopically deployed at a site surrounding a diverticulum on a body lumen, the tubular member comprising:
a working lumen, and
a distal end configured to engage in a substantially airtight suction fit with tissue at the site surrounding the diverticulum,
wherein, upon application of positive pressure to the working lumen, at least a portion of the diverticulum is inverted into the body lumen.

102. The laparoscopic device of Embodiment 101, wherein the distal end of the tubular member comprises a hollow suction flange configured to be coupled to a negative pressure line, wherein, upon application of negative pressure through the negative pressure line, the distal end of the tubular member engages in the substantially airtight suction fit with the tissue at the site surrounding the diverticulum.

103. The laparoscopic device of Embodiment 102, wherein the suction flange comprises distal surface comprising a plurality of holes.

104. The laparoscopic device of any of Embodiments 101-103, wherein the tubular member comprises a proximal end comprising a sealed port configured to allow tools to enter the working lumen.

105. A closure clip assembly for use with a laparoscopic diverticulum inverting device, the closure clip assembly comprising:
a deployment tool; and
a closure clip comprising:
a distal region, and
a plurality of closure arms extending proximally from the distal region, the plurality of closure arms including proximal tips biased radially inward.

106. The closure clip assembly of Embodiment 105, wherein the distal region of the closure clip is internally threaded.

107. The closure clip assembly of Embodiment 106, wherein the deployment tool comprises:
an externally threaded distal region configured to threadably engage the internally threaded distal region of the closure clip;
an expander region proximal to the externally threaded distal region;
an elongate shaft proximal to the expander region; and
a handle proximal to the shaft, the expander region configured to radially expand the plurality of closure arms of the closure clip from an initial substantially parallel position to an expanded radially outward position as the handle is rotated in a first direction.

108. The closure clip assembly of Embodiment 107, wherein the expander region is configured to allow the plurality of closure arms of the closure clip to return toward the initial substantially parallel position as the handle is rotated in a second direction opposite the first direction.

109. The closure clip assembly of Embodiment 108, wherein the proximal tips are configured to draw toward each other when the plurality of closure arms of the closure clip return toward the initial substantially parallel position.

110. The closure clip assembly of any of Embodiments 107-109, wherein the deployment tool further comprises a frangible region between the expander region and the shaft.

111. The closure clip assembly of any of Embodiments 107-110, wherein the deployment tool further comprises a stop distal to the externally threaded distal region, the stop having a larger diameter than the externally threaded distal region.

112. The closure clip assembly of any of Embodiments 107-111, wherein the plurality of closure arms comprises curved regions sized to fit around the expander region, the plurality of closure arms in the initial substantially parallel position when the expander region is within the curved regions.

113. The closure clip assembly of Embodiment 105, wherein the plurality of closure arms comprises detents.

114. The closure clip assembly of Embodiment 105 or 113, wherein the deployment tool comprises:
an elongate shaft;
a spring ring around the distal region of the closure clip; and
a pulling mechanism coupled to the spring ring.

115. The closure clip assembly of Embodiment 114, wherein the elongate shaft comprises an atraumatic distal end.

116. The closure clip assembly of Embodiment 115, wherein the pulling mechanism comprises suture material.

117. The closure clip assembly of any of Embodiments 114-117, wherein the plurality of closure arms of the closure clip are radially inwardly compressed when the pulling mechanism proximally retracts the spring ring.

118. The closure clip assembly of Embodiment 105, wherein the deployment tool comprises:
an expandable member; and
an inflation lumen in fluid communication with the expandable member, the expandable member configured to radially expand the plurality of closure arms of the closure clip from an initial substantially parallel position to an expanded radially outward position as the expandable member is inflated through the inflation lumen.

119. The closure clip assembly of Embodiment 118, wherein the deployment tool further comprises:
a second expandable member distal to the expandable member; and
a second inflation lumen in fluid communication with the second expandable member.

120. The closure clip assembly of Embodiment 118 or 119, wherein the deployment tool is configured to allow the plurality of closure arms of the closure clip to return toward the initial substantially parallel position as the expandable member is deflated.

121. The closure clip assembly of Embodiment 120, wherein the proximal tips are configured to draw toward each other when the plurality of closure arms of the closure clip return toward the initial substantially parallel position.

122. The closure clip assembly of any of Embodiments 118-121, wherein the plurality of closure arms comprises curved regions sized to fit around the expandable member.

123. The closure clip assembly of any of Embodiments 105-122, wherein the closure clip comprises a shape memory material.

124. The closure clip assembly of Embodiment 123, wherein the plurality of closure arms are shape set in a substantially parallel configuration.

125. The closure clip assembly of Embodiment 123, wherein the plurality of closure arms are shape set in a radially expanded configuration.

126. A laparoscopic assembly comprising:
the laparoscopic device of any of Embodiments 101-104; and
the closure clip assembly of any of Embodiments 105-125.

127. The laparoscopic assembly of Embodiment 126, further comprising a colonoscope.

128. A method of inverting a diverticulum on a colon through a laparoscope, the method comprising:
applying a negative pressure to a distal surface of a hollow suction flange at a distal end of a tubular member that is against tissue surrounding the diverticulum, the negative pressure being sufficient to create a substantially airtight suction fit between the distal surface of the flange and the tissue surrounding the diverticulum; and
inverting at least a portion of the diverticulum.

129. The method of Embodiment 128, wherein inverting at least the portion of the diverticulum comprises applying a positive pressure to a working tube of the tubular member of the laparoscopic device, the positive pressure being sufficient to cause at least the portion of the diverticulum to invert into the colon.

130. The method of Embodiment 128, wherein inverting at least the portion of the diverticulum comprises pushing the diverticulum with an atraumatic distal end of a pusher tube, the pushing being sufficient to cause at least the portion of the diverticulum to invert into the colon.

131. The method of Embodiment 128, wherein inverting at least the portion of the diverticulum comprises pushing the diverticulum with a distal inflatable element, the pushing being sufficient to cause at least the portion of the diverticulum to invert into the colon.

132. The method of any of Embodiments 128-131, further comprising:
advancing a closing assembly through a working lumen of the tubular member to the inverted diverticulum; and
closing the diverticulum.

133. The method of Embodiment 132, wherein the closing assembly comprises:
a deployment tool; and
a closure clip.

134. The method of Embodiment 133,
wherein the closure clip comprises:
an internally threaded distal region, and
a plurality of closure arms extending proximally from the internally threaded distal region and including proximal tips,
wherein the deployment tool comprises:
an externally threaded distal region configured to threadably engage the internally threaded distal region of the closure clip,
an expander region proximal to the externally threaded distal region,
an elongate shaft proximal to the expander region, and
a handle proximal to the shaft, and
wherein closing the diverticulum comprises:
advancing the closure clip into the inverted diverticulum;
rotating the handle in a first direction to radially expand the plurality of closure arms from an initial substantially parallel position to an expanded radially outward position;
engaging a portion of tissue at a site proximate to the diverticulum with the proximal tips of the plurality of closure arms; and
rotating the handle in a second direction opposite the first direction to contract the plurality of closure arms from the expanded radially outward position toward the initial substantially parallel position.

135. The method of Embodiment 134, wherein the deployment tool comprises a frangible region between the expander region and shaft, and wherein closing the diverticulum comprises:
   after closing the diverticulum, severing the frangible region; and
   after severing the frangible region, removing the shaft and the handle.
136. The method of Embodiment 133,
   wherein the closure clip comprises:
      a distal region, and
      a plurality of closure arms extending proximally from the distal region and including proximal tips,
   wherein the deployment tool comprises:
      an elongate shaft,
      a spring ring around the distal region of the closure clip, and
      a pulling mechanism coupled to the spring ring,
   wherein closing the diverticulum comprises
      advancing the closure clip into the inverted diverticulum;
      engaging a portion of tissue at a site proximate to the diverticulum with the proximal tips of the plurality of closure arms; and
      proximally retracting the spring ring over the plurality of closure arms to contract the plurality of closure arms radially inward.
137. The method of Embodiment 136, wherein closing the diverticulum comprises decoupling the pulling mechanism from the spring ring.
138. The method of Embodiment 133,
   wherein the closure clip comprises:
      a distal region, and
      a plurality of closure arms extending proximally from the distal region and including proximal tips,
   wherein the deployment tool comprises:
      an expandable member, and
      an inflation lumen in fluid communication with the expandable member,
   wherein closing the diverticulum comprises:
      advancing the closure clip into the inverted diverticulum;
      inflating the expandable member through the inflation lumen;
      engaging a portion of tissue at a site proximate to the diverticulum with the proximal tips of the plurality of closure arms; and
      deflating the expandable member through the inflation lumen.
139. The method of Embodiment 134, wherein the deployment tool comprises a second expandable member and a second inflation lumen in fluid communication with the second expandable member, the second expandable member distal to the expandable member.
140. The method of any of Embodiments 133-139, wherein the plurality of closure arms comprises proximal tips biased radially inward, and wherein engaging the portion of tissue at the site proximate to the diverticulum with the distal plurality of closure arms comprises extending the tips through the tissue at the site proximate to the diverticulum.
141. The method of any of Embodiments 128-140, further comprising decreasing a pressure within the body lumen prior to closing the diverticulum.
142. The method of any of Embodiments 128-131, wherein the closing assembly comprises a suturing tool.
143. The method of Embodiment 140, wherein closing the diverticulum comprises suturing the tissue surrounding the inverted diverticulum.
144. The method of Embodiment 141, wherein suturing the tissue surrounding the inverted diverticulum comprises tying a purse string suture.

What is claimed is:

1. A laparoscopic device for inverting a diverticulum, the device comprising:
   a tubular member configured to be laparoscopically deployed at a site surrounding a diverticulum on a body lumen, the tubular member comprising:
      a working lumen, and
      a distal end configured to engage in a substantially airtight suction fit with tissue at the site surrounding the diverticulum, wherein the distal end of the tubular member comprises an annular suction flange,
      wherein, upon application of positive pressure to the working lumen, at least a portion of the diverticulum is inverted into the body lumen.
2. The laparoscopic device of claim 1, wherein the distal end of the tubular member comprises a hollow suction flange configured to be coupled to a negative pressure line, wherein, upon application of negative pressure through the negative pressure line, the distal end of the tubular member engages in the substantially airtight suction fit with the tissue at the site surrounding the diverticulum.
3. The laparoscopic device of claim 2, wherein the suction flange comprises a distal surface comprising a plurality of holes.
4. The laparoscopic device of claim 1, wherein the tubular member comprises a proximal end comprising a sealed port configured to allow tools to enter the working lumen.
5. The laparoscopic device of claim 1, wherein the device is configured such that the application of positive pressure contacts the diverticulum.
6. The laparoscopic device of claim 1, wherein the positive pressure is configured to directly act on the divertuculum.
7. A method of inverting a diverticulum on a colon through a laparoscope inserted through an incision, the method comprising:
   applying a negative pressure to a distal surface of a hollow suction flange at a distal end of a tubular member that is against tissue surrounding the diverticulum, the negative pressure being sufficient to create a substantially airtight suction fit between the distal surface of the flange and the tissue surrounding the diverticulum; and
   inverting at least a portion of the diverticulum.
8. The method of claim 7, wherein inverting at least the portion of the diverticulum comprises applying a positive pressure to a working tube of the tubular member of the laparoscopic device, the positive pressure being sufficient to cause at least the portion of the diverticulum to invert into the colon.
9. The method of claim 7, wherein inverting at least the portion of the diverticulum comprises pushing the diverticulum with an atraumatic distal end of a pusher tube, the pushing being sufficient to cause at least the portion of the diverticulum to invert into the colon.
10. The method of claim 7, wherein inverting at least the portion of the diverticulum comprises pushing the diverticulum with a distal inflatable element, the pushing being sufficient to cause at least the portion of the diverticulum to invert into the colon.

11. The method of claim 7, further comprising:
advancing a closing assembly through a working lumen of the tubular member to the inverted diverticulum; and
closing the diverticulum.

12. The method of claim 11, wherein the closing assembly comprises:
a deployment tool; and
a closure clip.

13. The method of claim 12,
wherein the closure clip comprises:
an internally threaded distal region, and
a plurality of closure arms extending proximally from the internally threaded distal region and including proximal tips,
wherein the deployment tool comprises:
an externally threaded distal region configured to threadably engage the internally threaded distal region of the closure clip,
an expander region proximal to the externally threaded distal region,
an elongate shaft proximal to the expander region, and
a handle proximal to the shaft, and
wherein closing the diverticulum comprises:
advancing the closure clip into the inverted diverticulum;
rotating the handle in a first direction to radially expand the plurality of closure arms from an initial substantially parallel position to an expanded radially outward position;
engaging a portion of tissue at a site proximate to the diverticulum with the proximal tips of the plurality of closure arms; and
rotating the handle in a second direction opposite the first direction to contract the plurality of closure arms from the expanded radially outward position toward the initial substantially parallel position.

14. The method of claim 13, wherein the deployment tool comprises a frangible region between the expander region and shaft, and wherein closing the diverticulum comprises:
after closing the diverticulum, severing the frangible region; and
after severing the frangible region, removing the shaft and the handle.

15. The method of claim 12,
wherein the closure clip comprises:
a distal region, and
a plurality of closure arms extending proximally from the distal region and including proximal tips,
wherein the deployment tool comprises:
an elongate shaft,
a spring ring around the distal region of the closure clip, and
a pulling mechanism coupled to the spring ring,
wherein closing the diverticulum comprises:
advancing the closure clip into the inverted diverticulum;
engaging a portion of tissue at a site proximate to the diverticulum with the proximal tips of the plurality of closure arms; and
proximally retracting the spring ring over the plurality of closure arms to contract the plurality of closure arms radially inward.

16. The method of claim 15, wherein closing the diverticulum comprises decoupling the pulling mechanism from the spring ring.

17. The method of claim 12,
wherein the closure clip comprises:
a distal region, and
a plurality of closure arms extending proximally from the distal region and including proximal tips,
wherein the deployment tool comprises:
an expandable member, and
an inflation lumen in fluid communication with the expandable member,
wherein closing the diverticulum comprises:
advancing the closure clip into the inverted diverticulum;
inflating the expandable member through the inflation lumen;
engaging a portion of tissue at a site proximate to the diverticulum with the proximal tips of the plurality of closure arms; and
deflating the expandable member through the inflation lumen.

18. The method of claim 17, wherein the deployment tool comprises a second expandable member and a second inflation lumen in fluid communication with the second expandable member, the second expandable member distal to the expandable member.

19. The method of claim 12, wherein the closure clip comprises a plurality of closure arms extending proximally from a distal region, and wherein the plurality of closure arms comprises proximal tips biased radially inward, and wherein engaging the portion of tissue at the site proximate to the diverticulum with the distal plurality of closure arms comprises extending the tips through the tissue at the site proximate to the diverticulum.

20. The method of claim 11, wherein the closing assembly comprises a suturing tool.

21. The method of claim 20, wherein closing the diverticulum comprises suturing the tissue surrounding the inverted diverticulum.

22. The method of claim 21, wherein suturing the tissue surrounding the inverted diverticulum comprises tying a purse string suture.

23. The method of claim 7, further comprising decreasing a pressure within the color prior to closing the diverticulum.

24. A laparoscopic device for inverting a diverticulum, the device comprising:
a tubular member configured to be laparoscopically deployed at a site surrounding a diverticulum on a body lumen, the tubular member comprising:
a working lumen, and
a distal end configured to engage in a substantially airtight suction fit with tissue at the site surrounding the diverticulum,
wherein, upon application of positive pressure to the working lumen, at least a portion of the diverticulum is inverted into the body lumen, wherein the positive pressure is configured to directly act on the divertuculum.

25. The laparoscopic device of claim 24, wherein the distal end of the tubular member comprises a hollow suction flange configured to be coupled to a negative pressure line, wherein, upon application of negative pressure through the negative pressure line, the distal end of the tubular member engages in the substantially airtight suction fit with the tissue at the site surrounding the diverticulum.

26. The laparoscopic device of claim 25, wherein the suction flange comprises a distal surface comprising a plurality of holes.

27. The laparoscopic device of claim 24, wherein the tubular member comprises a proximal end comprising a sealed port configured to allow tools to enter the working lumen.

28. The laparoscopic device of claim 24, wherein the device is configured such that the application of positive pressure contacts the diverticulum.

* * * * *

UNITED STATES PATENT AND TRADEMARK OFFICE
CERTIFICATE OF CORRECTION

| | | |
|---|---|---|
| PATENT NO. | : 9,084,605 B2 | Page 1 of 1 |
| APPLICATION NO. | : 14/234990 | |
| DATED | : July 21, 2015 | |
| INVENTOR(S) | : Hawkins et al. | |

It is certified that error appears in the above-identified patent and that said Letters Patent is hereby corrected as shown below:

Title Page

Item (71), under "Applicant", in Column 1, Line 2, delete "Development, LLC," and insert -- Development LLC, --, therefor.

Specification

In Column 1, Line 7, delete "35 U.S.C. §371" and insert -- 35 U.S.C. § 371 --, therefor.

In Column 40, Line 22, delete "comprises distal" and insert -- comprises a distal --, therefor.

In Column 43, Line 20, delete "comprises" and insert -- comprises: --, therefor.

Claims

In Column 46, Line 43, in Claim 23, delete "the color prior" and insert -- the colon prior --, therefor.

Signed and Sealed this
Twenty-third Day of February, 2016

Michelle K. Lee
*Director of the United States Patent and Trademark Office*